United States Patent
Dhugga

(10) Patent No.: US 7,265,265 B2
(45) Date of Patent: Sep. 4, 2007

(54) GENES FOR GALACTOMANNAN PRODUCTION IN PLANTS AND METHODS OF USE

(75) Inventor: Kanwarpal S. Dhugga, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 523 days.

(21) Appl. No.: 10/713,836

(22) Filed: Nov. 14, 2003

(65) Prior Publication Data

US 2004/0143871 A1  Jul. 22, 2004

Related U.S. Application Data

(60) Provisional application No. 60/490,022, filed on Jul. 25, 2003, provisional application No. 60/426,127, filed on Nov. 14, 2002.

(51) Int. Cl.
| | |
|---|---|
| C12N 15/29 | (2006.01) |
| C12N 15/52 | (2006.01) |
| C12N 15/82 | (2006.01) |
| A01H 5/00 | (2006.01) |
| A01H 5/10 | (2006.01) |

(52) U.S. Cl. .................. 800/284; 800/278; 800/287; 800/298; 536/23.1; 536/23.2; 536/23.6; 435/320.1; 435/419

(58) Field of Classification Search ............... 536/23.1, 536/23.2, 23.6; 435/320.1, 419; 800/278, 800/284, 287, 288, 290, 298
See application file for complete search history.

(56) References Cited

U.S. PATENT DOCUMENTS 5,234,825 A   8/1993   McCleary et al.

FOREIGN PATENT DOCUMENTS

| EP | 0 946 599 B1 | 2/2001 |
|---|---|---|
| WO | WO97/20937 A2 | 6/1997 |
| WO | WO97/20937 A3 | 6/1997 |
| WO | WO98/54335 A1 | 12/1998 |
| WO | WO99/60103 A2 | 11/1999 |
| WO | WO99/60103 A3 | 11/1999 |

OTHER PUBLICATIONS

Saxena I. et al., Cell Biology; 2000, vol. 3; pp. 523-531.*
Liepman A. et al. PNAS; Feb. 8, 2005; vol. 102, No. 6 pp. 2221-2226.*
Dhugga K. et al. Science; Jan. 16, 2004; vol. 303, pp. 363-366.*
Anderson et al., Water-Soluble Food Gums and Their Role in Product Development, Cereal Foods (1988) 33(10):844-850.
Edwards et al., Biosynthesis of legume-seed galactomannans in vitro, Planta (1989) 178:41-51.
Edwards et al., Control of mannose/galactose ratio during galactomannan formation in developing legume seeds, Planta (1992) 187:67-74.
Keegstra et al., Plant glycosyltransferases, Curr. Opin. Plant Biology (2001) 4:219-224.
Maier et al., Guar, Locust Bean, Tara, and Fenugreek Gums, Industrial Gums: Polysaccharides and Their Derivatives, Third Edition (1993) Chapter 8:181-226, Whistler and BeMiller eds, Academic Press, San Diego and London.
Reid, J.S.G., Cell Wall Storage Carbohydrates in Seeds-Biochemistry of the Seed "Gums" and "Hemicelluloses", Advances in Botanical Research (1985) 11:125-155.
Reid, J.S.G., Biosynthesis of galactomannan in the endosperms of developing fenugreek (*Trigonella foenum-graecum* L.) and guar (*Cyamopsis tetragonoloba* [L.] Taub.) seeds, Food Hydrocolloids (1987) 1(5/6):381-385.
Reid, J.S.G., Mechanism and regulation of galactomannan biosynthesis in developing leguminous seeds, Biochem. Soc. Trans. (1992) 20:23-26.
Reid, J.S.G., Enzyme specificity in galactomannan biosynthesis, Planta (1995) 195:489-495.
Saxena et al., Cellulose synthases and related enzymes, Curr. Opin. Plant Biology (2000) 3:523-531.
Ward et al., Water-Soluble Gums Used in Snack Foods and Cereal Products, Cereal Foods (1993) 38(10):748-752.
Whistler, et al., Introduction to Industrial Gums, Industrial Gums: Polysaccharides and Their Derivatives, Third Edition (1993) Chapter 1:1-19, Whistler and BeMiller eds, Academic Press, San Diego and London.
Whistler et al., Guar and Locust Bean Gums, Carbohydrate Chemistry for Food Scientists (1997) Chapter 9:171-177.

* cited by examiner

*Primary Examiner*—Russell P. Kallis

(57) ABSTRACT

The invention relates to the genetic manipulation of plants, particularly to the expression of galactomannan biosynthetic genes in transformed plants. Isolated nucleotide molecules comprising nucleotide sequences encoding mannan synthase and galactosyltransferases and methods for their use are provided. The nucleotide molecules find use in the production of gum in transformed plants.

22 Claims, 33 Drawing Sheets

>*CtManS* -1964 bp.
GGAATTCGGCACGAGGTGCCTGCAACAAGTCACTAGTCCATCCTGCAGTTCCCTAACCCT
CCCTAGTGTCTTTCTCTTCAGGCTCCATATTCCTTTATAACTACTACAATAGATACAATG
AGAAACCTAATCTTCGAGGAGCCTGAAGGGATTCCAGGCAACAGTTCAAGCAGTCTGCGC
TATGCCTGGCAATCAATTCGTGCCCAGTGATCATACCTCTTCTAAAACTAGCAGTCATA
GTGTGCTCAGTTATGTCAATCATGCTATTTGTTGAAAGAGTAGCCATGGCAGCTGTAATT
TTGATTGTCAAAGTGCTGAGGAAGAAAAGATACACCAAGTATAACTTGGAAGCCATGAAA
CAGAAGCTAGAGAGAAGCAAAAAATACCCCATGGTGCTGATCCAAATACCTATGTATAAC
GAGAAAGAGGTGTACAAGCTTTCCATTGGAGCAGTATGTGGGCTTTCATGGCCAGCTGAC
AGGTTCATAGTTCAAGTTCTTGATGACTCAACAAATCCAGTCTTAAGGGAGTTGGTTGAA
ATGGAGTGTCAAAAATGGATACAGAAAGGTGTGAATGTCAAGTATGAAAATAGGAGAAAT
CGCAATGGTTACAAAGCAGGTGCCTTAAAAGAGGGTTTGGAGAAGCAATATGTAGAGGAT
TGTGAGTTTGTAGCAATATTTGATGCAGATTTCCAACCAGATGCGGATTTTCTTTGGAAC
ACAATTCCTTATCTGCTGGAAAATCCAAAGTTGGGTTTGGTTCAGGCGAGATGGAAATTT
GTGAACTCAGAAGAATGTATGATGACACGGCTTCAAGAGATGTCACTAGATTACCACTTT
AGTGTTGAACAGGAAGTCGGCTCTTCAACATACTCATTCTTCGGTTTCAATGGAACAGCA
GGAGTTTGGCGGATCCAAGCCATAAAAGATGCTGGAGGATGGAAAGACCGAACAACGGTG
GAGGATATGGACCTTGCAGTTAGAGCAAGCTTGCATGGCTGGGAATTTGTTTTTGTGGGT
GATGTAAAGGTCAAAAATGAATTACCAAGTACATTTAAAGCATATCGATTTCAGCAGCAC
AGGTGGTCATGCGGTCCAGCTAATCTCTTTAAGAAAATGACCAAGGAAATCATCTGTTGC
AAAAGGGTGCCACTTCTCAAGAGACTCCATCTCATCTATGCTTTCTTCTTTGTGAGAAAA
ATAGTTGCACACTGGGTTACGTTCTTCTTTTACTGCATAGTTATACCAGCTTGTGTGATA
GTTCCCGAAGTTAATCTCAAAAAGCAGATTGCCATATACATCCCAGCAACCATTACAATT
CTAAATGCAGTCTCCACCCCAAGATCCATGCATCTACTAGTACTCTGGATACTCTTTGAG
AATGTCATGTCACTCCATCGAACTAAAGCAGCAATTATTGGACTCTTGGAAGCAAATCGT
GTCAATGAATGGGTTGTGACTGAGAAGCTTGGAAATGCCATGAAACAGAGGAACAATGCT
AGGCCATCAAGAGCTTCACGGTTTCGAATTATAGAAAGGATCCACCCATTGGAGATTATA
GTGGGGATGTATATGCTGCACTGTGCAACCTATGACCTGTTATTCGGACACGACCATTTC
TTTGTCTATCTTCTGTTGCAGGCAGGGGCGTTCTTTACAATGGGATTTGGCCTAGTAGGA
ACAATTGTACCCACCTAAAGCTTAAAGGTCATGGACTCATGAACATAAGTATTAGTGTAT
GAACGGGTCCTGTTTGTTTTAAGACTCTAAGTCTAGTGAACTAGCTATCCATAAGCATAG
AACTGTAAGAGAAGCTACGGCTACTTAGTAGAAGCATTCCATATGGTATCAGGACTTCTT
TGTACCCATGTATAAGAACCAGAATCAAAACGTATAAACATGTCCATAATATGAAGCTTA
AATAAATCTGTTATCTGCACTAAAAAAAAAAAAAAAAAAAAAC

FIGURE 1

>CtMANS - 526 aa.
MRNLIFEEPEGIPGNSSSSLRYAWQSIRAPVIIPLLKLAVIVCSVMSIMLFVERVAMAAV
ILIVKVLRKKRYTKYNLEAMKQKLERSKKYPMVLIQIPMYNEKEVYKLSIGAVCGLSWPA
DRFIVQVLDDSTNPVLRELVEMECQKWIQKGVNVKYENRRNRNGYKAGALKEGLEKQYVE
DCEFVAIFDADFQPDADFLWNTIPYLLENPKLGLVQARWKFVNSEECMMTRLQEMSLDYH
FSVEQEVGSSTYSFFGFNGTAGVWRIQAIKDAGGWKDRTTVEDMDLAVRASLHGWEFVFV
GDVKVKNELPSTFKAYRFQQHRWSCGPANLFKKMTKEIICCKRVPLLKRLHLIYAFFFVR
KIVAHWVTFFFYCIVIPACVIVPEVNLKKQIAIYIPATITILNAVSTPRSMHLLVLWILF
ENVMSLHRTKAAIIGLLEANRVNEWVVTEKLGNAMKQRNNARPSRASRFRIIERIHPLEI
IVGMYMLHCATYDLLFGHDHFFVYLLLQAGAFFTMGFGLVGTIVPT

FIGURE 2

>CtGalT2 - 1609 bp.
GGAATTCGGCACGAGGCTCCCATGGCGAAATCCTCCAATTCCAGAAACAAAATTTCACAC
GTAAACCTCTCCGACGGTTTCCTCTTCCTCGCCGGAGCATTCTCCGCGCTTCTAATCGTT
TGGGGTTTCTCCTCCTTCACAACCCCCATCCCTAACGAAACCCCAACCTTCGAATCACTT
TCGGTAAATTCTCACCAAAACGACGCCGTTTCGCGCGGGGACCGGATTTCCGGTTCGAT
CCCCCGGACCGGACTTTCTACGACGACCCGGAAATGGGGTACACCATAGACACGACGGTG
CGAGATTGGGATGCAAAGCGTGAGGAGTGGCTGCGGCTTCATCCTTCCTTCGCCGCCGGA
GCGAGAGAACGAGTTTTGGTGGTGACCGGATCGCAGCCGGCACCGTGCCGGAATCCATC
GGCGACCACTTGCTGTTACGGTTTTTTAAGAACAAGGTGGATTACTGTCGGTTACACGGG
TACGATATCGTGTACAACAATGCATTGTTACACCCGAAAATGTTCACGTATTGGGCGAAG
TACCCGGTGGTGCGGGCCGCGATGATGGCCCACCCGGAAGCCGAGTGGATCTGGTGGGTC
GACTCGGACGCGTTGTTCACCGACATGGAGTTCAAACTACCATTAGATCACTACAAGGAT
CACAACCTCGTCGTCCATGGCTGGGCCCACCTCATCCACGAGAAACGTAGTTGGACGGGC
CTCAACGCCGGCGTCTTCCTCATCAGAAACTGTCAATGGTCATTGGACTTCATAAACGAA
TGGGCCAGCATGGGCCCACAAACTCCGAACTACGAGAAATGGGGTCAAACCCTAAAGTCA
ACTTTCAAAGACAAATTCTTCCCGGAGTCAGACGATCAGACGGGCCTCGCTTACCTGATC
GCGATCGAGAAGAAAAATGGGCGGACAAGATTTACTTAGAGAACTCGTATTATTTCGAA
GGGTACTGGGAAGAAATCGTCGGAACATTCGAGAATATAAGCAAGAAATACAACGAGATC
GAAACGGGGGTGCGCAGGTTAAGAAGGCGTCACGCGGAGAAAGTGAGTGAAGCTTACGGT
GAAGAGAGGGAGAAATATTTAACGGAAGCAGGTAACGGTAAAGGAAGCTGGAGACGGCCG
TTTGTGACGCACTTCACGGGGTGTCAACCTTGTAGCGGAAAATATAACGCTATGTATAAC
GCCGAAGATTGTTGGAACGGAATGCGTAAAGCCCTTAATTTCGCTGATAATCAGGTGATG
CGTAAATATGGTTTCGTACACCCGGATGTACTAGATAATTCCGTTTCGCCGATTCCGTTT
GATTATCCCCGTAACCGCTCAGGTAATAATCATATTTAATGGAATCTAATTATTGTTGAC
CGCTGGCTACTCAGATTCTCCATGTGTTCTGTAAAGTACTAGTACTACTAGTATTAAATT
TCTTAGTGTATATTTTATAATATTTTTATTGTATATTTTCTGGCGTTTTGCATATATAGT
ATCGTGTGGAGTAGTATTTAATTATGCATAAGTGAAGGGATAATTTTATTCTTTTCGAAT
CCCTAAAAAAAAAAAAAAAAAAAAAAAAAAAAAAAAAAAAAAAAACT

FIGURE 3

>CtGALT2 - 445 aa.
MAKSSNSRNKISHVNLSDGFLFLAGAFSAFLIVWGFSSFTTPIPNETPTFESLSVNSHQN
DAVSRGGPDFRFDPPDRTFYDDPEMGYTIDTTVRDWDAKREEWLRLHPSFAAGARERVLV
VTGSQPAPCRNPIGDHLLLRFFKNKVDYCRLHGYDIVYNNALLHPKMFTYWAKYPVVRAA
MMAHPEAEWIWWVDSDALFTDMEVXLPLDHYKDHNLVVHGWAHLIHEKRSWTGLNAGVFL
IRNCQWSLDFINEWASMGPQTPNYEKWGQTLKSTFKDKFFPESDDQTGLAYLIAIEKEKW
ADKIYLENSYYFEGYWEEIVGTFENISKKYNEIETGVRRLRRRHAEKVSEAYGEEREKYL
TEAGNGKGSWRRPFVTHFTGCQPCSGKYNAMYNAEDCWNGMRKALNFADNQVMRKYGFVH
PDVLDNSVSPIPFDYPRNRSGNNHI

FIGURE 4

|              |       | 1                                                            60 |
|--------------|-------|---|
| Fenugreek    | (1)   | ---------------------------------------------GCGACGAAATTTGG---T |
| Guar-GalT1   | (1)   | GGAATTCGGCACGAGGCTCCAGTATCAGATTCACTCACTCCCATGGCCAAATTTGG---T |
| Guar-GalT2   | (1)   | ------------------GGAATTCGGCACGAGGCTCCCATGGCGAAATCCTCCAAT |
| Consensus    | (1)   |                   G  A  C            CTCCCATGGCGAAATTTGG    T |

|              |       | 61                                                          120 |
|--------------|-------|---|
| Fenugreek    | (16)  | TCCAAAACAAATCCTCTCC---ATGGCTCTCAAATGGTTGCATCTTCCTCCTAGGTGCA |
| Guar-GalT1   | (58)  | TCCAGAAACAAATCCCCTAA---ATGGATCTCCAACGGTTGCTGCTTCCTCCTAGGAGCA |
| Guar-GalT2   | (40)  | TCCAGAAACAAAATTTCACACGTAAACCTCTCCGACGGTTTCCTCTTCCTCGCCGGAGCA |
| Consensus    | (61)  | TCCAGAAACAAATCCTCTCA  ATGGCTCTCCAACGGTTGC TCTTCCTCCTAGGAGCA |

|              |       | 121                                                         180 |
|--------------|-------|---|
| Fenugreek    | (73)  | ATGTCAGCTCTTCTTATGATTTGGGGGCTCAATTCCTTCATCGCTCGAATCCCAAACTCG |
| Guar-GalT1   | (115) | TTCACTGCTCTTCTTCTGCTCTGGGGTTTATGCTCCTTCATCATCCCCATCCCAAACACC |
| Guar-GalT2   | (100) | TTCTCCGCGCTTCTAATCGTTTGGGGTTTCTCCTCCTTCACAACCCCCATCCCTAACGAA |
| Consensus    | (121) | TTCTC GCTCTTCTTATG TTTGGGGTTTCT CTCCTTCATCACCCCCATCCCAAAC CC |

|              |       | 181                                                         240 |
|--------------|-------|---|
| Fenugreek    | (133) | AACCCAAAATTCAACTCCTTCGACCACCAAACTCAAATCCTTAAACTTCACCACAAACACC |
| Guar-GalT1   | (175) | GACCCCAAGCTCAACTCCGTCGCCACCAGTTTGAGATCCCTTAACTTTCCCAAAAACCCG |
| Guar-GalT2   | (160) | ACCCCAACCTTCGAATCACT--------T-----TCGGTAAATTCTGACCAAAACGAC |
| Consensus    | (181) | AACCCAAA TTCAACTCC TC CCACCA T T A ATCC TAAACTTTCCCAAAAAC CC |

|              |       | 241                                                         300 |
|--------------|-------|---|
| Fenugreek    | (193) | A-----AG-TTTGCTGGTCCTGATTTGTTACATGACCCTTCAGACAAAACCTTCTATGAT |
| Guar-GalT1   | (235) | GCTGCCAC-CTTGCC--TCCCAACTTGCAGCACGACCCTCCTGACACCACCTTCTACGAC |
| Guar-GalT2   | (205) | GCCGTTTCGCGCGGGGGACCGGATTCCGGTTCGATCCCCCGGACCGGACTTTCTACGAC |
| Consensus    | (241) | GC G  AC CTTGC  GGTCC GATTTGC GCACGACCCTCC GACA ACCTTCTACGAC |

|              |       | 301                                                         360 |
|--------------|-------|---|
| Fenugreek    | (247) | GATCCAGAAACATGTTACACCATGATGGACAAACCAATGAAAAATTGGGATGAGAAGCGT |
| Guar-GalT1   | (292) | GACCCCGAAACCAGTTATACCAT---GGACAAACCAATGAAAAACTGGGACGAGAAGCGT |
| Guar-GalT2   | (265) | GACCCGGAAATGGGGTACACCAT---AGACACGACGGTGCGAGATTGGGATGCAAAGCGT |
| Consensus    | (301) | GACCC GAAAC  GTTACACCAT   GGACAAACCAATGAAAAATTGGGATGAGAAGCGT |

|              |       | 361                                                         420 |
|--------------|-------|---|
| Fenugreek    | (307) | AAAGAATGGCTATTTTCATCATCCCTCATTCGCGGCTGGAGCAACCGAAAAGATACTTGTT |
| Guar-GalT1   | (349) | AAGGAGTGGTTGCTGCATCATCCTTCGTTTGCGCCGCAGCACGCGATAAGATTCTCCTG |
| Guar-GalT2   | (322) | GAGGAGTGGCTGCGGCTTCATCCTTCCTTCGCCGCCGGAGCGAGAGAACGAGTTTTGGTG |
| Consensus    | (361) | AAGGAGTGGCTGCTGCATCATCCTTC TTCGCCGCCGGAGCAAGCGAAAAGATTCT GTG |

|              |       | 421                                                         480 |
|--------------|-------|---|
| Fenugreek    | (367) | ATAACGGGTTCACAGCCGACAAAGTGTGACAACCCCATCGGAGACCACCTTTTACTAAGG |
| Guar-GalT1   | (409) | GTGACAGGTTCTCAGCCGAAACGGTGCCATAACCCGATCGGCGACCACCTCCTGTTGCGG |
| Guar-GalT2   | (382) | GTGACCGGATCGCAGCCGGCACCGTGCCGGAATCCCATCGGCGACCAGTTGCTGTTACGG |
| Consensus    | (421) | GTGAC GGTTC CAGCCGACAC GTGCCA AACCCCATCGGCGACCACCT CTGTTACGG |

|              |       | 481                                                         540 |
|--------------|-------|---|
| Fenugreek    | (427) | TTCTATAAAAACAAGGTTGATTATTGTCGTATACACAACCACGACATAATCTACAACAAT |
| Guar-GalT1   | (469) | TTTTTCAAGAACAAGGTGGATTACTGCCGGCTGCACAACTACGACATAATTTACAACAAC |
| Guar-GalT2   | (442) | TTTTTTAAGAACAAGGTGGATTACTGTCGGTTACACGGGTACGATATCGTGTACAACAAT |
| Consensus    | (481) | TTTTTTAAGAACAAGGTGGATTACTGTCGG TACACAACTACGACATAAT TACAACAAT |

|              |       | 541                                                         600 |
|--------------|-------|---|
| Fenugreek    | (487) | GCATTGTTGCACCCAAAAATGGACTCTTACTGGGCCAAGTATCCTATGGTTCGGGCCGCA |
| Guar-GalT1   | (529) | GCGCTTCTGCATCCTAAAATGAACTCTTATTGGGCCAAGTATCCAGTGATTCGGGCGGCG |
| Guar-GalT2   | (502) | GCATTGTTACACCCGAAAATGTTCACGTATTGGGCGAAGTACCCGGTGGTGCGGGCCGCG |
| Consensus    | (541) | GCATTGTTGCACCC AAAATG ACTCTTATTGGGCCAAGTATCC GTGGTTCGGGCCGCG |

|              |       | 601                                                         660 |
|--------------|-------|---|
| Fenugreek    | (547) | ATGTTGGCCCATCCGGAAGTAGAATGGATATGCTGGGTCGACTCTGATGCCATCTTTACC |
| Guar-GalT1   | (589) | ATGATGGCCCATCCGGAAGTGGAGTGGGTGTGGTGGGTGGACTCGGACGCGGTTTTCACG |
| Guar-GalT2   | (562) | ATGATGGCCCACCCGGAAGCCGAGTGGATCTGGTGGGTCGACTCGGACGCGTTGTTCACC |
| Consensus    | (601) | ATGATGGCCCATCCGGAAGT GAGTGGAT TGGTGGGTCGACTCGGACGCG T TTCACC |

|              |       | 661                                                         720 |
|--------------|-------|---|
| Fenugreek    | (607) | GATATGGAATTCAAGTTACCGTTATGGCGTTACAAGGATCACAACCTTGTGATTCATGGT |
| Guar-GalT1   | (649) | GACATGGAGTTCAAGCTTCCGTTAAAGCGTTATAAGAACCACAATCTGGTGGTTCACGGT |
| Guar-GalT2   | (622) | GACATGGAGTTCAAAACTACCATTAGATCACTACAAGGATCACAACCTCGTCGTCATGGC |
| Consensus    | (661) | GACATGGAGTTCAAGCTACCGTTA AGCGTTACAAGGATCACAACCT GTGGTTCATGGT |

```
                     721                                                        780
Fenugreek    (667)   TGGGAAGAGTTGGTTAAGACAGAGCATAGTTGGACCGGGCTTAACGCGGGTGTTTCTTG
Guar-GalT1   (709)   TGGGAAGGATTGGTACGGTTGAACCATAGCTGGACGGGTCTAAACGCGGGCGTATTCTTG
Guar-GalT2   (682)   TGGGCCCACCTCATCCACGAGAAACGTAGTTGGACGGGCCTCAACGCCGGCGTCTTCCTC
Consensus    (721)   TGGGAAGA TTGGT CAG  GAA CATAGTTGGACGGG CT AACGCGGGCGT TTCTTG
                     781                                                        840
Fenugreek    (727)   ATGAGGAATTGTCAATGGTCGTTGGATTTTATGGATGTTTGGGCCAGTATGGGCCCAAAC
Guar-GalT1   (769)   ATTCGGAATTGCCAGTGGTCGTTGGAGTTCATGGATGTGTGGGTGAGCATGGGGCCACAG
Guar-GalT2   (742)   ATCAGAAACTGTCAATGGTCATTGGACTTCATAAGCGAATGGGCCAGCATGGGCCCACAA
Consensus    (781)   AT AGGAATTGTCAATGGTCGTTGGA TTCATGGATGT TGGGCCAGCATGGGCCCACA
                     841                                                        900
Fenugreek    (787)   AGCCCCGGAATACGAGAAATGGGGGGAGAGACTTAGAGAAACTTTTAAGACAAAAGTGGTA
Guar-GalT1   (829)   ACTCCGGAATACGAGAAATGGGGGGAGAGGTTGAGAGAGACATTCAAGGACAAGGTGCTG
Guar-GalT2   (802)   ACTCCGAACTACGAGAAATGGGGTCAACCCTAAAGTCAACTTTCAAAGACAAATTCTTC
Consensus    (841)   ACTCCGGAATACGAGAAATGGGGGGAGAG CT AGAGAAACTTTCAAGGACAAAGTG T
                     901                                                        960
Fenugreek    (847)   CGTGATTCAGATGATCAGACGGCGCTTGCTTACTTGATCGCGATGGGAGA---GGACAAG
Guar-GalT1   (889)   CCTGATTCGGACGATCAGACGGCGCTGGCTTACCTGATCGCGACGGATAATAAGGACACG
Guar-GalT2   (862)   CCGGAGTCAGACGATCAGACGGGCCTCGCTTACCTGATCGCGATCGAGAA---AGAAAAA
Consensus    (901)   CCTGATTCAGACGATCAGACGGCGCT GCTTACCTGATCGCGATGGA AA  GGACAAG
                     961                                                        1020
Fenugreek    (904)   TGGACAAAGAAGATCTATATGGAGAATGAGTATTATTTTGAAGGGTATTGGTTAGAGATT
Guar-GalT1   (949)   TGGAGGGAGAAGATCTTCTTGGAGAGCGAGTACTACTTCGAAGGGTACTGGCTGGAGATC
Guar-GalT2   (919)   TGGGCGGACAAGATTTACTTAGAAGAACTCGTATTATTTCGAAGGGTACTGGAAGAAATC
Consensus    (961)   TGGACGGAGAAGATCTACTTGGAGAACGAGTATTATTTCGAAGGGTACTGG TAGAGATC
                     1021                                                       1080
Fenugreek    (964)   TCAAAGATGTATGATAAAATGGGTGAGAGATATGATGAGATAGAAAAAGAGTGGAAGGG
Guar-GalT1   (1009)  GTGAAGACGTACGAGAACATAAGCGAGAGGTATGATGAGGTGGAGAGGAAGGTGGAAGGG
Guar-GalT2   (979)   GTCGGAACATTCGAGAATATAAGCAAGAAATACAACGAGATCGAAACGGGGGTGCGCAGG
Consensus    (1021)  GT AAGACGTACGAGAA ATAAGCGAGAGATATGATGAGAT GAAA GAGGGTGGAAGGG
                     1081                                                       1140
Fenugreek    (1024)  TTAAGGAGGAGGCATGCAGAGAAAGTGAGTGAACGTTATGGTGAAATGAGAGAGGAGTAT
Guar-GalT1   (1069)  TTGAGGAGGAGGCATGCGGAAAAGGTCAGCGAGAAATACGGTGCGATGAGGGAGGAGTAT
Guar-GalT2   (1039)  TTAAGAAGGCGTCACGCGGAGAAAGTGAGTGAAGCTTACGGTGAAGAGGGGAGAATAT
Consensus    (1081)  TTAAGGAGGAGGCATGCGGAGAAAGTGAGTGAA  TTACGGTGAAATGAGGGAGGAGTAT
                     1141                                                       1200
Fenugreek    (1084)  GTTAAGAATTTAGGGGATAT-----------GAGAAGACCTTTTATTACACATTTTACA
Guar-GalT1   (1129)  CTGAAGGACA------ACAA-----------GAGGAGGCCTTTTATCACGCACTTTACT
Guar-GalT2   (1099)  TTAACGCGAAGCAGGTAACGGTAAAGGAAGCTGGAGACGGCCGTTTGTGACGCACTTCACG
Consensus    (1141)  T AAGGA AGG ACA           GAGAAGGCC TTTAT ACGCACTTTAC
                     1201                                                       1260
Fenugreek    (1132)  GGGTGCCAACCTTGTAATGGTCATCATAATCCAATATATGCTGCAGATGATTGCTGGAAT
Guar-GalT1   (1171)  GGGTGTCAACCCTGTAATGGCCACCATAATCCTGCTTATAATGGTAATGATTGCTGGAAT
Guar-GalT2   (1159)  GGGTGTCAACCTTGTAGCGGAAATATAACGCTATGTATAACGCCGAAGATTGTTGGAAC
Consensus    (1201)  GGGTGTCAACCTTGTAATGG CA CATAATCCTAT TATAATGC GATGATTGCTGGAAT
                     1261                                                       1320
Fenugreek    (1192)  GGCATGGAGAGAGCTCTCAATTTTGCTGATAATCAGGTGTTGCGCAAGTTTGGTTTCATT
Guar-GalT1   (1231)  GGCATGGAGAGGCTCTTAATTTCGCTGATAATCAAATCTTGCGTACTTACGGTTATCAC
Guar-GalT2   (1219)  GGAATGCGTAAAGCCTTAATTTCGCTGATAATCAGGTGATGCGTAAATATGGTTTCGTA
Consensus    (1261)  GGCATGGAGAGAGCTCTTAATTTCGCTGATAATCAGGTGTTGCGTAA TATGGTTTC T
                     1321                                                       1380
Fenugreek    (1252)  CATCCAAATCTATTGGATAAGTCTGTTTCTCCATTACCATTTGGATA-CCCCGCTGCATC
Guar-GalT1   (1291)  CGTCAAAATTTACTCGACAAGTCTGTTTCACCCTTACCTTTTGGTTA-CCGTGCTGCATA
Guar-GalT2   (1279)  CACCCGGATGTACTAGATAATTCCGTTTCGCCGATTCCGTTTGATTATCCCCGTAACCGG
Consensus    (1321)  CATCCAAAT TACT GATAAGTCTGTTTC CC TTACC TTTGGTTA CCCCGCTGCATC
                     1381                                                       1440
Fenugreek    (1311)  ACCATAAATA-TATTATAACCTGCAGGGGTA--AATTATAATAG-TAATTGTTATGATGA
Guar-GalT1   (1350)  A----TAATG-TACTACTAC-TG----------ATAACGACAG-TTATT-TAAAATTTA
Guar-GalT2   (1339)  TCAGGTAATAATCATATTTAATGGAATCTAATTATTGTTGACCGCTGGCTACTCAGATTC
Consensus    (1381)  AC  TAATA TA TATTAC TG A    A AAT ATGACAG T ATT TTAAGATTA
                     1441                                                       1500
Fenugreek    (1367)  TTCTTCTGTCAATAATAATCAAAATAATGAAGGTGGTGATGATATTAGC----------
Guar-GalT1   (1391)  TTATAC-GAAAAAAAAAAAAAAAAAC-------------------------
Guar-GalT2   (1399)  TCCATGTGTTCTGTAAAGTACTAGTACTACTAGTATTAAATTTCTTAGTGTATATTTTAT
Consensus    (1441)  TTCTTCTGT AA AAAAAATAAAAATAAT    GT T A    T TTAG
```

```
              1501                                                        1560
Fenugreek   (1416) ------------------------------------------------------------
Guar-GalT1  (1418) ------------------------------------------------------------
Guar-GalT2  (1459) AATATTTTTATTGTATATTTTCTGGCGTTTTGCATATATAGTATCGTGTGGAGTAGTATT
Consensus   (1501)
              1561                                                        1620
Fenugreek   (1416) ------------------------------------------------------------
Guar-GalT1  (1418) ------------------------------------------------------------
Guar-GalT2  (1519) TAATTATGCATAAGTGAAGGGATAATTTTATTCTTTTCGAATCCCTAAAAAAAAAAAAA
Consensus   (1561)
              1621           1651
Fenugreek   (1416) -----------------------------
Guar-GalT1  (1418) -----------------------------
Guar-GalT2  (1579) AAAAAAAAAAAAAAAAAAAAAAAAAAACT
Consensus   (1621)
```

```
                       1                                                          60
Fenugreek-GalT    (1)  ATKFG-SKN-KSSPWLSNGCIFLLGAMSALLMIWGLNSFIAPIPNSNPKFNSFITKLKSL
Guar-GalT1        (1)  MAKFG-SRN-KSPKWISNGCCFLLGAFTALLLLWGLCSFIIPIPHTDPKLNSVATSLRSL
Guar-GalT2        (1)  MAKSSNSRNKISHVNLSDGFLFLAGAFSAFLIVWGFSSFTTPIPNETPTPESLSVNSHQN
Consensus         (1)  MAKFG SRN KS  WLSNGCIFLLGAFSALLIIWGL SFI PIPNS PKFNSLST LKSL
                       61                                                         120
Fenugreek-GalT   (59)  NFTTN-TNFAGPDLLHDPSDKTFYDDPETCYTMMDKPMKNWDEKRKEWLFHHPSFAAGAT
Guar-GalT1       (59)  NFPKNPAATLPPNLQHDPPDTFYDDPETSYT-MDKPMKNWDEKRKEWLLHHPSFGAAAR
Guar-GalT2       (61)  DAVSR----GGPDFRFDPPDRTFYDDPEMGYT-IDTTVRDWDAKREEWLRLHPSFAAGAR
Consensus        (61)  NF SN     AGPDL HDPPDKTFYDDPET YT MDKPMKNWDEKRKEWL HHPSFAAGAR
                       121                                                        180
Fenugreek-GalT  (118)  EKIIVITGSQPTKCDNPIGDHLLLRFYKNKVDYCRIHNHDIIYNNALLHPKMDSYWAKYP
Guar-GalT1      (118)  DKILLVTGSQPKRCHNPIGDHLLLRFFKNKVDYCRLHNYDIIYNNALLHPKMNSYWAKYP
Guar-GalT2      (116)  ERVLVVTGSQPAPCRNPIGDHLLLRFFKNKVDYCRLHGYDIVYNNALLHPKMFTYWAKYP
Consensus       (121)  EKILVVTGSQP KC NPIGDHLLLRFFKNKVDYCRLHNYDIIYNNALLHPKM SYWAKYP
                       181                                                        240
Fenugreek-GalT  (178)  MVRAAMLAHPEVEWIWWVDSDAIFTDMEFKLPLWRYKDHNLVIHGWEELVKTEHSWTGLN
Guar-GalT1      (178)  VIRAAMMAHPEVEWVWWVDSDAVFTDMEFKLPIKRYKNHNLVVHGWEGLVRLNHSWTGLN
Guar-GalT2      (176)  VVRAAMMAHPEAEWIWWVDSDALFTDMEVXLPLDHYKDHNLVVHGWAHLIHEKRSWTGLN
Consensus       (181)  VVRAAMMAHPEVEWIWWVDSDAIFTDMEFKLPL RYKDHNLVVHGWE LVK  HSWTGLN
                       241                                                        300
Fenugreek-GalT  (238)  AGVFLMRNCQWSLDFMDVWASMGPNSPEYEKWGERLRETFKTKVVRDSDDQTALAYLIAM
Guar-GalT1      (238)  AGVFLIRNCQWSLEFMDVWVSMGBQTPEYEKWGERLRETFKDKVLPDSDDQTALAYLIAT
Guar-GalT2      (236)  AGVFLIRNCQWSLDFINEWASMGBQTPNYEKWGQTLKSTFKDKFFPESDDQTGLAYLIAI
Consensus       (241)  AGVFLIRNCQWSLDFMDVWASMGPQTPEYEKWGERLRETFKDKVLPDSDDQTALAYLIAI
                       301                                                        360
Fenugreek-GalT  (298)  G-EDKWTKKIYMENEYYFEGYWLEISKMYDKMGERRDEIEKRVEGLRRRHAEKVSERYGE
Guar-GalT1      (298)  DNKDTWREKIFLESEYYFEGYWLEIVKTYENISERMDEVERKVEGLRRRHAEKVSEKYGA
Guar-GalT2      (296)  E-KEKWADKIYLENSYYFEGYWEEIVGTFENISKKYNEIETGVRRLRRRHAEKVSEAYGE
Consensus       (301)  D KDKW DKIYLENEYYFEGYWLEIVKTYENISERYDEIEKKVEGLRRRHAEKVSEKYGE
                       361                                                        420
Fenugreek-GalT  (357)  MREEYVKNLG----DMRRPFITHFTGCQPCNGHHNPIYAADDCWNGMERALNFADNQVLR
Guar-GalT1      (358)  MREEYLKDNK-----RRPFITHFTGCQPCNGHHNPAYNANDCWNGMERALNFADNQILR
Guar-GalT2      (355)  EREKYLTEAGNGKGSWRRPFVTHFTGCQPCSGKYNAMYNAEDCWNGMRKALNFADNQVMR
Consensus       (361)  MREEYLKD G      RRPFITHFTGCQPCNGHHNPIYNADDCWNGMERALNFADNQVLR
                       421                        451
Fenugreek-GalT  (413)  KFGFIHPNLLDKSVSPLPFGYPAASP-----
Guar-GalT1      (412)  TYGYHRQNLLDKSVSPLPFGYPAA-------
Guar-GalT2      (415)  KYGFVHPDVLDNSVSPIPFDYPRNSGNNHI
Consensus       (421)  KYGFIHPNLLDKSVSPLPFGYPAA
```

FIGURE 8

```
                    1                                                          60
AtCesA1      (1)    MEASAGLVAGSYRRNELVRIRHESDGG--TKPLKNMNGQICQICGDDVGLAETGDVFVAC
ZmCesA1      (1)    MAANKGMVAGSHNRNEFVMIRHDGDVPGSAKPTKSANGQVCQICGDSVGVSATGDVFVAC
GhCesA1      (1)    -------------------------------MMESGVPVCHTCGEHVGLNVNGEPFVAC
PtCesA       (1)    -------------------------------MMESGAPICHTCGEQVGHDANGELFVAC
CtManS       (1)    ------------------------------------------------------------
AtCslA9      (1)    ------------------------------------------------------------
AtCslB1      (1)    ------------------------------------------------------------
AtCslC4      (1)    ------------------------------------------------------------
AtCslD1      (1)    ------MASSPPKKTLNSQSSSLSRPPQAVKFGRRTSSGRIVSLSRDDDMDVSGDYSGQN
AtCslE1      (1)    ------------------------------------------------------------
AtCslG1      (1)    ------------------------------------------------------------
Consensus    (1)
                    61                                                         120
AtCesA1     (59)    NECAFPVCRPCYEYERKDGTQCCPQCKTRFRRHRGSPRVEGDEDEDDVDDIENEFNYAQG
ZmCesA1     (61)    NECAFPVCRPCYEYERKEGNQCCPQCKTRYKRQKGSPRVHGDEDEEDVDDLDNEFNYKQG
GhCesA1     (29)    HECNFPICKSCFEYDLKEGRKACLRCGSPY-----------D-ENLLDDVEK-ATGDQS
PtCesA      (29)    HECSYPMCKSCFEFEINEGRKVCLRCGSPY-----------D-ENLLDDVEKKGSGNQS
CtManS       (1)    ------------------------------------------------------------
AtCslA9      (1)    ------------------------------------------------------------
AtCslB1      (1)    ------------------------------------------------------------
AtCslC4      (1)    ------------------------------------------------------------
AtCslD1     (55)    DYINYTVLMPPTPDNQPAGSSGSTSESKGDANRGGG----GGDGPKMGNKLERRLSVMKS
AtCslE1      (1)    ------------------------------------------------------------
AtCslG1      (1)    ------------------------------------------------------------
Consensus   (61)
                    121                                                        180
AtCesA1    (119)    ANKAR---HQRHGEEFSSSSRHESQP-IPLLTHGHTVSGEIRTPDTQSVRTTSGPLGPSD
ZmCesA1    (121)    SGKGPEWQLQGDDADLSSSARHEPHHRIPRLTSGQQISGEIPDASPDRHSIRS--P----
GhCesA1     (75)    TMAAHLN----KSQDVGIHARHIS--------S------VSTLDSEMA-----------
PtCesA      (76)    TMASHLN----DSQDVGIHARHIS--------S------VSTVDSEMN-----------
CtManS       (1)    ------------------------------------------------------------
AtCslA9      (1)    ------------------------------------------------------------
AtCslB1      (1)    ------------------------------------------------------------
AtCslC4      (1)    ------------------------------------------------------------
AtCslD1    (111)    NNKSMLLRSQTGDFDHNRWLFESK-----------------------------------
AtCslE1      (1)    ------------------------------------------------------------
AtCslG1      (1)    ------------------------------------------------------------
Consensus  (121)
                    181                                                        240
AtCesA1    (175)    RNAISSPYIDPRQPVPVRIVDPSKDLNSYGLGNVDWKERVEGWKLKQEKNMLQMTGKYHE
ZmCesA1    (175)    ----TSSYVDPSVPVPVRIVDPSKDLNSYGLNSVDWKERVESWRVKQDKNMMQVTNKYPE
GhCesA1    (105)    ------------------EDN--------GNSIWKNRVESWKEKKNKKKKPATTKVER
PtCesA     (106)    ------------------DEY--------GNPIWKNRVKSCKDKENKKKKRSPKAETE
CtManS       (1)    ------------------------------------------------------------
AtCslA9      (1)    ------------------------------------------------------------
AtCslB1      (1)    ------------------------------------------------------------
AtCslC4      (1)    ------------------------------------------------------------
AtCslD1    (135)    -----------------------GKYGIGNAFWSEEDDTYDGGVSKS-----------
AtCslE1      (1)    ------------------------------------------------------------
AtCslG1      (1)    ------------------------------------------------------------
Consensus  (181)
                    241                                                        300
AtCesA1    (235)    GKGGEIEGTGSNGEELQMADDTRLPMSRVVPISSRLTPYRVVIILRLIILCFFLQYRTT
ZmCesA1    (231)    ARGGDMEGTGSNGEDMQMVDDARLPLSRIVPISSNQLNLYRVVILRLIILCFFFQYRVS
GhCesA1    (137)    EAEIPPEQQ----MEDKPAPDASQPLSTIIPIPKSRLAPYRTVIIMRLIILGLFFHYRVT
PtCesA     (138)    PAQVPTEQQ----MEEKPSAEASEPLSIVYPIPRNKLTPYRAVIIMRLVILGLFFHERIT
CtManS       (1)    ------------------------------------------------------------
AtCslA9      (1)    ------------------------------------------------------------
AtCslB1      (1)    ------------------------------------------------------------
AtCslC4      (1)    ---------MAPNSVAVTMEKPDNFSLLEINGSDPSSFPDKRKSISPKQFSWFLLLKAH
AtCslD1    (159)    ---------------DFLDKPWKPLTRKVQIPAKILSPYRLLIVIRLVIVFFFLWWRIT
AtCslE1      (1)    --------MVNKDDRIRPVHEADGEPLFETRRRTGRVIAYRFFSASVFVCICLIWFYRIG
AtCslG1      (1)    ---------METHRKNSVVGNILHTCHPCRRTIPYRIYAIFHTCGIIALMYHHVH
Consensus  (241)                  D      S      L  YR    II    IL  F    YRI
```

```
              301                                                      360
AtCesA1  (295) HPVKN----AYPLWLTSVICEIWFAFSWLLDQFPKWYPINRETYLDRLAIRYDRDGEP--
ZmCesA1  (291) HPVRD----AYGLWLVSVICEVWFALSWLLDQFPKWYPINRETYLDRLALRYDREGEP--
GhCesA1  (193) NPVDS----AFGLWLTSVICEIWFAFSWVLDQFPKWYPVNRETYIDRLSARYEREGEP--
PtCesA   (194) NPVDS----AFGLWLTSVICEIWFAFSWVLDQFPKWNPVNRETYIERLSARYEREGEP--
CtManS     (1) ------------------------------------------------------------
AtCslA9    (1) ------------------------------------------------------------
AtCslB1    (1) --MNQ----NNSVWVVAFLCESFFSFIWLLITSIKWSPASYKSYPERLDERVH-------
AtCslC4   (51) RLISC----LSWLVSSVKKRIAFSAKNINEEEDPKSRGKQMYRFIKACLVISIIALSI--
AtCslD1  (203) NPNED----AMWLWGLSIVCEIWFAFSWILDILPKLNPINRATDLAALHDKFEQPSPSNP
AtCslE1   (53) EIGDNRTVLDRLIWFVMFIVEIWFGLYWVVTQSSRWNPVWRFPFSDRLSRRYG-------
AtCslG1   (47) SLVTAN---NTLITCLLLLSDIVLAFMWATTTSLRLNPVHRTECPEKYAAKPE-------
Consensus(301)      V        LW   SVICEIWFAF WLLD PKW PVNR TYIDRLA RYE
              361                                                      420
AtCesA1  (349) ---SQLVPVDVFVSTVDPLKEPPLVTANTVLSILSVDYPVDKVACYVSDDGSAMLTFESL
ZmCesA1  (345) ---SQLAPIDVFVSTVDPLKEPPLITANTVLSILSVDYPVDKVSCYVSDDGSAMLTFESL
GhCesA1  (247) ---DELAAVDFFVSTVDPLKEPPLITANTVLSILALDYPVDKVSCYISDDGAAMLTFESL
PtCesA   (248) ---SQLAGVDFFVSTVDPLKEPPLITANTVLSILAVDYPVDKVSCYVSDDGAAMLSFESL
CtManS     (1) ----------MRNLIFEEPEGIPGNSSSSLRYAWQSIRAPVIIPLLKLAVIVCSVMSIM
AtCslA9    (1) ------MELGDTTSVIPDSFMGYRDDITMQMSMVLDQIRAPLIVPALRLGVYICLTMSVM
AtCslB1   (48) ----DLPSVDMFVITADPVREPPILVANTULSILAVNYPANKLACYVSDDGCSPLTYFSL
AtCslC4  (105) ---EIVAHFKKWNLDIINRPSWEVYGLVEWSYMAWLSFRSDYIAPLVISLSRFCTVLFLI
AtCslD1  (259) TGRSDLPGVDVFVSTADPEKEPPLVTANTULSILAVDYPIEKLSAYISDDGGAILTFEAM
AtCslE1  (106) ---SDLPRLDVFVCTADPVIEPPLLVVNTVLSVTALDYPPEKLAVYLSDDGGSELTFYAL
AtCslG1   (97) ----DFPKLDVFICTADPYKEPPMMVVNTALSVMAYEYPSDKISVYVSDDGGSSLTFFAL
Consensus(361)       L  VDVFVSTVDPLKEPPLI ANTVLSILAVDYP DKIS YVSDDG A LTF SL
              421                                                      480
AtCesA1  (406) SETAEFAKKWVPFCKKFNIEPRAPEFYFAQKIDYLKDKIQ--PSFVKERRAMKREYEEFK
ZmCesA1  (402) SETAEFARKWVPFCKKHNIEPRAPEFYFAQKIDYLKDKIQ--PSFVKERRAMKREYEEFK
GhCesA1  (304) VETADFARKWVPFCKKFSIEPRAPEFYFSQKIDYLKDKVQ--PSFVKERRAMKRDYEEYK
PtCesA   (305) VETAEFARKWVPFCKKFSIEPRAPEFYFSQKIDYLKDKVQ--PSFVKERRAMKRDYEEYK
CtManS    (50) LFVERVAMAAVILIVKVLRKKRYTKYNLEAMKQKLERSKK--YPMVLIQIPMYNEKEVYK
AtCslA9   (55) LFVERVYMGIVISLVKLFGRKPDKREKYEPIKDDIELGNSA-YPMVLIQIPMFNEREVYQ
AtCslB1  (104) KEASKFAKIWVPFCKKYNIKVRAPFRYFLNPPAATESS-----EFSKDWEITKREYEKLS
AtCslC4  (162) QSLDRLVLCLGCFWIKFKK----IEPKLTEESIDLEDPSS--FPMVLIQIPMCNEREVXE
AtCslD1  (319) AEAVRFAEYWVPFCRKHDIEPRNPDSYFSIKKDPTKNKKR--QDFVKDRRWIKREYDEFK
AtCslE1  (163) TEAAEFAKTWVPFCKKFNVEPTSPAAYLSSKANCLDSAAE--EVAKLYREMAAR--IETA
AtCslG1  (153) IEAAKFSKQWLPFCKKNNVQDRSPEVYFSSESHSRSDEAENLKTNILKCEVEQMMYEDMK
Consensus(421)    E ARFAK WVPFCKKF IEPRAPEFYFS K D L D         FVKER MKREYEEYK
              481                                                      540
AtCesA1  (464) VRINALVAKAQKIPEEG-----------------------------WTMQDGTPWPGNN
ZmCesA1  (460) VRINALVAKAQKVPEEG-----------------------------WTMADGTAWPGNN
GhCesA1  (362) IRINALVAKAQKTPDEG-----------------------------WTMQDGTSWPGNN
PtCesA   (363) VRVNALVAKAQKTPEEG-----------------------------WTMQDGTPWPGNN
CtManS   (108) LSIGAVCGLSWPADRFI-----------------------------VQVLDDSTNP---
AtCslA9  (114) ISIGAACGLSWPSDRIV-----------------------------IQVLDDSTDP---
AtCslB1  (159) RRVEDATGDSHWLDAED--------------------------------DFEDESNTK
AtCslC4  (216) QSIGAASQLDWPKDRIL-----------------------------IQVLDDSDDP---
AtCslD1  (377) VRINGLPEQIKKRAEQFNMREELKEKRIAREKNGGVLPPDGVEVVKATWMADGTHWPGTW
AtCslE1  (219) ARLGRIPEEARVKYGDG------------------------------FSQWDADA
AtCslG1  (213) SRVEHVVESGKVETAFIT-------------------------CDQFRGVFDLWTDKF
Consensus(481) VRI AL A A    E                                   M D T WPG
              541                                                      600
AtCesA1  (494) TR--------DHPGMIQ-VFLGHSGGLDTDGNE-----------LPRLIYVSREKRPGF
ZmCesA1  (490) PR--------DHPGMIQ-VFLGHSGGLDTDGNE-----------LPRLVYVSREKRPGF
GhCesA1  (392) PR--------DHPGMIQ-VFLGYSGARDIEGNE-----------LPRLVYVSREKRPGY
PtCesA   (393) TR--------DHPGHDSGLPWEILGARDIEGNE-----------LPRLVYVSREKRPGY
CtManS   (135) --------------VLRELVEMECQKWIQKG-------------V-NVKYENRRNRNGY
AtCslA9  (141) --------------TIKDLVEMECSRWASKG-------------VNIKYEIRDNRNGY
AtCslB1  (185) PN--------DHSTIVK-VVWENKGGVGVEN-------------EVPHFVYISREKRPNY
AtCslC4  (243) --------------NLQLLIKEEVSVWAEKG-------------V-NIIYRHRLIRTGY
AtCslD1  (437) FEPKPDHSKGDHAGILQIMSKVPDLEPVMGGPNEGALDFTGIDIRVPMFAYVSREKRPGF
AtCslE1  (244) TRR-------NHGTILQVLVDGREG----------N-----TIAIPTLVYISREKRPQH
AtCslG1  (246) SR--------HDHPTIIQVLQNSETD---MDNTR--------KYIMPNLIYVSREKSKVS
Consensus(541)  R        DH   IIQ L    G        DG          LP LVYVSREKRPGY
```

```
              601                                                           660
AtCesA1   (533) QHHKKAGAMNALIRVSAVLTNGAYLLNVDCDHYFNNSKAIKEAMCFMMDPA-IGKKCCYV
ZmCesA1   (529) QHHKKAGAMNALIRVSAVLTNGAYLLNVDCDHYFNSSKALREAMCFMMDPA-LGRKTCYV
GhCesA1   (431) QHHKKAGAENALVRVSAVLTNAPFILNLDCDHYVNNSKAVREAMCFLMDPQ-VGRDVCYV
PtCesA    (433) QHHKKAGAENALVRVSAVLTNAPYILNVDCDHYVNNSKAVREAMCILMDPQ-VGRDVCYV
CtManS    (166) KAGALKEGLEKQY-----VEDCEFVAIFDADFQPDADFLWNTIPYLLENPK-LGLVQARW
AtCslA9   (172) KAGALKEGMKKSY-----VKSCDYVAIFDADFQPEADFLWRTVPYLLHNPK-LALVQARW
AtCslB1   (223) LHHYKAGAMNFLVRVSGLMTNAPYMLNVDCDMYANEADVVRQAMCIFLQKSMNSNHCAEV
AtCslC4   (274) KAGNLKSAMTCDY-----VKDYEFVTIFDADFTPNPDFLKKTVPHFKGNPE-LGLVQARW
AtCslD1   (497) DHNKKAGAMNGMVRASAILSNGAFILNLDCDHYIYNSKAIKEGMCFMMDR--GGDRICYI
AtCslE1   (281) HHNFKAGAMNALLRVSSKITCGKIILNLDCDMYANNSKSTRDALCILLDEK-EGKEIAEV
AtCslG1   (287) PHHFKAGALNTLLRVSGVMTNSPILLTLDCDMYSNDPATLVRALCVLTDP-EIKSGLGYV
Consensus (601)     HH KAGAMNALVRVSAVLTNG YILNLDCD Y N SKAVREAMCFLMDP  LG   AYV
              661                                                           720
AtCesA1   (592) QFPQRFDGIDLHDRYANRNIVFFDINMKGLDGIQGPVYVGTGCCFNRQALYGYDPVLTEE
ZmCesA1   (588) QFPQRFDGIDLHDRYANRNIVFFDINMKGLDGIQGPVYVGTGCCFNRQALYGYDPVLTEA
GhCesA1   (490) QFPQRFDGIDRSDRYANRNTVFFDVNMKGLDGIQGPVYVGTGCVFNRQALYGYGPPSMPS
PtCesA    (492) QFPQRFDGIDKSDRYANRNVVFFDVNMKGLDGIQGPVYVGTGCVFNRQALYGYGPPSMPS
CtManS    (220) KFVNSEECMMTRLQEMSLDYHFSVEQEVGSSTYSFFGFNGTAGVWRIQAIKDAG------
AtCslA9   (226) KFVNSDECLMTRMQEMSLDYHFTVEQEVGSSTYAFFGFNGTAGIWRISALNEAG------
AtCslB1   (283) QFPQEF---Y--DSNADELTVLQSYLGRGTAGIQGPTYAGSGCFHTRRVMYGLS------
AtCslC4   (328) SFVNKDENLLTRLQNINLCFHFEVEQQVNGVFLNFFGFNGTAGVWRIKALEESG------
AtCslD1   (555) QFPQRFEGIDPSDRYANHNTVFFDGNMRALDGLQGPVYVGTGCMFRRYALYGFNPP---R
AtCslE1   (340) QFPQCFDNVTRNDLYGSMMRVGIDVEFLGLDGNGGPLYIGTGCFHRRDVICGRKYG----
AtCslG1   (346) QFPQKFLGISKNDIYACENKRLFIINMVGFDGLMGPTHVGTGCFFNRRAFYGPP------
Consensus (661) QFPQRFDGI   D YAN N VFFDINMKGLDGIQGPVYVGTGCVF R ALYG
              721                                                           780
AtCesA1   (652) DLEP---NIIVKSCCGSRKKGKSSKKYNYEKRRGINRSDSNAPLFNMEDIDEGFEGYDDE
ZmCesA1   (648) DLEP---NIVIKSCCGRRKK--KNKSYMDSQSRIMKRTESSAPIFNMEDIEEGIEGYEDE
GhCesA1   (550) FPK--SSSSSCSCCCPGKKE----PKDPSELYRDAKREELDAAIFNLREIDN---YDEYE
PtCesA    (552) LRKRKDSSSCFSCCCPSKKKP---AQDPAEVYRDAKREDLNAAIFNLTEIDN---YDEHE
CtManS    (274) ------------------------------------------------------------
AtCslA9   (280) ------------------------------------------------------------
AtCslB1   (332) ---------------------------------------------IDDLEDDGSLSSLA
AtCslC4   (382) ------------------------------------------------------------
AtCslD1   (612) -------ANEYSGVFGQEKAPAMHVRTQSQASQTSQASDLESDTQPLNDDPDLGLPKKFG
AtCslE1   (396) ------------------------------------------------------------
AtCslG1   (400) ----------------------------------------------------------YM
Consensus (721)                                                         L  D
              781                                                           840
AtCesA1   (709) RSILMSQRSVEKRFGQSPVFIAATFMEQGG-----IPPTTNPATLLKEAIHVISCGYEDK
ZmCesA1   (703) RSVLMSQRKLEKRFGQSPIFIASTFMTQGG-----IPPSTNPASLLKEAIHVISCGYEDK
GhCesA1   (601) RSMLISQTSFEKTEGLSSVFIESTLMENGG-----VAESANPSTLIKEAIHVISCGYEEK
PtCesA    (606) RSMLISQLSFEKTEGLSSVFIESTLMENGG-----VPESANSPPFIKEAIQVIGCGYEEK
CtManS    (274) -----------------------------------G------------------------
AtCslA9   (280) ------------------------------------------------------------
AtCslB1   (346) TRKYLAEENLAREFGNSNEMVTSVVEALQRK----PNPQNTLANSIEAAQEVGHCHEEYQ
AtCslC4   (382) -----------------------------------G------------------------
AtCslD1   (665) NSTMFTDTIPVAEYQGRPLADHMSVKNGRPPGALLLPRPPLDAPTVAEAIAVISCWYEDN
AtCslE1   (396) ------EEEEEEE--------------------SERIHENLEPEMIKALASCTYEEN
AtCslG1   (402) LILPEIN--ELKPYR------------------IADKSIKAQDVLSLAHNVAGCIYEYN
Consensus (781)       K F                                  L  A V   C YED
              841                                                           900
AtCesA1   (764) TEWGKEIGWIYGSVTEDILTGFKMHARGHISIYCNPPRPAFKGSABINLSDRLNQVLRWA
ZmCesA1   (758) TEWGKEIGWIYGSVTEDILTGFKMHAPGWQSIYCMPPRPCFKGSABINLSDRLNQVLRWA
GhCesA1   (656) TAWGKEIGWIYGSVTEDILTGFKMHCRWRSIYCMPLRPAFKGSABINLSDRLHQVLRWA
PtCesA    (661) TEWGKQIGWIYGSVTEDILSGFKMHCRWRSIYCMPVRPAFKGSABINLSDRLHQVLRWA
CtManS    (275) --------WKDRTTVEDMDLAVRASLHGWEFVFVG--DVKVKNELHSTFKAYRFQQHRWS
AtCslA9   (280) --------GWKDRTTVEDMDLAVRASLKGWKFLYLG--SLKVKNELHSTFKAYRYQQHRWS
AtCslB1   (402) TSWGKTIGWLYESTAEDANTSIGIHSRGWTSSYISPKPPAFLGAMPPGGPEAMLQQRRWA
AtCslC4   (383) ---------WLERTTVEDMDIAVRAHLNGWKFIYLN--DVEVTCELPESYEAYKKQQHRWH
AtCslD1   (725) TEWGDRIGWIYGSVTEDVVTGYRMHNRGWRSVYCITKRDAFRGTABINLTDRLHQVLRWA
AtCslE1   (427) TQWGKEMGVKYGCPVEDVITGLTIQCRGWKSAYLNPEKQAFLGVABTNLHQMLVQQRRWS
AtCslG1   (441) TNWGSKIGFRYGSLVEDYYTGFMLHCEGWRSVFCNPKKAAFYGDSPKCLVDLVGQQIRWA
Consensus (841) T WGK IGWIYGSV EDILTGFKMH RGWRSIYC P R AFKG AP NL D L QQLRWA
```

```
                901                                                          960
AtCesA1   (824) LGSTEILLSRHCPIWYGYHG-RLRLLERIAYINTIVYPITSIPLIAYCILPAFCLITDRF
ZmCesA1   (818) LGSVEILLSRHCPIWYGYNG-RLKLLERLAYINTIVYPITSIPLIAYCVLPAICLLTNKF
GhCesA1   (716) LGSVEIFLSRHCPLWYGFGGGRLKWLQRLAYINTIVYPFTSLPLIAYCSLPAICLLTGKF
PtCesA    (721) LGSVEIFFSRHCPLWYGFGGGRLKWLQRLAYINTIVYPFTSLPLIAYCTIPAVCLLTGKF
CtManS    (325) CGPANLFKKMTKEIICCKR-----VPLLKRLHLIYAFFFVRKIVAHWVTFFFYCIVIPAC
AtCslA9   (331) CGPANLFRKMAFEIMTNKN-----VTLWKKVHVIYSFFVVRKLVAHIVTFIFYCVLPAT
AtCslB1   (462) TGLLEVLFNKQSPLIGMFCR-KIRFRQSLAYLYIFTWGLRSIPELIYCLLPAYCLLHNAA
AtCslC4   (433) SGPMQLFRLCLPSIIKSK-----ISVWKKANLIFLFFLLRKLILPFYSFTLFCIILPLT
AtCslD1   (785) TGSVEIFFSKNNAMFATR---RLKFLQRVAYLNVGIYPFTSIFLVVYCFLPALCLFSGKF
AtCslE1   (487) EGDFQIMLSKYSPVWYGKG--KISLGLILGYCCYCLWAPSSLPVLIYSVLTSICLFKGIP
AtCslG1   (501) VGLFEMSFSKYSPITYGIKS--LDLLMGLGYCNSPFKPFWSIPLTVYGLLPQLALISGVS
Consensus (901)   G VEIF SKH PIWYG    RLKLL  LAYIN   VYP TSIPLI YC LPALCLIT
                961                                                         1020
AtCesA1   (883) IIPEISNYASIWFILLFISIAVTGILELRWSGVSIEDWWRNEQFWVIGGTSAHLFAVFQG
ZmCesA1   (877) IIPEISNYAGMFFILLFASIFATGILELRWSGVGIEDWWRNEQFWVIGGTSAHLFAVFQG
GhCesA1   (776) IIPTLSNLASVLFLGLFLSIIVTAVLELRWSGVSIEDLWRNEQFWVIGGVSAHLFAVFQG
PtCesA    (781) IIPTLSNLASMLFLGLFISIIVTAVLELRWSGVSIEDLWRNEQFWVIGGVSAHLFAVFQG
CtManS    (380) VIVPEVNLKKQIALYIPATIITLLNAVSTPRSMHLLVLWILFENVMSLHRTKAATIGLLE-
AtCslA9   (386) VLVPEVTVPKWGAVYTPSVITLLNAVGTPRSLHLMVFWILFENVMSLHRTKATFIGLLE-
AtCslB1   (521) LFP--KGVYLGIVVTLVGMHCLYSLWEFMSLGFSVQSWFASQSFWRIKTTCGWLFSTPDI
AtCslC4   (487) MFIPEAELPLWIICYVPLFISLLNILPSPKSFPFIVPYLLFENTMSITKFNAMISGLFQ-
AtCslD1   (842) IVQSLDIHFLSYLLCITVTLTLISLLEVKWSGIGLEEWWRNEQFWLIGGTSAHLAAVVQG
AtCslE1   (545) LFPKVSSSWFIPFGVYTVAATAYSIAEFLWCGGTFRGWWNEQRMWLYRRTSSFLFGFMDT
AtCslG1   (559) VFPKASDPWFWLYIILFFGAYAQDLSDFLLEGGIYRKWWNDQRMLMIKGLSSFFFGFIEF
Consensus (961) IIP LS L      IFI L ISI L  LLE  WSG SI   WW  EQFWVI GTSA LFAV Q
                1021                                                        1080
AtCesA1   (943) ILKVLAGIDTNFTVTSKATDE--DGDFAEL--------------YIFKWTALLIPPTTVL
ZmCesA1   (937) ILKVLAGIDTNFTVTSKASDE--DGDFAEL--------------YVFKWTSLLIPPTTVL
GhCesA1   (836) FLKMLAGIDTNFTVTAKAA-D--DADFGEL--------------YIVKWTTLLIPPTTLL
PtCesA    (841) FLKMLAGIDTNFTVTAKAA-E--DAEFGEL--------------YMVKWTTLLIPPTTLL
CtManS    (439) ----AN-RVNEWVVTEKLG-----NA------------------MKQRNNARPS----
AtCslA9   (445) -----GGRVNEWIVTEKLG---------------------DVKAKSATKT-
AtCslB1   (579) ILKLLGISKTVFIVILKKTMPKTMSGSGSEKSQREVDCPNQDSGKFEFDGSLYFLPGTFIL
AtCslC4   (546) ----FG-SAYEWVVEKKTG-----RS------------------SESDLLAFAEKEEK
AtCslD1   (902) ILKVIAGIEISFTLTSKASGEDEDDIFADL--------------YIVKWTGLFIMPLTII
AtCslE1   (605) IKKLLGVSESAFVITAKVAEEEAAERYKEEVMEFG---------VESPMFLVLGTLG
AtCslG1   (619) ILKTLNLSTPKFNVTSKANDDDEQRKRYEQEIFDFG---------TSSSMFLPLTTVA
Consensus (1021) ILKVLAG DT F VTSKAA E      F E             Y  KTL IP TTLL
                1081                                                        1140
AtCesA1   (987) LVNLIGIVAGVSYAVNSGYQSWGPLFGKLFFALWVIAHLYPFLKGLLGRQNR--------
ZmCesA1   (981) VINLVGMVAGISYAINSGYQSWGPLFGKLFFSIWVILHLYPFLKGLMGRQNR--------
GhCesA1   (879) IVNMVGVVAGFSDALNKGYEAWGPLFGKVFFSFWVILHLYPFLKGLMGRQNR--------
PtCesA    (884) IINMSG-CAGFSDALNKGYEAWGPLFGKVFFAFWVILHLYPFLKGLMGRQNL--------
CtManS    (465) ------------------------------------RASRFRIIERIH---------
AtCslA9   (469) ----------------S-----------------K---KVIRFRFGDRIHV--------
AtCslB1   (639) LVN-LAALAGCSVGLQRHGG-GSGLAEACGCILVVILFLPFLKGMFEKGK---------
AtCslC4   (576) LHRRNS--ESGLELLSKLKEQETNLVGQETVKKSLGGLMRPKNKKKTNMVF---------
AtCslD1   (948) IVNLVAIVIGASRTIYSVIPQWGKLMGGIFFSLWVLTHMYPFAKGLMGRRGK-------
AtCslE1   (653) MLNLFCFAAAVARLVSGDGGDLKTMGMQFVITGVLVVINWPLYKGMLLRQDK-------G
AtCslG1   (668) IVNLLAFVWGLYGILFCG----GELYLELMLVSFAVVNCLPIYGAMVLRKDDGKLSKRTC
Consensus (1081) IVNLVG VAG S  L      G LGL     WVIL LYPF KGLM R
                1141                                                        1192
AtCesA1   (1039) -TPTIVIVWSVLLASIESLLWVRINPFVDANPNANNFNGKGGVF--------
ZmCesA1   (1033) -TPTIVIVWSLLLASIESLLWVKIDPFISPTQKAAALGQCGVNC--------
GhCesA1   (931)  -TPTIVVLWSVLLASVESLVWVRINPFVSTADSTTVSQSCISDC-------
PtCesA    (935)  -TPTIVVLWSVLLASVFSLVWVKINPFVNKVDNTLVAETCISIDC------
CtManS    (477)  -PLEIIVGMYMLHCATYDLLFGHDHFFVYLLLQAGAFFTMGFGLVGTIVPT-
AtCslA9   (484)  --LELGVGMYLLFVGCVDAFFGKNHYYLYLFAQAIAFFIAGFGQIGTIVPNH
AtCslB1   (688)  ----YGIPWSTLSKAAFLAVLFVVFSVGN--------------------
AtCslC4   (625)  -KKELGLAFLLLTAAARSFLSAHGLHFYFLLFQGLSFLVVGLDLIGEQIS--
AtCslD1   (1000) -VPTIVYVWSGLVSITVSLLWITISPPDDVSGSGGISV------------
AtCslE1   (706)  KMPMSVTVKSVVLALSACTCLAFL------------------------
AtCslG1   (724)  FLAGNLHVGSYCVKLLRPQVTSPLRLIHNNNTSGWFKRKKHNMNESV-----
Consensus (1141)   P IVVVWSVLLAS FSLLW  I    FV        A
```

Soy-transformation vector
11525

A   B   C
  
FIGURE 17

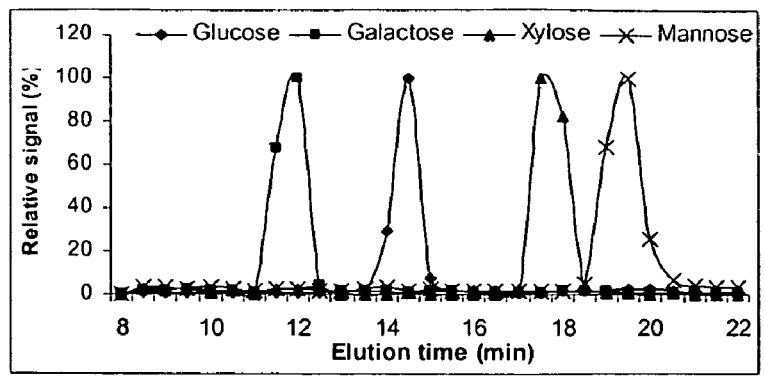
FIGURE 20A
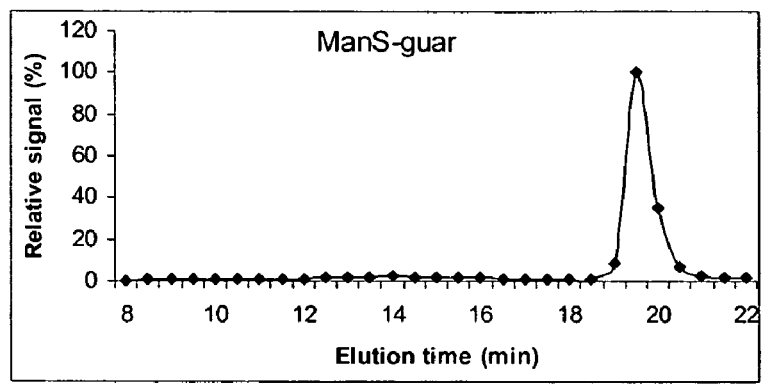
FIGURE 20B
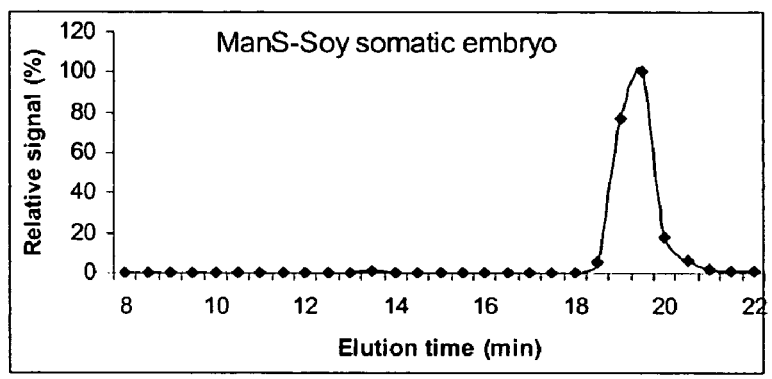
FIGURE 20C
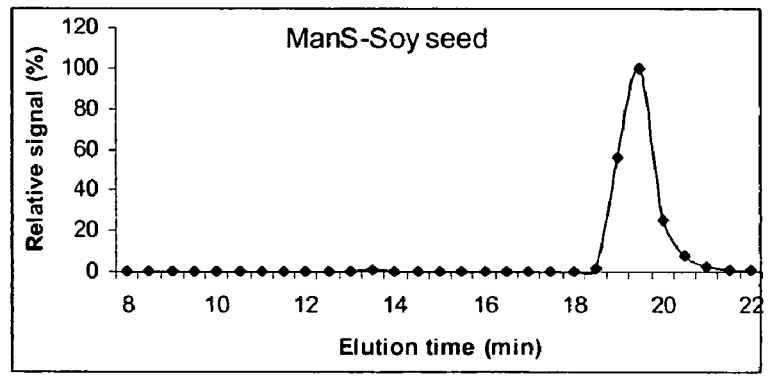
FIGURE 20D
FIGURE 20

>CtGonsT 1349 bp.
GGTGATGCAAATCGCATGAGAGGGGAAGAAGAGGTGTCTCACTTACTCTTCAATCTTCAT
TCACCCTTACGAGTGCCACCTCTCTTCTCTCCTTCTCTTCACAGCTCAAACAATTTGCTG
TTAAACTTTGATCGGTTCATCCATGGAAGAAACCTTCGTTTTCCAGTGGAGCGTTATCAG
ATCTCTCTTGTCCATCCTTCAGTGGTGGGCTTTCAATGTCACCGTTATCATCGTTAACAA
GTGGATCTTCCAGAAATTGGATTTCAAGTTTCCCCTTTCAGTATCCTGTGTACACTTTAT
CTGCTCAGCAATTGGAGCATATATCGTGATTAAGGTGCTGAAGCTTAAACCACTGATAAC
TGTTGACCCTGATGATCGCTGGAGAAGAATATTTCCTATGTCATTTGTATTCTGTATTAA
CATAGTGCTGGGGAATGTGAGCCTACGGTATATTCCAGTTTCTTTTATGCAGACGATAAA
GTCATTCACGCCTGCAACTACAGTTGTTCTGCAATGGCTTGTATGGAGAAAGTATTTTGA
CTGGCGTATTTGGGCTTCTCTTATTCCCATTGTTGGAGGGATTCTTCTTACATCTGTAAC
AGAGCTTAGTTTTAATATGTTTGGATTTTGTGCTGCCTTATTTGGTTGTTTGGCCACATC
TACGAAGACTATCCTTGCAGAATCTCTTTTGCATGGATACAAATTTGATAGCATAAACAC
AGTTTACTACATGGCACCCTTTGCAACCATGATCTTGGCGCTTCCTGCCATGTTACTCGA
AGGAAATGGAATTCTTGACTGGCTAAACACTCATCCATATCCTTGGTCAGCCCTCATCAT
TATTTCAGCTCTGGGGTTTTGGCTTTCTGTCTCAACTTCTCCATTTTTTACGTGATTCA
CTCCACCACTGCTGTAACCTTTAACGTTGCCGGAAACCTTAAGGTTGCAGTTGCTGTTCT
GGTTTCATGGCTGATATTTAGGAACCCAATATCATACTTAAATGCAGTTGGATGTGCCGT
GACACTTGTGGGATGTACATTCTATGGTTATGTAAGGCACATGCTCTCCCAACAGCCACC
AGTTCCAGGAACTCCTCGAACTCCAAGGACCCCTCGCAGTAAGATGGAGTTACTCCCTCT
TGTAAATGATAAATTAGAAGATAAGGTCTAATTGTTTTAGCTATGTACACGAGGTTTATG
TCATTTCTAAGGCAGTAGTAACAGCAATATAGGTACAAAAGGATTACAGTGACTGGTTAT
TTATTCCGTTAGATTATCCCAAAATTTTCAATACAAGTTCTTTTACATTCCCTTTTTAAA
AAAAAAAAAAAAAAAAAAAAAAAAAAAA

FIGURE 21

\>CtGONST 0aa, 342 aa.

MEETFVFQWSVIRSLLSILQWWAFNVTVIIVNKWIFQKLDFKFPLSVSCVHFICSAIGAY
IVIKVLKLKPLITVDPDDRWRRIFPMSFVFCINIVLGNVSLRYIPVSFMQTIKSFTPATT
VVLQWLVWRKYFDWRIWASLIPIVGGILLTSVTELSFNMFGFCAALFGCLATSTKTILAE
SLLHGYKFDSINTVYYMAPFATMILALPAMLLEGNGILDWLNTHPYPWSALIIIFSSGVL
AFCLNFSIFYVIHSTTAVTFNVAGNLKVAVAVLVSWLIFRNPISYLNAVGCAVTLVGCTF
YGYVRHMLSQQPPVPGTPRTPRTPRSKMELLPLVNDKLEDKV

FIGURE 22

```
                   1                                                          50
    CtGONST    (1) ------------------------MEETFVFQWSVIR--------------
   AtGONST5    (1) -----------------------MEEGSLWRQWTMFR--------------
   AtGONST4    (1) ------------------------MSSSRFDS-------------------
   AtGONST3    (1) ------------------------MSTNDEENGTVIEVKN--VPEP--SPE
   AtGONST2    (1) MSAVKLEAIVCHEPDESELSHLSDNGSKTKNGVVFQLLDQKSSEHRWFSE
   AtGONST1    (1) -----------------MKLYEHDGVDLEDGKTVKSGG---DKP--IPR
   Consensus   (1)                         MEGS   ENGTVIR
                   51                                                        100
    CtGONST   (14) -------------------------SLLSILQWWAFNVTVIIVNKWIF
   AtGONST5   (15) -------------------------SLLSILQWWGFNVTVIIMNKWIF
   AtGONST4    (9) -----------------------NKQLTTSSLVIGYALCSSLLAVINKLAI
   AtGONST3   (24) TWYS---------------VFLRQASVYGVAAGYCLSASLLSIINKWAI
   AtGONST2   (51) RFLRWRRRYLPVDGDNRRDHGSVKQSGPLVSGAAYCISSCSMIILNKIVL
   AtGONST1   (28) KIH-------------NR--------ALLSGLAYCISSCSMILVNKFVL
   Consensus  (51)                         KQ  SLLSILAYCISS SLIIINKWII
                   101                                                       150
    CtGONST   (37) QKLDFKFPLSVSCVHFICSAIGAYIVIKVLKIKPLITVDPDDRWRRIFPM
   AtGONST5   (38) QKLDFKFPLSVSCVHFICSSIGAYIVIKVLKIKPLIVVDPEDRWRRIFPM
   AtGONST4   (37) IYFNYPG--LLTALQYLTCTVAVYLLGKSGLIN--HDPFTWDTAKKFLPA
   AtGONST3   (58) MKEPYPG--ALTAMQYFTSAAGVLLCAQMKLIE--HDSLNLLTMWRFLPA
   AtGONST2  (101) SSYNFNAGVSLMLYQNLISCLVVAVLDISGVVS--VEKFNWKLIRVWMPV
   AtGONST1   (56) SSYNFNAGIFLMLYQNFVSVIIVVGLSLMGLIT--TEPLTLRLMKVWFPV
   Consensus (101) SKFNF A LSLS VQFI SAIGVYIL KMGLI    ID    D MRRFFPM
                   151                                                       200
    CtGONST   (87) SFVFCINIVLGNVSLRYIPVSFMQTIKSFTPATTVVLQWLVWRK-YFDWR
   AtGONST5   (88) SFVFCINIVLGNISLRYIPVSFMQTIKSLTPATTVVLQWLVWRK-YFDWR
   AtGONST4   (83) AIVFYLAIFTNTNLLRHANVDTFIVFRSLTPLLVAIADTVFRSQPLPSRL
   AtGONST3  (104) AMIFYLSLFTNSELLLHANVDTFIVFRSAVPIFVAIGETLFLHQPWPSVK
   AtGONST2  (149) NVIFVGMLVSGMYSLKYINVAMVTILKNATNILTGIGEVYMFRK-RQNNK
   AtGONST1  (104) NVIFVGMLITSMFSLKYINVAMVTVLKNVTNVITAVGEMYLFNK-QHDNR
   Consensus (151) AVIF I IVTG  SLRYINVA M VIKSLTPILTAIGE LVFRK Y D R
                   201                                                       250
    CtGONST  (136) IWASLIPIVGGILLTSVTELSENMFGFCAALFG-------CLATSTKTIL
   AtGONST5  (137) IWASLVPIVGGILLTSITELSFNVFGFCAALFG-------CLATSTKTIL
   AtGONST4  (133) TFLSLVVILAGAVGYVAIDSSFTLTAYSWALA-------YLVTITTEMVY
   AtGONST3  (154) TWGSLATIFGGSLLYVFIDYQFTIAAYSWALA-------YLVSMTIDFVY
   AtGONST2  (198) VWAAMFMMIISAISGGIIDLTFDAVGYIWQLANCFLTASYSLTLRRVMDK
   AtGONST1  (153) VWAALFLMIISAVSGGIIDLSFNAVGYAWQIANCFLTASYSLTLRKTMDT
   Consensus (201) IWASLVLIIGGALL   ITDLSFNI GYSWALA       Y LTLST MI
                   251                                                       300
    CtGONST  (179) AESLLHGYKFDSINTVYYMAPFATMILALPAMLLEGNGILDWLNTHPYP-
   AtGONST5  (180) AESLLHGYKFDSINTVYYMAPFATMILGLPAFLLERNGILDWFEAHPSP-
   AtGONST4  (176) IKHMVSNIKLNIWGLVLYNNLLSLMIAPVFWFLTGEFTEVFAALSENRGN
   AtGONST3  (197) IKHVVMTIGLNTWGLVLYNNLEALLLFPLELLIMGELKKIKHEITDET-D
   AtGONST2  (248) AKQSTKSGSLNEVSMVLLNNLLSIPFGITLIILLGEWRYVISTDVTKD--
   AtGONST1  (203) AKQVTQSGNLNEFSMVLLNNTLSLPLGLLLSYFFNEMDYLYQTPLLRL--
   Consensus (251) AK LL S KLNSW LVLYNNLLALMIG L ALLLGE    L     T
```

FIGURE 23a (1 of 2)

```
              301                                                350
   CtGONST  (228) ---WSALIIIFSSGVLAFCLNFSIFYVIHSTTAVTFNVAGNLKVAVAVLV
   AtGONST5 (229) ---WSALIILFNSGVLAFCLNFSIFYVIQSTTAVTFNVAGNLKVAVAVFV
   AtGONST4 (226) LFEPYAFSSVAASCVFGFLISYFGFAARNAISATAFTVTGVVNKFLTVVI
   AtGONST3 (246) WYSLQVVLPVGLSCLFGLAISFFGFSCRRAISATGFTVLGIVNKLLTVVI
   AtGONST2 (296) ---SMFWVVATASGFLGLAISFTSMWFLHQTGPTTYSLVGSLNKVPISLA
   AtGONST1 (251) ---PSFWMVMTLSGLLGLAISFTSMWFLHQTGATTYSLVGSLNKIPLSIA
   Consensus (301)      SAWIIV ASGVLGLAISFS  FW IHATSATTFSVVG LNKIL VLI
              351                                         400
   CtGONST  (275) SWLIFRNPISYLNAVGCAVTLVGCTFYGYVRHMLSQQPPVPGTPRTPRTP
   AtGONST5 (276) SWMIFRNPISPMNAVGCGITLVGCTFYGYVRHMLSQQQ--PGTPRTPRTP
   AtGONST4 (276) NVLIWDKHATPVGLVCLLFTICGGVGYQQSVKLDKPIEKVSEKDSEKGEE
   AtGONST3 (296) NLMVWDKHSTFVGTLGLLVCMFGGVMYQQSTLK-KPNATQEAKPQEQDEE
   AtGONST2 (343) GLVLFNVPLSLPNLFSILFGLFAGVVFARAKMS-----------------
   AtGONST1 (298) GIVLFNVPTSLQNSASILFGLVAGVVFARAKMREKS--------------
   Consensus (351)      LLIF  PIS VNAVGILFTLVGGVVYA AKMM K Q    G P
              401               430
   CtGONST  (325) RSKMELLPLVNDKLEDKV------------
   AtGONST5 (324) RNKMELIPLVNDKLESKI------------
   AtGONST4 (326) DE--ELTQLVPGKLASVV------------
   AtGONST3 (345) QE--KLLEMQENKESNSVDIKETLKSEEKL
   AtGONST2 (376) ------------------------------
   AtGONST1 (334) ------------------------------
   Consensus (401)       ELL LV   KL   V
```

FIGURE 23b (2 of 2)

| | CtGONST | AtGONST5 | AtGONST4 | AtGONST3 | AtGONST2 | AtGONST1 |
|---|---|---|---|---|---|---|
| CtGONST | 100 | 90 | 31 | 24 | 16 | 28 |
| AtGONST5 | | 100 | 31 | 22 | 17 | 28 |
| AtGONST4 | | | 100 | 51 | 19 | 28 |
| AtGONST3 | | | | 100 | 17 | 26 |
| AtGONST2 | | | | | 100 | 59 |
| AtGONST1 | | | | | | 100 |

FIGURE 24

SEQUENCE LISTING

<160> NUMBER OF SEQ ID NOS: 10

<210> SEQ ID NO 1
<211> LENGTH: 1964
<212> TYPE: DNA
<213> ORGANISM: Cyamopsis tetragonoloba

<400> SEQUENCE: 1

```
ggaattcggc acgaggtgcc tgcaacaagt cactagtcca tcctgcagtt ccctaaccct      60
ccctagtgtc tttctcttca ggctccatat tcctttataa ctactacaat agatacaatg     120
agaaacctaa tcttcgagga gcctgaaggg attccaggca acagttcaag cagtctgcgc     180
tatgcctggc aatcaattcg tgccccagtg atcataccatc ttctaaaact agcagtcata     240
gtgtgctcag ttatgtcaat catgctattt gttgaaagag tagccatggc agctgtaatt     300
ttgattgtca aagtgctgag gaagaaaaga taccaccaagt ataacttgga agccatgaaa     360
cagaagctag agagaagcaa aaaatacccc atggtgctga tccaaatacc tatgtataac     420
gagaaagagg tgtacaagct ttccattgga gcagtatgtg ggctttcatg gccagctgac     480
aggttcatag ttcaagttct tgatgactca acaaatccag tcttaaggga gttggttgaa     540
atggagtgtc aaaaatggat acagaaaggt gtgaatgtca agtatgaaaa taggagaaat     600
cgcaatggtt acaaagcagg tgccttaaaa gagggtttgg agaagcaata tgtagaggat     660
tgtgagtttg tagcaatatt tgatgcagat ttccaaccag atgcggattt tctttggaac     720
acaattcctt atctgctgga aaatccaaag ttgggtttgg ttcaggcgag atggaaattt     780
gtgaactcag aagaatgtat gatgacacgg cttcaagaga tgtcactaga ttaccacttt     840
agtgttgaac aggaagtcgg ctcttcaaca tactcattct tcggtttcaa tggaacagca     900
ggagtttggc ggatccaagc cataaaagat gctggaggat ggaaagaccg aacaacggtg     960
gaggatatgg accttgcagt tagagcaagc ttgcatggct gggaatttgt ttttgtgggt    1020
gatgtaaagg tcaaaaatga attaccaagt acatttaaag catatcgatt tcagcagcac    1080
aggtggtcat gcggtccagc taatctcttt aagaaaatga ccaaggaaat catctgttgc    1140
aaaagggtgc cacttctcaa gagactccat ctcatctatg ctttcttctt tgtgagaaaa    1200
atagttgcac actgggttac gttcttcttt tactgcatag ttataccagc ttgtgtgata    1260
```

-continued

```
gttcccgaag ttaatctcaa aaagcagatt gccatataca tcccagcaac cattacaatt    1320
ctaaatgcag tctccacccc aagatccatg catctactag tactctggat actctttgag    1380
aatgtcatgt cactccatcg aactaaagca gcaattattg gactcttgga agcaaatcgt    1440
gtcaatgaat gggttgtgac tgagaagctt ggaaatgcca tgaaacagag gaacaatgct    1500
aggccatcaa gagcttcacg gtttcgaatt atagaaagga tccacccatt ggagattata    1560
gtggggatgt atatgctgca ctgtgcaacc tatgacctgt tattcggaca cgaccatttc    1620
tttgtctatc ttctgttgca ggcaggggcg ttctttacaa tgggatttgg cctagtagga    1680
acaattgtac ccacctaaag cttaaggtc atggactcat gaacataagt attagtgtat    1740
gaacgggtcc tgtttgtttt aagactctaa gtctagtgaa ctagctatcc ataagcatag    1800
aactgtaaga gaagctacgg ctacttagta gaagcattcc atatggtatc aggacttctt    1860
tgtacccatg tataagaacc agaatcaaaa cgtataaaca tgtccataat atgaagctta    1920
aataaatctg ttatctgcac taaaaaaaaa aaaaaaaaaa aaac                     1964
```

<210> SEQ ID NO 2
<211> LENGTH: 526
<212> TYPE: PRT
<213> ORGANISM: Cyamopsis tetragonoloba

<400> SEQUENCE: 2

```
Met Arg Asn Leu Ile Phe Glu Glu Pro Glu Gly Ile Pro Gly Asn Ser
  1               5                  10                  15

Ser Ser Ser Leu Arg Tyr Ala Trp Gln Ser Ile Arg Ala Pro Val Ile
             20                  25                  30

Ile Pro Leu Leu Lys Leu Ala Val Ile Val Cys Ser Val Met Ser Ile
         35                  40                  45

Met Leu Phe Val Glu Arg Val Ala Met Ala Ala Val Ile Leu Ile Val
     50                  55                  60

Lys Val Leu Arg Lys Lys Arg Tyr Thr Lys Tyr Asn Leu Glu Ala Met
 65                  70                  75                  80

Lys Gln Lys Leu Glu Arg Ser Lys Lys Tyr Pro Met Val Leu Ile Gln
                 85                  90                  95

Ile Pro Met Tyr Asn Glu Lys Glu Val Tyr Lys Leu Ser Ile Gly Ala
            100                 105                 110

Val Cys Gly Leu Ser Trp Pro Ala Asp Arg Phe Ile Val Gln Val Leu
        115                 120                 125

Asp Asp Ser Thr Asn Pro Val Leu Arg Glu Leu Val Glu Met Glu Cys
    130                 135                 140

Gln Lys Trp Ile Gln Lys Gly Val Asn Val Lys Tyr Glu Asn Arg Arg
145                 150                 155                 160

Asn Arg Asn Gly Tyr Lys Ala Gly Ala Leu Lys Glu Gly Leu Glu Lys
                165                 170                 175

Gln Tyr Val Glu Asp Cys Glu Phe Val Ala Ile Phe Asp Ala Asp Phe
            180                 185                 190

Gln Pro Asp Ala Asp Phe Leu Trp Asn Thr Ile Pro Tyr Leu Leu Glu
        195                 200                 205

Asn Pro Lys Leu Gly Leu Val Gln Ala Arg Trp Lys Phe Val Asn Ser
    210                 215                 220

Glu Glu Cys Met Met Thr Arg Leu Gln Glu Met Ser Leu Asp Tyr His
225                 230                 235                 240

Phe Ser Val Glu Gln Glu Val Gly Ser Ser Thr Tyr Ser Phe Phe Gly
                245                 250                 255
```

-continued

```
Phe Asn Gly Thr Ala Gly Val Trp Arg Ile Gln Ala Ile Lys Asp Ala
        260                 265                 270
Gly Gly Trp Lys Asp Arg Thr Thr Val Glu Asp Met Asp Leu Ala Val
    275                 280                 285
Arg Ala Ser Leu His Gly Trp Glu Phe Val Phe Val Gly Asp Val Lys
290                 295                 300
Val Lys Asn Glu Leu Pro Ser Thr Phe Lys Ala Tyr Arg Phe Gln Gln
305                 310                 315                 320
His Arg Trp Ser Cys Gly Pro Ala Asn Leu Phe Lys Lys Met Thr Lys
            325                 330                 335
Glu Ile Ile Cys Cys Lys Arg Val Pro Leu Leu Lys Arg Leu His Leu
        340                 345                 350
Ile Tyr Ala Phe Phe Val Arg Lys Ile Val Ala His Trp Val Thr
    355                 360                 365
Phe Phe Phe Tyr Cys Ile Val Ile Pro Ala Cys Val Ile Val Pro Glu
370                 375                 380
Val Asn Leu Lys Lys Gln Ile Ala Ile Tyr Ile Pro Ala Thr Ile Thr
385                 390                 395                 400
Ile Leu Asn Ala Val Ser Thr Pro Arg Ser Met His Leu Leu Val Leu
            405                 410                 415
Trp Ile Leu Phe Glu Asn Val Met Ser Leu His Arg Thr Lys Ala Ala
        420                 425                 430
Ile Ile Gly Leu Leu Glu Ala Asn Arg Val Asn Glu Trp Val Val Thr
    435                 440                 445
Glu Lys Leu Gly Asn Ala Met Lys Gln Arg Asn Asn Ala Arg Pro Ser
450                 455                 460
Arg Ala Ser Arg Phe Arg Ile Ile Glu Arg Ile His Pro Leu Glu Ile
465                 470                 475                 480
Ile Val Gly Met Tyr Met Leu His Cys Ala Thr Tyr Asp Leu Leu Phe
            485                 490                 495
Gly His Asp His Phe Val Tyr Leu Leu Leu Gln Ala Gly Ala Phe
        500                 505                 510
Phe Thr Met Gly Phe Gly Leu Val Gly Thr Ile Val Pro Thr
    515                 520                 525
```

<210> SEQ ID NO 3
<211> LENGTH: 1609
<212> TYPE: DNA
<213> ORGANISM: Cyamopsis tetragonoloba

<400> SEQUENCE: 3

```
ggaattcggc acgaggctcc catggcgaaa tcctccaatt ccagaaacaa aatttcacac      60
gtaaacctct ccgacggttt cctcttcctc gccggagcat tctccgcgct tctaatcgtt     120
tggggttttct cctccttcac aaccccccatc cctaacgaaa ccccaacctt cgaatcactt     180
tcggtaaatt ctcaccaaaa cgacgccgtt tcgcgcgggg gaccggattt ccggttcgat     240
cccccggacc ggactttcta cgacgacccg gaaatgggt acaccataga acgacggtg      300
cgagattggg atgcaaagcg tgaggagtgg ctgcggcttc atccttcctt cgccgccgga     360
gcgagagaac gagttttggt ggtgaccgga tcgcagccgg caccgtgccg gaatcccatc     420
ggcgaccact tgctgttacg gttttttaag aacaaggtgg attactgtcg gttacacggg     480
tacgatatcg tgtacaacaa tgcattgtta caccccgaaaa tgttcacgta ttgggcgaag     540
taccccggtgg tgcgggccgc gatgatggcc caccccggaag ccgagtggat ctggtgggtc     600
```

-continued

```
gactcggacg cgttgttcac cgacatggag ttcaaactac cattagatca ctacaaggat    660
cacaacctcg tcgtccatgg ctgggcccac ctcatccacg agaaacgtag ttggacgggc    720
ctcaacgccg cgtcttcct catcagaaac tgtcaatggt cattggactt cataaacgaa    780
tgggccagca tgggcccaca aactccgaac tacgagaaat ggggtcaaac cctaaagtca    840
actttcaaag acaaattctt cccggagtca gacgatcaga cgggcctcgc ttacctgatc    900
gcgatcgaga agaaaaatg gcggacaag atttacttag agaactcgta ttatttcgaa    960
gggtactggg aagaaatcgt cggaacattc gagaatataa gcaagaaata caacgagatc   1020
gaaacggggg tgcgcaggtt aagaaggcgt cacgcggaga agtgagtga agcttacggt   1080 gaagagaggg agaaatattt aacgaaagca ggtaacggta aggaagctg agacggccg    1140 tttgtgacgc acttcacggg gtgtcaacct tgtagcggaa aatataacgc tatgtataac   1200
gccgaagatt gttggaacgg aatgcgtaaa gcccttaatt tcgctgataa tcaggtgatg   1260
cgtaaatatg gtttcgtaca cccggatgta ctagataatt ccgtttcgcc gattccgttt   1320
gattatcccc gtaaccgctc aggtaataat catatttaat ggaatctaat tattgttgac   1380
cgctggctac tcagattctc catgtgttct gtaaagtact agtactacta gtattaaatt   1440
tcttagtgta tatttataa tattttttatt gtatattttc tggcgttttg catatatagt   1500
atcgtgtgga gtagtattta attatgcata agtgaaggga taatttttatt ctttttcgaat   1560 ccctaaaaaa aaaaaaaaaa aaaaaaaaaa aaaaaaaaa aaaaaact                1609
```

<210> SEQ ID NO 4
<211> LENGTH: 445
<212> TYPE: PRT
<213> ORGANISM: Cyamopsis tetragonoloba

<400> SEQUENCE: 4

```
Met Ala Lys Ser Ser Asn Ser Arg Asn Lys Ile Ser His Val Asn Leu
  1               5                  10                  15

Ser Asp Gly Phe Leu Phe Leu Ala Gly Ala Phe Ser Ala Leu Leu Ile
             20                  25                  30

Val Trp Gly Phe Ser Ser Phe Thr Thr Pro Ile Pro Asn Glu Thr Pro
         35                  40                  45

Thr Phe Glu Ser Leu Ser Val Asn Ser His Gln Asn Asp Ala Val Ser
     50                  55                  60

Arg Gly Gly Pro Asp Phe Arg Phe Asp Pro Asp Arg Thr Phe Tyr
 65                  70                  75                  80

Asp Asp Pro Glu Met Gly Tyr Thr Ile Asp Thr Thr Val Arg Asp Trp
                 85                  90                  95

Asp Ala Lys Arg Glu Glu Trp Leu Arg Leu His Pro Ser Phe Ala Ala
            100                 105                 110

Gly Ala Arg Glu Arg Val Leu Val Val Thr Gly Ser Gln Pro Ala Pro
        115                 120                 125

Cys Arg Asn Pro Ile Gly Asp His Leu Leu Leu Arg Phe Phe Lys Asn
    130                 135                 140

Lys Val Asp Tyr Cys Arg Leu His Gly Tyr Asp Ile Val Tyr Asn Asn
145                 150                 155                 160

Ala Leu Leu His Pro Lys Met Phe Thr Tyr Trp Ala Lys Tyr Pro Val
                165                 170                 175

Val Arg Ala Ala Met Met Ala His Pro Glu Ala Glu Trp Ile Trp Trp
            180                 185                 190
```

```
Val Asp Ser Asp Ala Leu Phe Thr Asp Met Glu Phe Lys Leu Pro Leu
        195                 200                 205
Asp His Tyr Lys Asp His Asn Leu Val Val His Gly Trp Ala His Leu
    210                 215                 220
Ile His Glu Lys Arg Ser Trp Thr Gly Leu Asn Ala Gly Val Phe Leu
225                 230                 235                 240
Ile Arg Asn Cys Gln Trp Ser Leu Asp Phe Ile Asn Glu Trp Ala Ser
            245                 250                 255
Met Gly Pro Gln Thr Pro Asn Tyr Glu Lys Trp Gly Gln Thr Leu Lys
        260                 265                 270
Ser Thr Phe Lys Asp Lys Phe Phe Pro Glu Ser Asp Gln Thr Gly
    275                 280                 285
Leu Ala Tyr Leu Ile Ala Ile Glu Lys Glu Lys Trp Ala Asp Lys Ile
    290                 295                 300
Tyr Leu Glu Asn Ser Tyr Tyr Phe Gly Tyr Trp Glu Glu Ile Val
305                 310                 315                 320
Gly Thr Phe Glu Asn Ile Ser Lys Lys Tyr Asn Glu Ile Glu Thr Gly
            325                 330                 335
Val Arg Arg Leu Arg Arg Arg His Ala Glu Lys Val Ser Glu Ala Tyr
        340                 345                 350
Gly Glu Glu Arg Glu Lys Tyr Leu Thr Glu Ala Gly Asn Gly Lys Gly
    355                 360                 365
Ser Trp Arg Arg Pro Phe Val Thr His Phe Thr Gly Cys Gln Pro Cys
370                 375                 380
Ser Gly Lys Tyr Asn Ala Met Tyr Asn Ala Glu Asp Cys Trp Asn Gly
385                 390                 395                 400
Met Arg Lys Ala Leu Asn Phe Ala Asp Asn Gln Val Met Arg Lys Tyr
            405                 410                 415
Gly Phe Val His Pro Asp Val Leu Asp Asn Ser Val Ser Pro Ile Pro
        420                 425                 430
Phe Asp Tyr Pro Arg Asn Arg Ser Gly Asn Asn His Ile
    435                 440                 445

<210> SEQ ID NO 5
<211> LENGTH: 1391
<212> TYPE: DNA
<213> ORGANISM: Cyamopsis tetragonoloba

<400> SEQUENCE: 5
gtatcacatt cactcactcc catggccaaa tttggttcca gaaacaaatc ccctaaatgg     60
atctccaacg gttgctgctt cctcctagga gcattcactg ctcttcttct gctctggggt    120
ttatgctcct tcatcatccc catcccaaac accgacccca agctcaactc cgtcgccacc    180
agtttgagat cccttaactt tcccaaaaac cccgctgcca ccttgcctcc caacttgcag    240
cacgaccctc ctgacaccac cttctacgac gaccccgaaa ccagttatac catggacaaa    300
ccaatgaaaa actgggacga agcgtaag gagtggttgc tgcatcatcc ttcgtttggc     360
gccgcagcac gcgataagat tctcctggtg acaggttctc agccgaaacg gtgccataac    420
ccgatcggcg accacctcct gttgcggttt ttcaagaaca aggtggatta ctgccggctg    480
cacaactacg acataattta caacaacgcg cttctgcatc ctaaaatgaa ctcttattgg    540
gccaagtatc cagtgattcg ggcggcgatg atggcccatc cggaagtgga gtgggtgtgg    600
tgggtggact cggacgcggt tttcacggac atggagttca gcttccgtt aaagcgttat    660 aagaaccaca atctggtggt tcacggttgg gaaggattgg tacggttgaa ccatagctgg    720
```

```
acgggtctaa acgcgggcgt attcttgatt cggaattgcc agtggtcgtt ggagttcatg    780
gatgtgtggg tgagcatggg gccacagact ccggaatacg agaaatgggg ggagaggttg    840
agagagacat tcaaggacaa ggtgctgcct gattcggacg atcagacggc gctggcttac    900
ctgatcgcga cggataataa ggacacgtgg agggagaaga tcttcttgga gagcgagtac    960
tacttcgaag gtactggct ggagatcgtg aagacgtacg agaacataag cgagaggtat   1020
gatgaggtgg agaggaaggt ggaagggttg aggaggaggc atgcggaaaa ggtgagcgag   1080
aaatacggtg cgatgaggga ggagtatctg aaggacaaca agaggaggcc ctttatcacg   1140
cactttactg ggtgtcaacc ctgtaatggc caccataatc ctgcttataa tgctaatgat   1200
tgctggaatg gcatggagag ggctcttaat ttcgctgata atcaaatctt gcgtacttac   1260
ggttatcacc gtcaaaattt actcgacaag tctgtttcac ccttaccttt tggttaccct   1320
gctgcataat aatgtactac tactgataac gacagttatt taaaatttat tatacgatcc   1380
caacgaacgc c                                                         1391
```

<210> SEQ ID NO 6
<211> LENGTH: 435
<212> TYPE: PRT
<213> ORGANISM: Cyamopsis tetragonoloba

<400> SEQUENCE: 6

```
Met Ala Lys Phe Gly Ser Arg Asn Lys Ser Pro Lys Trp Ile Ser Asn
1               5                   10                  15

Gly Cys Cys Phe Leu Leu Gly Ala Phe Thr Ala Leu Leu Leu Leu Trp
                20                  25                  30

Gly Leu Cys Ser Phe Ile Ile Pro Ile Pro Asn Thr Asp Pro Lys Leu
            35                  40                  45

Asn Ser Val Ala Thr Ser Leu Arg Ser Leu Asn Phe Pro Lys Asn Pro
        50                  55                  60

Ala Ala Thr Leu Pro Pro Asn Leu Gln His Asp Pro Pro Asp Thr Thr
65                  70                  75                  80

Phe Tyr Asp Asp Pro Glu Thr Ser Tyr Thr Met Asp Lys Pro Met Lys
                85                  90                  95

Asn Trp Asp Glu Lys Arg Lys Glu Trp Leu His His Pro Ser Phe
                100                 105                 110

Gly Ala Ala Ala Arg Asp Lys Ile Leu Leu Val Thr Gly Ser Gln Pro
            115                 120                 125

Lys Arg Cys His Asn Pro Ile Gly Asp His Leu Leu Leu Arg Phe Phe
        130                 135                 140

Lys Asn Lys Val Asp Tyr Cys Arg Leu His Asn Tyr Asp Ile Ile Tyr
145                 150                 155                 160

Asn Asn Ala Leu Leu His Pro Lys Met Asn Ser Tyr Ala Lys Tyr
                165                 170                 175

Pro Val Ile Arg Ala Ala Met Met Ala His Pro Glu Val Glu Trp Val
            180                 185                 190

Trp Trp Val Asp Ser Asp Ala Val Phe Thr Asp Met Glu Phe Lys Leu
        195                 200                 205

Pro Leu Lys Arg Tyr Lys Asn His Asn Leu Val Val His Gly Trp Glu
    210                 215                 220

Gly Leu Val Arg Leu Asn His Ser Trp Thr Gly Leu Asn Ala Gly Val
225                 230                 235                 240

Phe Leu Ile Arg Asn Cys Gln Trp Ser Leu Glu Phe Met Asp Val Trp
```

```
                245                 250                 255
Val Ser Met Gly Pro Gln Thr Pro Glu Tyr Glu Lys Trp Gly Glu Arg
            260                 265                 270

Leu Arg Glu Thr Phe Lys Asp Lys Val Leu Pro Asp Ser Asp Asp Gln
        275                 280                 285

Thr Ala Leu Ala Tyr Leu Ile Ala Thr Asp Asn Lys Asp Thr Trp Arg
    290                 295                 300

Glu Lys Ile Phe Leu Glu Ser Glu Tyr Tyr Phe Gly Tyr Trp Leu
305                 310                 315                 320

Glu Ile Val Lys Thr Tyr Glu Asn Ile Ser Glu Arg Tyr Asp Glu Val
                325                 330                 335

Glu Arg Lys Val Glu Gly Leu Arg Arg Arg His Ala Glu Lys Val Ser
            340                 345                 350

Glu Lys Tyr Gly Ala Met Arg Glu Glu Tyr Leu Lys Asp Asn Lys Arg
        355                 360                 365

Arg Pro Phe Ile Thr His Phe Thr Gly Cys Gln Pro Cys Asn Gly His
    370                 375                 380

His Asn Pro Ala Tyr Asn Ala Asn Asp Cys Trp Asn Gly Met Glu Arg
385                 390                 395                 400

Ala Leu Asn Phe Ala Asp Asn Gln Ile Leu Arg Thr Tyr Gly Tyr His
                405                 410                 415

Arg Gln Asn Leu Leu Asp Lys Ser Val Ser Pro Leu Pro Phe Gly Tyr
            420                 425                 430

Pro Ala Ala
        435

<210> SEQ ID NO 7
<211> LENGTH: 269
<212> TYPE: PRT
<213> ORGANISM: Cyamopsis tetragonoloba

<400> SEQUENCE: 7

Met Val Leu Ile Gln Ile Pro Met Tyr Asn Glu Lys Glu Val Tyr Lys
1               5                   10                  15

Leu Ser Ile Gly Ala Val Cys Gly Leu Ser Trp Pro Ala Asp Arg Phe
            20                  25                  30

Ile Val Gln Val Leu Asp Asp Ser Thr Asn Pro Val Leu Arg Glu Leu
        35                  40                  45

Val Glu Met Glu Cys Gln Lys Trp Ile Gln Lys Gly Val Asn Val Lys
    50                  55                  60

Tyr Glu Asn Arg Arg Asn Arg Asn Gly Tyr Lys Ala Gly Ala Leu Lys
65                  70                  75                  80

Glu Gly Leu Glu Lys Gln Tyr Val Glu Asp Cys Glu Phe Val Ala Ile
                85                  90                  95

Phe Asp Ala Asp Phe Gln Pro Asp Ala Asp Phe Leu Trp Asn Thr Ile
            100                 105                 110

Pro Tyr Leu Leu Glu Asn Pro Lys Leu Gly Leu Val Gln Ala Arg Trp
        115                 120                 125

Lys Phe Val Asn Ser Glu Glu Cys Met Met Thr Arg Leu Gln Glu Met
    130                 135                 140

Ser Leu Asp Tyr His Phe Ser Val Glu Gln Val Gly Ser Ser Thr
145                 150                 155                 160

Tyr Ser Phe Phe Gly Phe Asn Gly Thr Ala Gly Val Trp Arg Ile Gln
                165                 170                 175
```

```
Ala Ile Lys Asp Ala Gly Gly Trp Lys Asp Arg Thr Thr Val Glu Asp
            180                 185                 190

Met Asp Leu Ala Val Arg Ala Ser Leu His Gly Trp Glu Phe Val Phe
        195                 200                 205

Val Gly Asp Val Lys Val Lys Asn Glu Leu Pro Ser Thr Phe Lys Ala
    210                 215                 220

Tyr Arg Phe Gln Gln His Arg Trp Ser Cys Gly Pro Ala Asn Leu Phe
225                 230                 235                 240

Lys Lys Met Thr Lys Glu Ile Ile Cys Cys Lys Arg Val Pro Leu Leu
                245                 250                 255

Lys Arg Leu His Leu Ile Tyr Ala Phe Phe Phe Val Arg
            260                 265

<210> SEQ ID NO 8
<211> LENGTH: 33
<212> TYPE: DNA
<213> ORGANISM: Artificial Sequence
<220> FEATURE:
<223> OTHER INFORMATION: Primer

<400> SEQUENCE: 8
ttgtctcgag ttatctcaca aagaagaaag cat                            33

<210> SEQ ID NO 9
<211> LENGTH: 1349
<212> TYPE: DNA
<213> ORGANISM: Cyamopsis tetragonoloba

<400> SEQUENCE: 9
ggtgatgcaa atcgcatgag aggggaagaa gaggtgtctc acttactctt caatcttcat    60
tcacccttac gagtgccacc tctcttctct ccttctcttc acagctcaaa caatttgctg   120
ttaaactttg atcggttcat ccatggaaga aaccttcgtt ttccagtgga gcgttatcag   180
atctctcttg tccatccttc agtggtgggc tttcaatgtc accgttatca tcgttaacaa   240
gtggatcttc cagaaattgg atttcaagtt tccccttttca gtatcctgtg tacacttttat   300 ctgctcagca attggagcat atatcgtgat taaggtgctg aagcttaaac cactgataac   360
tgttgacccc tgatgatcgct ggagaagaat atttcctatg tcatttgtat tctgtattaa   420
catagtgctg gggaatgtga gcctacggta tattccagtt tcttttatgc agacgataaa   480
gtcattcacg cctgcaacta cagttgttct gcaatggctt gtatggagaa agtatttga   540 ctggcgtatt tgggcttctc ttattcccat tgttggaggg attcttctta catctgtaac   600
agagcttagt tttaatatgt ttggattttg tgctgcctta tttggttgtt tggccacatc   660
tacgaagact atccttgcag aatctctttt gcatggatac aaatttgata gcataaacac   720
agtttactac atggcaccct ttgcaaccat gatcttggcg cttcctgcca tgttactcga   780
aggaaatgga attcttgact ggctaaacac tcatccatat ccttggtcag ccctcatcat   840
tattttcagc tctggggttt tggctttctg tctcaacttc tccattttt acgtgattca   900 ctccaccact gctgtaacct taacgttgc cggaaacctt aaggttgcag ttgctgttct   960
ggtttcatgg ctgatatttta ggaacccaat atcatactta aatgcagttg gatgtgccgt  1020
gacacttgtg ggatgtacat tctatggtta tgtaaggcac atgctctccc aacagccacc  1080
agttccagga actcctcgaa ctccaaggac ccctcgcagt aagatggagt actccctct  1140 tgtaaatgat aaattagaag ataaggtcta attgttttag ctatgtacac gaggtttatg  1200
tcatttctaa ggcagtagta acagcaatat aggtacaaaa ggattacagt gactggttat  1260
```

```
ttattccgtt agattatccc aaaattttca atacaagttc ttttacattc cctttttaaa    1320
aaaaaaaaaa aaaaaaaaaa aaaaaaaaa                                     1349
```

<210> SEQ ID NO 10
<211> LENGTH: 342
<212> TYPE: PRT
<213> ORGANISM: Cyamopsis tetragonoloba

<400> SEQUENCE: 10

```
Met Glu Glu Thr Phe Val Phe Gln Trp Ser Val Ile Arg Ser Leu Leu
 1               5                  10                  15

Ser Ile Leu Gln Trp Trp Ala Phe Asn Val Thr Val Ile Ile Val Asn
             20                  25                  30

Lys Trp Ile Phe Gln Lys Leu Asp Phe Lys Phe Pro Leu Ser Val Ser
         35                  40                  45

Cys Val His Phe Ile Cys Ser Ala Ile Gly Ala Tyr Ile Val Ile Lys
     50                  55                  60

Val Leu Lys Leu Lys Pro Leu Ile Thr Val Asp Pro Asp Asp Arg Trp
 65                  70                  75                  80

Arg Arg Ile Phe Pro Met Ser Phe Val Phe Cys Ile Asn Ile Val Leu
                 85                  90                  95

Gly Asn Val Ser Leu Arg Tyr Ile Pro Val Ser Phe Met Gln Thr Ile
            100                 105                 110

Lys Ser Phe Thr Pro Ala Thr Thr Val Val Leu Gln Trp Leu Val Trp
        115                 120                 125

Arg Lys Tyr Phe Asp Trp Arg Ile Trp Ala Ser Leu Ile Pro Ile Val
    130                 135                 140

Gly Gly Ile Leu Leu Thr Ser Val Thr Glu Leu Ser Phe Asn Met Phe
145                 150                 155                 160

Gly Phe Cys Ala Ala Leu Phe Gly Cys Leu Ala Thr Ser Thr Lys Thr
                165                 170                 175

Ile Leu Ala Glu Ser Leu Leu His Gly Tyr Lys Phe Asp Ser Ile Asn
            180                 185                 190

Thr Val Tyr Tyr Met Ala Pro Phe Ala Thr Met Ile Leu Ala Leu Pro
        195                 200                 205

Ala Met Leu Leu Glu Gly Asn Gly Ile Leu Asp Trp Leu Asn Thr His
    210                 215                 220

Pro Tyr Pro Trp Ser Ala Leu Ile Ile Ile Phe Ser Ser Gly Val Leu
225                 230                 235                 240

Ala Phe Cys Leu Asn Phe Ser Ile Phe Tyr Val Ile His Ser Thr Thr
                245                 250                 255

Ala Val Thr Phe Asn Val Ala Gly Asn Leu Lys Val Ala Val Ala Val
            260                 265                 270

Leu Val Ser Trp Leu Ile Phe Arg Asn Pro Ile Ser Tyr Leu Asn Ala
        275                 280                 285

Val Gly Cys Ala Val Thr Leu Val Gly Cys Thr Phe Tyr Gly Tyr Val
    290                 295                 300

Arg His Met Leu Ser Gln Gln Pro Val Pro Gly Thr Pro Arg Thr
305                 310                 315                 320

Pro Arg Thr Pro Arg Ser Lys Met Glu Leu Leu Pro Leu Val Asn Asp
                325                 330                 335

Lys Leu Glu Asp Lys Val
            340
```

GENES FOR GALACTOMANNAN PRODUCTION IN PLANTS AND METHODS OF USE

CROSS-REFERENCE TO RELATED APPLICATIONS

This application claims the benefit of, and hereby incorporates by reference U.S. Provisional Application No. 60/426,127, filed Nov. 14, 2002, and U.S. Provisional Application No. 60/490/022, filed Jul. 25, 2003.

FIELD OF THE INVENTION

The invention relates to the genetic manipulation of plants for galactomannan production, particularly to the expression and regulation of mannan synthase and galactosyltransferase in transformed plants.

BACKGROUND OF THE INVENTION

Seeds of endospermic legumes accumulate polysaccharides as storage polysaccharides referred to as gums because these polysaccharides produce gels or highly viscous solutions at low concentrations in solvents, and thus, these polysaccharides have a myriad of applications in industry (Whistler et al., Introduction to industrial gums, In Industrial Gums: Polysaccharides and their derivatives, Whistler and BeMiller, eds., Academic Press, San Diego, pp. 1-19, 1993). The main sources of seed-derived industrial gums are guar (Cyamopsis tetragonoloba), locust bean or carob (Ceratonia siliqua), tara (Caesalpinia spinosa), and fenugreek (Trigonella foenum-graecum), which are all native to subtropical areas. Another class of plant gums, xyloglucans, has not received much attention perhaps because of the low yield of the source seeds. Xyloglucan occurs as a storage polysaccahride in the seeds of nasturtium (Tropaeolum majus), tamarind (Tamarindus indica), and balsam (Impatiens balsamina) (Maier et al., Guar, Locust Bean, Tara, and Fenugreek gum, In Industrial Gums: polysaccharides and their derivatives, Whistler and BeMiller eds., Academic Press, Inc., London, pp. 181-226, 1993; Reid et al., Adv. Bot. Res. 11:125-155, 1985).

As they can absorb large volumes of water, gums are used as food additives to provide texture, prevent ice crystal formation, maintain crispness, and retain moisture (Maier et al., Guar, Locust Bean, Tara, and Fenugreek gums. In Industrial Gums: polysaccharides and their derivatives, Whistler and BeMiller, eds., Academic Press, Inc., London, pp. 181-226, 1993; Anderson and Andon, Cereal Foods World 33:844-850, 1988; Ward and Andon, Cereal Foods World 38:748-752, 1993; Bayerlein, Technical applications of galactomannans. In Plant polymeric carbohydrates, Meuser Manne, and Seibel eds., The Royal Society of Chemistry, Cambridge, pp. 191-202, 1993; Whistler and BeMiller, Guar and Locust Bean Gums, American Society of Cereal Chemists, St. Paul, Minn., pp. 171-177, 1997). Other uses of gums are in the following non-food industries: a) textiles, as dying and printing aids; b) petroleum, as drilling agents for oil and gas wells; c) paper, as binders and hardeners; d) mining and minerals, for separation of minerals from crude ores; e) explosives, to thicken explosive slurries and as desiccants; and f) cosmetics, to thicken shampoos and conditioners (Maier et al., Guar, Locust Bean, Tara, and Fenugreek gums. In Industrial Gums: polysaccharides and their derivatives, Whistler and BeMiller, eds., Academic Press, Inc., London, pp. 181-226, 1993; Bayerlein, Technical applications of galactomannans. In Plant polymeric carbohydrates, Meuser Manners, and Seibel eds., The Royal Society of Chemistry, Cambridge, pp. 191-202, 1993; Soni, Indian Forester 110:931-935, 1984; Siharma, Indian Forester 111:149-157, 1985; Prakash, Bucharest: Academia Republicii Socialiste Romania. 18:207-212, 1984; Pszczola, D. E., Food Technology 47:94-6, 1993; Bayerlein et al., Official Gazette Of The United States Patent And TrademarkOffice Patents 1102:424, 1989; Sudhakar et al., Food Hydrocolloids 10:329-334, 1996). A new, rapidly emerging area for gum applications is human health and medicine where they have been reported to be useful as soluble fiber (Cameron-Smith et al., Journal Of Nutrition 127:359-364, 1997), in lowering blood cholesterol and blood pressure (Blake et al., American Journal Of Clinical Nutrition 65:107-113, 1997), as weight-loss facilitators (Brennan et al., Journal Of Cereal Science 24:151-160, 1996), in lowering blood glucose (Fairchild et al., British J. Nutrition 76:63-73, 1996), as aids for slow release of pharmaceutical drugs (Waaler et al., Acta Pharmaceutica Nordica 4:167-170, 1992), in improving microflora of the digestive system (Takahashi et al., Nutrition Research 15:527-536, 1995), and in prolonging the release of sugar during strenuous physical exercise (Maclaren et al., International Journal Of Sports Medicine 15:466-471, 1994). On a scientific technical note, gums have been used as substitutes for polyethylene glycol in phase partition systems for the separation of cell organelles and membranes (Venancio et al., Bioseparation 5:253-258, 1995).

Natural industrial gums are currently prepared from bacteria or the aforementioned plants or trees. Guar and locust bean account for more than 70% of the natural plant gum market (Bayerlein, Technical applications of galactomannans. In Plant polymeric carbohydrates, Meuser Manners, and Seibel eds., The Royal Society of Chemistry, Cambridge, pp. 191-202, 1993). With an annual global demand for guar and locust bean gums of 200 million pounds and 35 million pounds at a price of $0.70 and $16 per pound, respectively, the market size translates into a $700 million which, when combined with other plant gums, exceeds $1 billion (Bayerlein, Technical applications of galactomannans. In Plant polymeric carbohydrates, Meuser Manners, and Seibel eds., The Royal Society of Chemistry, Cambridge, pp. 191-202, 1993; Industrial uses of agricultural materials: situations and outlook, Volume ISU6, D. Decker, ed. United States Department of Agriculture Washington, D.C., p. 54, 1996).

High price has probably been the reason for a slow expansion of the market size for gums. Production of gums at a lower cost should substantially increase the market size, given that a multitude of applications are already in place. Maier et al., Guar, Locust Bean, Tara, and Fenugreek gums. In Industrial Gums: polysaccharides and their derivatives, Whistler and BeMiller, eds., Academic Press, Inc., London, pp. 181-226, 1993). Whistler and BeMiller, Guar and Locust Bean Gums. In Carbohydrate chemistry for food scientists, Whistler and BeMiller, eds. American Society of Cereal Chemists St. Paul, pp. 171-177, 1997).

BRIEF SUMMARY OF THE INVENTION

The synthesis of the gum galactomannan is catalyzed by the enzymes mannan synthase and galactosyltransferase, from the substrates GDP-mannose and UDP-galactose, respectively. The present invention provides compositions and methods for manipulating the levels of enzymes in the galactomannan biosynthetic pathway in order to regulate gum production in plants, plant cells and plant tissues.

The compositions comprise isolated nucleotide molecules comprising nucleotide sequences that encode enzymes involved in galactomannan synthesis in a plant. In particular, the invention provides isolated nucleotide molecules comprising a nucleotide sequence that encodes a mannan synthase (SEQ ID NO:1) and isolated nucleotide molecules comprising a nucleotide sequence that encodes a galactosyltransferase (SEQ ID NO:3). The invention further provides nucleotide constructs or expression cassettes comprising such nucleotide molecules operably linked to a promoter for expression in non-human host cells, particularly plant cells. Additionally provided are isolated polypeptides encoded by such nucleotide molecules, particularly mannan synthase polypeptide having the amino acid sequence set forth in SEQ ID NO:2 and the galactosyl transferase polypeptide having the amino acid sequence set forth in SEQ ID NO:4.

The nucleotide molecules and expression cassettes find use in methods for altering the level of galactomannans produced in a plant or at least one part thereof. That is the methods can be used to increase or decrease the level of galactomannan produced in a plant or at least one part thereof. The methods comprise transforming a plant cell with at least one nucleotide construct comprising a nucleotide molecule of the invention operably linked to a promoter that is capable of driving gene expression in a plant. The promoter can be operably linked to the nucleotide molecule of the invention for the production of sense or antisense RNA. The methods further comprise regenerating a stably transformed plant from the transformed plant cell. Such a stably transformed plant comprises stably incorporated in its genome the nucleotide construct of the invention and has an altered level of galactomannan in the plant or at least one part thereof. The methods of the invention may involve transforming a plant with a single nucleotide molecule encoding a mannan synthase or galactosyltransferase, or two, three, four or more nucleotide molecule encoding enzymes involved in galactomannan production in a plant. Nucleotide molecules encoding a mannan synthase include, but are not limited to, the nucleotide molecules having the sequence set forth in SEQ ID NO:1 and functional fragments and variants thereof which encode polypeptides having mannan synthase activity, as well as any nucleotide molecule that is known in the art which encodes mannan synthase or a polypeptide having mannan synthase activity. Nucleotide molecules encoding a galactosyltransferase include SEQ ID NO:3 and functional fragments and variants thereof which encode polypeptides having galactosyltransferase activity.

For example, the methods encompass transforming a plant with a nucleotide molecule encoding a mannan synthase of the invention, such as, for example, SEQ ID NO:1, and at least one nucleotide molecule encoding a galactosyltransferase, including, but not limited to, those nucleotide molecules having the nucleotide sequences set forth in SEQ ID NOS:1, 3, and 5. If desired, such a plant can also be transformed with one or more additional nucleotide molecules. Such additional nucleotide molecules include any nucleotide molecule known in that art that encodes an enzyme involved in galactomannan biosynthesis in a plant or other organism as well as those nucleotide molecules known in that art which encode other enzymes or other proteins that can affect the level of galactomannan produced in a plant. See, for example, copending U.S. application Ser. No. 09/374,967, entitled "Compositions and Methods for Manipulating Gum Production in Plants", filed Aug. 16, 1999, and WO 99/60103, both of which are herein incorporated by reference. Such other enzymes that may be used to enhance the level of galactomannan production in a plant by the methods of the invention include, for example, UDP-glucose-4-epimerase (EC 5.1.3.2) and phosphomannoisomerase (EC 5.3.1.8).

The nucleotide molecules of the invention also find use in methods for altering the ratio of galactose to mannose present in galactomannan polysaccharides in a plant. It is recognized that increasing the expression of such a galactosyltransferase can increase the ratio of galactose to mannose present in the galactomannan produced in a plant or at least one part thereof and that decreasing the expression of such galactosyltransferase can decrease the ratio of galactose to mannose present in the galactomannan produced in a plant. It is further recognized that the quality for industrial uses of galactomannan depends on its ratio of mannose to galactose therein. Accordingly, the nucleotide molecules of the invention provide us the tools to produce high quality galactomannans for industrial uses. The method for altering the ratio of mannose to galactose present in galactomannan polysaccharides comprise transforming a plant cell with at least one nucleotide construct operably linked to a promoter that drives expression in a plant. The nucleotide molecule can comprise a nucleotide molecule that encodes a galactosyltransferase that is involved in the biosynthesis of galactomannan. Such nucleotide molecules encoding a galactosyltransferase include, but are not limited to those having the sequence set forth in SEQ ID NO:3 and Accession No. AX010245 (SEQ ID NO:5). The promoter can be operably linked to the nucleotide molecule of the invention for the production of sense or antisense RNA.

It is recognized that a variety of promoters may be utilized in the constructs of the invention depending on the desired outcome. Tissue-preferred promoters, seed-preferred promoters, inducible promoters, developmental promoters, or constitutive promoters can be used to direct expression of the enzymes for galactomannan biosynthesis to desired location and/or at a desired time in a plant.

Additionally provided are transformed plants, plant tissues, plant cells, and seeds. Such transformed plants, tissues, cells, and seeds comprise stably incorporated in their genomes at least one nucleotide molecule of the invention.

Embodiments of the invention include, but are not limited to:

1. An isolated nucleic acid molecule comprising a nucleotide sequence selected from the group consisting of:
    (a) the nucleotide sequence set forth in SEQ ID NO:1;
    (b) a nucleotide sequence encoding the amino acid sequence set forth in SEQ ID NO:2 or 7;
    (c) the nucleotide sequence set forth in SEQ ID NO:3; and
    (d) a nucleotide sequence encoding the amino acid sequence set forth in SEQ ID NO:4.

2. An expression cassette comprising a nucleotide acid molecule of embodiment 1 operably linked to a promoter that is capable of driving expression in a host cell.

3. A transformed plant comprising in its genome at least one stably incorporated nucleotide construct comprising a nucleotide sequence operably linked to a promoter that is capable of driving expression in a plant cell, wherein said nucleotide sequence is selected from the group consisting of:
(a) the nucleotide sequence set forth in SEQ ID NO:1;
(b) a nucleotide sequence encoding the amino acid sequence set forth in SEQ ID NO:2 or 7;
(c) the nucleotide sequence set forth in SEQ ID NO:3; and
(d) a nucleotide sequence encoding the amino acid sequence set forth in SEQ ID NO:4.

4. A seed of the plant of embodiment 3, wherein said seed comprises in its genome said nucleotide construct of embodiment 3.

5. A transformed plant cell comprising in its genome at least one stably incorporated nucleotide construct comprising a nucleotide sequence operably linked to a promoter that is capable of driving expression in a plant cell, wherein said nucleotide sequence is selected from the group consisting of:
(a) the nucleotide sequence set forth in SEQ ID NO:1;
(b) a nucleotide sequence encoding the amino acid sequence set forth in SEQ ID NO:2 or 7;
(c) the nucleotide sequence set forth in SEQ ID NO:3; and
(d) a nucleotide sequence encoding the amino acid sequence set forth in SEQ ID NO:4.

6. An isolated polypeptide comprising an amino acid sequence selected from the group consisting of:
(a) the amino acid sequence set forth in SEQ ID NO:2 or 7;
(b) the amino acid sequence set forth in SEQ ID NO:4;
(c) the amino acid sequence encoded by the nucleotide sequence set forth in SEQ ID NO:1; and
(d) the amino acid sequence encoded by the nucleotide sequence set forth in SEQ ID NO:3.

7. A method for altering the level of galactomannan in a plant, said method comprising transforming a plant with a nucleotide construct comprising a nucleotide sequence operably linked to a promoter that is capable of driving expression in a plant cell, wherein said nucleotide sequence is selected from the group consisting of:
(a) the nucleotide sequence set forth in SEQ ID NO:1;
(b) a nucleotide sequence encoding the amino acid sequence set forth in SEQ ID NO:2 or 7;
(c) the nucleotide sequence set forth in SEQ ID NO:3; and
(d) a nucleotide sequence encoding the amino acid sequence set forth in SEQ ID NO:4;

wherein the level of galactomannan in said plant or part thereof is increased or decreased.

It is recognized that the invention encompasses isolated nucleotide molecules comprising variants and fragments of the nucleotide sequences set forth in SEQ ID NOS:1 and 3, wherein said variants and fragments encode polypeptides that have mannan synthase activity or galactosyltransferase activity, respectively. It is further recognized that the plants, plant cells, and methods of the invention are also drawn to the these functional variants and fragments. Similarly, the isolated polypeptides of the invention encompass variants and fragments of the amino acid sequences set forth SEQ ID NOS:2 or 7 and 4, wherein said variants and fragments retain biological activity, particularly mannan synthase activity or galactosyltransferase activity, respectively.

BRIEF DESCRIPTION OF THE DRAWINGS

FIG. 1 is the nucleotide sequence encoding mannan synthase (CtManS) from guar (*Cyamopsis tetragonoloba*) (SEQ ID NO: 1).

FIG. 2 is the amino acid sequence for the mannan synthase (CtMANS) from guar (SEQ ID NO: 2).

FIG. 3 is the nucleotide sequence encoding galactosyltransferase-2 (CtGalT2) from guar (SEQ ID NO: 3).

FIG. 4 is the amino acid sequence for galactosyltransferase-2 (CtGALT2) from guar (SEQ ID NO:4).

FIG. 7 is an alignment of the nucleotide sequences of CtGalT1 (Accession No. AX010245, SEQ ID NO:5), CtGalT2 (SEQ ID NO:3), and the nucleotide sequence encoding a fenugreek galactosyl transferase (Accession No. AJ245478).

FIG. 8 is an alignment of the amino acid sequences of two galactosyltransferases from guar, CtGALT1 (SEQ ID NO:6) and CtGALT2 (SEQ ID NO:4), and one from fenugreek. The CtGALT1 amino acid sequence is the predicted amino acid sequence that is encoded by the nucleotide sequence of Accession No. AX010245.

FIG. 9 is an alignment of the amino acid sequence encoded by CtManS with processive beta-glycosyltransferases. Several motifs including DXD (positions 189-191 in ManS), D (position 283), and QXXRW (positions 319-323) that are diagnostic of the processive beta-glycosyltransferases (described in the introduction) are also conserved in the mannan synthase polypeptide as is shown. The completely conserved amino acids are marked as well. Abbreviations in the sequence alignment below are: At, *Arabidopsis thaliana*; Ct, *Cyamopsis tetragonoloba*; Gh, *Gossypium hirsutum*; Pt, *Populus tremuloides*; and Zm, *Zea mays*.

FIG. 17 shows the expression of the globular domain of mannan synthase as a fusion protein with either thioredoxin (TRX, A) or glutathione-S-transferase (GST, B) on the N-terminal end. On the right (C) are shown purified proteins with TRX tag (left lane) and GST tag (right lane). The left lanes (A and B) contain protein derived from the uninduced cells and the ones on the right from the cells induced with IPTG (isopropyl thio-β-galactoside). The calculated molecular mass of the Trx-fusion protein is approximately 48.5 kDa, of the GST-fusion 63 kDa, and that of the truncated mannan synthase itself is 31.5 kDa. The molecular mass difference resulting from different tags is illustrated.

FIG. 20 is the elution profile of different sugars using HPLC as described in the methods section. The radiolabeled sugars were separately subjected to the HPLC separation, the fractions collected at 0.5 min intervals, and after mixing with a scintillation fluid, counted for the amount of radioactivity in them. ManS refers to the product obtained from the mannan synthase reaction and hydrolyzed with sulfuric acid before HPLC analysis. The suffix indicates the source of membrane preparation used to carry out the assay. Soybean seed refers to transgenic developing seeds.

FIG. 21 is the nucleotide sequence of the guar GDP-mannose transporter (SEQ ID NO: 9).

FIG. 22 is the amino acid sequence of the guar GDP-mannose transporter (SEQ ID NO:10).

FIG. 23, parts (a) and (b), is an alignment of the guar and *Arabidopsis* GDP-mannose transporter protein sequences from the AlignX program of vector NTI.

FIG. 24 is the similarity table of the guar (*Cyanamopsis tetragonoloba L.*) and *Arabidopsis* (At) GDP-mannose transporter proteins.

DETAILED DESCRIPTION OF THE INVENTION

Figure 5:
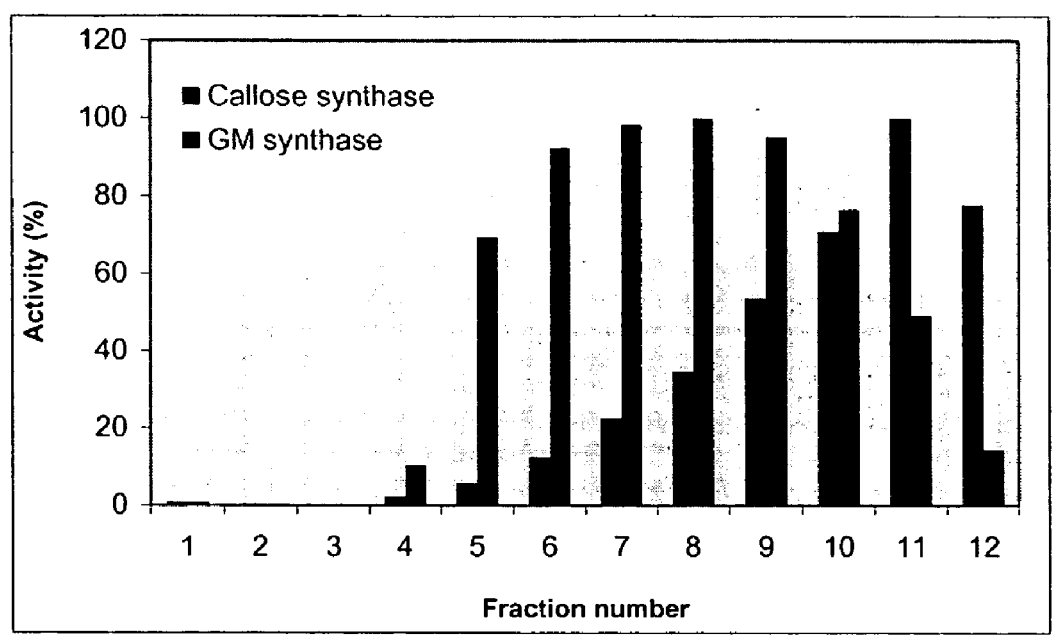
FIG. 5 is a graphical depiction of mannase synthase activity in a membrane fraction isolated from immature guar seeds and separated on a glycerol gradient. A membrane fraction prepared from guar seeds at 25 DAF was solubilized in digitonin, layered onto a glycerol gradient (20%-60% w/w), and centrifuged at 207,000×g for 18 hours. The gradient was separated into 12 fractions and each fraction was assayed for mannan synthase and callose synthase activities.

The present invention discloses compositions and methods for altering the level of galactomannan in plants, plant cells and specific tissues, such as, for example, seeds. The methods involve modulation of the levels of enzymes in the galactomannan biosynthetic pathway. The synthesis of the gum galactomannan is catalyzed by the enzymes mannan synthase and galactosyl transferase, from the substrates GDP-mannose and UDP-galactose. See, U.S. application Ser. No. 09/374,967, herein incorporated in its entirety by reference.

Compositions of the invention include isolated nucleotide molecules and isolated polypeptides that are involved in galactomannan production in plants. Such compositions find use in methods for increasing or decreasing the level of galactomannans present in an organism, particularly a plant, or part thereof. In particular, the present invention provides for isolated nucleic acid molecules comprising nucleotide sequences encoding the amino acid sequences shown in SEQ ID NOS:2 and 4. Further provided are polypeptides having an amino acid sequence encoded by a nucleic acid molecule described herein, for example those set forth in SEQ ID NOS:1 and 3, and fragments and variants thereof.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, preferably culture medium represents less than about 30%, 20%, 10%, 5%, or 1% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a mannan synthase nucleotide sequence may encode protein fragments that retain the biological activity of the native protein and hence mannan synthase activity. Fragments of a galactosyltransferase nucleotide sequence may encode protein fragments that retain the biological activity of the native protein and hence galactosyltransferase activity, particularly a galactosyltransferase activity that comprises the transfer of galactosyl residues in the biosynthesis of galactomannan polysaccharides. Alternatively, fragments of a nucleotide sequence that are useful as hybridization probes generally need not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a mannan synthase nucleotide sequence that encodes a biologically active portion of a mannan synthase protein of the invention will encode at least 15, 25, 30, 50, 100, 150, 200, 300, 400, 450, or 500 contiguous amino acids, or up to the total number of amino acids present in a full-length mannan synthase protein of the invention (for example, 526 amino acids for SEQ ID NO:2). Fragments of a mannan synthase nucleotide sequence or galactosyltransferase that are useful as hybridization probes or PCR primers generally need not encode a biologically active portion of a mannan synthase protein.

A fragment of a galactosyltransferase nucleotide sequence that encodes a biologically active portion of a galactosyltransferase protein of the invention will encode at least 15, 25, 30, 50, 100, 150, 200, 300, 350, or, 400 contiguous amino acids, or up to the total number of amino acids present in a full-length mannan synthase protein of the invention (for example, 445 amino acids for SEQ ID NO:4). Fragments of a galactosyltransferase nucleotide sequence or galactosyltransferase that are useful as hybridization probes or PCR primers generally need not encode a biologically active portion of a galactosyltransferase protein.

Thus, a fragment of a mannan synthase nucleotide sequence may encode a biologically active portion of a mannan synthase protein, or it may be a fragment that can be used as a hybridization probe or PCR primer using methods disclosed below. A biologically active portion of a mannan synthase protein can be prepared by isolating a portion of one of the mannan synthase nucleotide sequences of the invention, expressing the encoded portion of the mannan synthase protein (e.g., by recombinant expression in vitro), and assessing the activity of the encoded portion of the mannan synthase protein. Nucleic acid molecules that are fragments of a mannan synthase nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, 1,400, 1,500, 1,600, 1,700, 1,800, 1,900 or 1,950 nucleotides, or up to the number of nucleotides present in a full-length mannan synthase nucleotide sequence disclosed herein (for example, 1964 nucleotides for SEQ ID NO:1).

Similarly, a fragment of galactosyltransferase nucleotide sequence may encode a biologically active portion of a galactosyltransferase protein, or it may be a fragment that can be used as a hybridization probe or PCR primer using methods disclosed below. A biologically active portion of a galactosyltransferase protein has galactosyltransferase activity, particularly galactosyltransferase activity that comprises the transfer of galactosyl residues in the biosynthesis of galactomannan polysaccharides. Such a biologically active portion of a galactosyltransferase protein can be prepared by isolating a portion of one of the galactosyltransferase nucleotide sequences of the invention, expressing the encoded portion of the galactosyltransferase protein (e.g., by recombinant expression in vitro), and assessing the activity of the encoded portion of the galactosyltransferase protein. Nucleic acid molecules that are fragments of a galactosyltransferase nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, or 1,400 nucleotides, or up to the number of nucleotides present in a full-length galactosyltransferase nucleotide sequence disclosed herein (for example, 1609 nucleotides for SEQ ID NO:3).

By "variants" is intended substantially similar sequences. For nucleotide sequences, conservative variants include those sequences that, because of the degeneracy of the genetic code, encode the amino acid sequence of one of the mannan synthase polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a mannan synthase or galactosyltransferase protein of the invention. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, mannan synthase or galactosyltransferase activity as described herein. Such variants may result from, for example, genetic polymorphism or from human manipulation. Biologically active variants of a native mannan synthase protein of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the mannan synthase or galactosyltransferase proteins can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired mannan synthase or galactosyltransferase activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by measuring mannan synthase or galactosyltransferase activity. See, for example, Edwards et al. (1989) *Planta* 178:41-51, herein incorporated by reference.

Variant nucleotide sequences and proteins also encompass sequences and proteins derived from a mutagenic and recombinogenic procedure such as DNA shuffling. With such a procedure, one or more different mannan synthase coding sequences can be manipulated to create a new mannan synthase protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the mannan synthase nucleotide sequence of the invention and other known nucleotide sequences to obtain a new nucleotide sequence coding for a protein with an improved property of interest, such as an increased Vmax and/or reduced $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can be used to isolate corresponding sequences from other organisms, particularly other plants. In this manner, methods such as PCR, hybridization, and the like can be used to identify such sequences based on their sequence homology to the sequence set forth herein. Sequences isolated based on their sequence identity to the entire mannan synthase or galactosyltransferase sequence set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated sequences that encode for an mannan synthase or galactosyltransferase protein and which hybridize under stringent conditions to the mannan synthase sequence galactosyltransferase sequence disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the ManS1 and GalT2 sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire ManS1 or GalT2 sequence disclosed herein, or one or more portions thereof, may be used as a probe capable of specifically hybridizing to corresponding mannan synthase and β-galactosyltransferase nucleotide sequences and messenger RNAs, respectively. To achieve specific hybridization under a variety of conditions, such probes include sequences that are unique among mannan synthase (β-glycosyltransferase) and β-galactosyltransferase sequences and are preferably at least about 10 nucleotides in length, and most preferably at least about 20 nucleotides in length. Such probes may be used to amplify corresponding mannan synthase and β-glycosyltransferase sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1X SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology-Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Nat. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. Alignment may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10,15, 20, 25, 30, 35,40,45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443-453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778; herein incorporated by reference.

The mannan synthase and galactosyltransferase nucleotide sequences of the invention are provided in expression cassettes for expression in the plant of interest. The cassette will include 5' and 3' regulatory sequences operably linked to a mannan synthase or galactosyltransferase nucleotide sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the mannan synthase or galactosyltransferase nucleotide sequence to be under the transcriptional regulation of the regulatory regions. The expression cassette may additionally contain selectable marker genes.

The expression cassette will include in the 5'-3' direction of transcription, a transcriptional and translational initiation region (i.e., a promoter), a mannan synthase or galactosyltransferase nucleotide sequence of the invention, and a transcriptional and translational termination region (i.e., termination region) functional in plants. The promoter may be native or analogous, or foreign or heterologous, to the plant host and/or to the mannan synthase or galactosyltransferase nucleotide sequence of the invention. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the mannan synthase or galactosyltransferase nucleotide sequence of the invention, it is intended that the promoter is not the native or naturally occurring promoter for the operably linked mannan synthase or galactosyltransferase nucleotide sequence of the invention. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would change expression levels of mannan synthase or galactosyltransferase in the plant or plant cell. Thus, the phenotype of the plant or plant cell is altered.

The termination region may be native with the transcriptional initiation region, may be native with the operably linked mannan synthase or galactosyltransferase nucleotide sequence of interest, may be native with the plant host, or may be derived from another source (i.e., foreign or heterologous to the promoter, the mannan synthase or galactosyltransferase nucleotide sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

A number of promoters can be used in the practice of the invention. The promoters can be selected based on the desired outcome. The nucleic acids can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No.

6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced mannan synthase and/or galactosyltransferase expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-specific promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing non-legume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol.*

Biol. 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and CesA (cellulose synthase) (see WO 00/11177, herein incorporated by reference). Gama-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, δ-zein, waxy, shrunken 1, shrunken 2, globulin 1, etc. See also WO 00/12733, where seed-preferred promoters from end1 and end2 genes are disclosed; herein incorporated by reference.

Where low level expression is desired, weak promoters will be used. Generally, by "weak promoter" is intended a promoter that drives expression of a coding sequence at a low level. By low level is intended at levels of about $1/1000$ transcripts to about $1/100,000$ transcripts to about $1/500,000$ transcripts. Alternatively, it is recognized that weak promoters also encompass promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

The methods of the invention involve introducing a nucleotide construct into a plant. By "introducing" is intended presenting to the plant the nucleotide construct in such a manner that the construct gains access to the interior of a cell of the plant. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, Agrobacterium-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

The nucleotide constructs of the invention may be introduced into plants by contacting plants with a virus or viral nucleic acids. Generally, such methods involve incorporating a nucleotide construct of the invention within a viral DNA or RNA molecule. It is recognized that the mannan synthase and/or galactosyltransferase of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

It is recognized that with these nucleotide sequences, antisense constructions, complementary to at least a portion of the messenger RNA (mRNA) for the mannan synthase or galactosyltransferase nucleotide sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The present invention may be used for transformation of any plant species, including, but not limited to, monocots and dicots. Examples of plant species of interest include, but are not limited to, corn (*Zea mays*), *Brassica* sp. (e.g., *B. napus*, *B. rapa*, *B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants.

Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

In contrast to starch, which is deposited in the amyloplasts in the seed, seed gums are deposited as secondary thickenings on the walls of the endosperm cells by apposition (Reid (1985) *Adv. Bot. Res.* 11:125-155; Reid et al. (1995) *Planta* 195:489-495; Reid et al. (1992) *Biochemical Society Transactions* 20:23-26; Reid et al. (1987) *Food Hydrocolloids* 1:381-386). Seed-derived gums are classified into two main categories: galactomannans and xylogucans. Galactomannan, a linear polymer of mannosyl residues which is substituted to varying degrees by galactosyl residues, is a major constituent of the seeds of guar, fenugreek, and locust bean (Reid (1985) *Adv. Bot. Res.* 11:125-155; Bayerlein (1993) *Technical applications of galactomannans. In Plant polymeric carbohydrates*, Meuser Manners, and Seibel eds., The Royal Society of Chemistry, Cambridge, pp. 191-202).

The differences in the properties of the galactomannan seed gums are determined by the mannose/galactose ratio in the polysaccharides, which ranges from a low of ~2 in guar to a high of 4 in locust bean. Locust bean gum is considered to be of highest quality of the seed gums for industrial applications. Bayerlein (1993) *Technical applications of galactomannans. In Plant polymeric carbohydrates*, Meuser Manners, and Seibel eds., The Royal Society of Chemistry, Cambridge, pp. 191-202. Aside from the intrinsic properties of the galactosyltransferase, the degree of galactosylation could also be influenced by another enzyme, alpha-galactosidase, which is expressed in the seeds of the species with low degree of galactomannan galactosylation (Edwards et al. (1992) *Planta* 187:67-74; Joersbo et al. (2001) *Molecular Breeding* 7:211-219). Alpha-galactosidase is not expressed in developing guar seeds.

Plant cell wall polysaccharides, including seed gums, are synthesized in two compartments. Cellulose and callose are made at the plasma membrane. The remaining cell wall polysaccharides are synthesized in the Golgi and then exported to the cell wall by exocytosis (Ray et al. (1976) *Ber. Deutsch. Bot. Ges. Bd.* 89:121-146; Ray et al. (1969) *Proc. Natl. Acad. Sci. USA.* 64:605-612; Ray (1979). Maize coleoptile cellular membranes bearing different types of glucan synthetase activity. In *Plant Organelles*, Reid, ed. Halsted Press/John Wiley & Sons, Chichestor, U.K., pp. 135-146). Given a large variety of sugars that constitute cell wall and the complexity of chemical linkages holding these sugars, there must be tens, if not hundreds, of glycosyltransferases (glucan synthases) in the Golgi apparatus (Carpita (1996) *Ann. Rev. Plant Physiol. And Plant Mol. Bio.* 47:445-476).

Although the physicochemical properties of gum polysaccharides and their mixtures have been extensively characterized (Ganter et al. (1995) *Intl. J. Bio. Macromolecules* 17:13-19; Ikuta et al. (1997) *Biochem. J.* 323:297-305; Kapoor et al. (1989) *Indian J. Chem., Section B* 28:928-933; Kapoor et al. (1995) *Carbohydrate Polymers* 27:229-233; Latge et al. (1994) *Infection and Immunity* 62:5424-5433. McCutchen et al. (1996) *Biotech. Bioeng.* 52:332-339; Damasio et al. (1990) *Food Hydrocolloids* 3:457-464; Patel et al. (1989) *Starch* 41:192-196; Bulpin et al. (1990) *Carbohydrate Polymers* 12:155-168; Davis et al. (1995) *Carbohydrate Research* 271:43-54; Stading (1993) *Carbohydrate Polymers* 22:49-56; Lopes et al. (1992) *J. Food Sci.* 57:443-448; Mannion et al. (1992) *Carbohydrate Polymers* 19:91-97), only a limited amount of work has gone into studying their synthesis (Reid et al. (1995) *Planta* 195:489-495; Reid et al. (1992) *Biochemical Society Transactions* 20:23-26; Reid et al. (1987) *Food Hydrocolloids* 1:381-386; Edwards et al. (1992) *Planta* 187:67-74; Campbell and Reid (1982) *Planta* 155:105-111; Edwards et al. (1989) *Planta* 178:41-51). It is known that the substrates for galactomannan synthesis are GDP-mannose and UDP-galactose, the $K_M$ of respective enzymes for each substrate is approximately 10 µM, coincubation of the enzyme preparation with both substrates is needed for galactomannan formation, although mannan can be formed in the absence of UDP-galactose. Enzyme activity peaks around 35-45 days after flowering in fenugreek and guar seeds, and both enzyme activities are membrane-bound and are located on an intracellular compartment (Reid et al. (1995) *Planta* 195:489-495; Campbell and Reid (1982) *Planta* 155:105-111; Edwards et al. (1989) *Planta* 178:41-51).

The gene for one of the galactosyltransferases, the enzyme that transfers one sugar at a time to the sixth position of the mannosyl residues in the mannan backbone, was isolated following biochemical purification; (Edwards et al. (1999) *Plant J.* 19:691-697). The ability to solubilize this enzyme in active from even in Triton-X100, which completely destroys mannan synthase activity, was what allowed the isolation of this gene. Following the enzyme purification approach, Perrin et al. similarly isolated a fucosyltransferase from pea cells (Perrin Robyn et al. (1999). *Science* 284:1976-1979). A gene for a component of the Golgi-associated xyloglucan synthase was isolated after the biochemical purification of the corresponding polypeptide (Dhugga et al. (1997) *Proc. Natl. Acad. Sci. USA* 94:7679-7684).

The breakthrough in the isolation of a plant cellulose synthase came via the genomics approach when Pear et al. isolated a gene for cellulose synthase from developing cotton fibers after sequencing only a few hundred cDNA clones, a discovery that was made possible by the cloning of a gene for a bacterial cellulose synthase earlier (Pear et al. (1996) *Proc. Natl. Acad. Sci. USA* 93:12637-12642; Saxena et al. (1990) *Plant Mol. Biol.* 15:673-684). Even though the homology over the entire derived polypeptide was weak, some domains were highly conserved so as to allow the identification of the plant sequence as a cellulose synthase. Isolation of the plant cellulose synthase gene allowed annotation of a large number of related genes from other species in genomic databases (Dhugga, K. S. (2001). Building the wall: genes and enzyme complexes for polysaccharide synthases. *Curr. Opin. Plant Biol.* 4, 488-493. Richmond Todd, A., and Somerville Chris, R. (2000). The cellulose synthase superfamily. *Plant-Physiology*-124, 495-498.).

Now that the *Arabidopsis* genome has been completely sequenced, a complete set of genes homologous to the cellulose synthase gene has been identified (The *Arabidopsis* Initiative (2000) *Nature* 408:796-815). From a total of 40 genes, 10 encode cellulose synthase catalytic subunit (CesA) and the remaining 30 encode cellulose synthase-like (Csl) proteins (The *Arabidopsis* Initiative (2000) *Nature* 408:796-815). All the processive beta-glycosyltransferases, i.e., the ones involved in polymer formation instead of individual sugar transfer, have several aspartyl residues and a QXXRW motif conserved among them (Saxena and Brown (2000) *Curr. Opin. Plant-Biol.* 3:523-531). These conserved motifs provide useful handles in identifying beta-glycosyltransferases from other sources.

In general, the genes for cellulose synthase are present at a relatively low level of approximately 0.05% of the expressed genes (Dhugga (2001) *Curr. Opin. Plant Biol.* 4:488-493). The genomics approach for the isolation of a cellulose synthase gene succeeded in plants because of the choice of tissue used for EST sequencing. Developing cotton fibers make primarily cellulose during the phase of secondary wall formation. After the gene was isolated, the cellulose synthase seemed to be expressed at approximately 0.5% level in these fibers, which is an order of magnitude greater than in other tissues (Pear et al. (1996) *Proc. Nat. Acad. Sci. USA* 93:12637-12642). A similar strategy was employed to isolate the genes for galactomannan formation disclosed herein from developing guar seeds after attempts with a biochemical approach were partially successful.

EXPERIMENTAL

Example 1

Membrane Isolation and Enzyme Assay

Plant Material

Guar pods were harvested either from the greenhouse or field-grown plants at different developmental stages. Seeds were mechanically removed from their pods using a modified pea sheller (Taylor Manufacturing Co., Inc., Moutrie, Ga. 31776). Washed seeds were homogenized in three volumes of cold homogenization buffer containing 50 mM HEPES, pH 7.5, 4% (w/v) sucrose, 1% (w/v) glycerol, 5 mM KCl, 5 mM mercaptoethanol, and 2 mM EDTA. Immediately after homogenization, the slurry was squeezed through one layer of Miracloth (Calbiochem cat.# 475855) and four layers of cheesecloth (VWR cat. # 21910-105) to remove cell walls and other debris. Filtered residues were washed three times with cold buffer using the same filtration procedure. Filtrates ($H_1$) were centrifuged at 1000×g at 4° C. for 15 min in a Beckman Avanti J-20 I centrifuge. The resulting pellets ($P_1$) were discarded, saving the supernatants for further centrifugation at 142,000×g for 40 min at 4° C. using an ultracentrifuge (Beckman Coulter, Optima LE-80K).

The resulting high speed pellet was resuspended in one volume of dilution buffer (100 mM HEPES pH 7.5, 10 mM DTT, 10% (w/w) glycerol, and 1 mM EDTA) using a glass homogenizer (Kontes, N.J. 08360). Resuspended pellets (P$_2$) were stored in liquid N$_2$.

Enzyme Kinetics

Pellet from the previous steps was re-suspended in 3 volumes of dilution buffer using a glass homogenizer. An aliquot was removed and protein was determined ($\cong$10 mg/mL) by the BCA method (Pierce cat. # 23226). GDP-mannose:mannosyl transferase reaction mix was modified from Edwards et al. (1989) *Planta* 178:41-51. The enzymatic assays were performed on 40 μL resuspended pellet (400 μg protein) by adding 10 μL of reaction mix which rendered a final concentration of 80 μM GDP-mannose, 2.5 mM DTT, 2.5 mM MgCl$_2$, 5 mM MnCl$_2$, and 6% glycerol (w/w) in 100 mM Hepes buffer pH 7.5. The specific activity of the reaction mix was 83.33 Bq nmol$^{-1}$ of GDP-mannose. Unless indicated otherwise, reactions were incubated in a water bath at 35° C. for 40 min, including the blanks.

Reactions were stopped by adding 2 mL of stopping solution containing 70% ethanol and 2 mM EDTA. The quenched mixtures were passed through GF/A glass microfiber filter discs, 24 mm in diameter (Cat. # 1820 024, Whatman Intl. Ltd., Maidstone, England). Filters were subsequently washed with 15 mL stopping solution. The radioactivity retained by the filters was measured in vials with 3 mL scintillation cocktail (Scintiverse) using a liquid scintillation analyzer (Packard Tri-Carb 2900 TR).

For kinetic analyses, in the experiments with different substrate (GDP-mannose) concentrations, the specific radioactivity of the reaction mix was normalized at 83.33 Bq nmol$^{-1}$. Data from kinetic experiments were fitted to a Michaelis-Menten model using the Marquardt-Levenberg algorithm with a simple weighing method. Reactions were carried out with GDP-mannose concentrations from 0 to 200 μM. The calculated Km is:

$$K_{m\ (GDP\text{-}mannose)} = 8.98 \pm 3.6\ \mu M$$

Time Course of Substrate Incorporation Into Product:

Linearity of the reaction over time at 35° C. and 80 μM GDP-mannose was tested with a time course. The reaction mixture used had a specific activity of 83.33 nmol$^{-1}$. High speed pellets from guar seeds harvested at 25 days after flowering were resuspended in suspension buffer to obtain a protein concentration of 6.05±0.8 mg mL$^{-1}$. Forty μL of this suspension were added to the reaction mix.

From the time course experimental data (activity vs Rx time), the flux of mannose incorporated onto the polymer chain can be estimated according to the following equation: Slope/Specific Radio Activity=30 DPM min$^{-1}$/5000 DPM nmol$^{-1}$=0.006 nmoles min$^{-1}$ 40 μL suspension.

Since 40 μL of suspension contained 242 μg of total protein, then the specific activity equals 25 pmoles mannose incorporated min$^{-1}$ mg$^{-1}$ protein.

Digitonin Series for Enzyme Solubilization:

The aim of this experiment was to find the optimal digitonin concentration to achieve maximum solubilization of membrane proteins while minimizing enzymatic inactivation.

High speed pellets from guar seeds (P$_2$) were resuspended in 3 volumes of dilution buffer and 0.3% w/w digitonin (Fluka, cat. # 37008) and incubated in a nutator (Thermolyne, mod. Varimix) during 15 min at 4° C. to remove peripheral proteins. The resulting suspension was centrifuged at 142,000×g at 4° C. for 40 min using a bench-top ultracentrifuge (Beckman Coulter, Optima Max). High speed pellets were resuspended in one volume of dilution buffer and aliquoted into 50 μL fractions. Each aliquot was then further diluted with dilution buffer and different digitonin concentrations. After two hours incubation in a nutator at 4° C., detergent-solubilized particles were centrifuged again at 142,000×g for 40 minutes at 4° C. and both pellets and supernatants were saved for enzymatic analysis.

Glycerol Gradient Centrifugation of the Solubilized Guar Seed Particles:

High speed particles from guar seeds stored in liquid N$_2$ (P$_2$) were resuspended in 3 volumes of dilution buffer and incubated during 15 min at 4° C. with 0.3% digitonin. The suspension was then centrifuged at 142,000×g at 4° C. for 40 min and the pellets were subsequently diluted as in the previous step and treated with 3% digitonin to solubilize integral membrane proteins. After two hours incubation in a nutator at 4° C., detergent-solubilized particles were centrifuged again at 142,000×g for 40 minutes and the supernatant was saved to be loaded onto a continuous glycerol gradient (20-60% w/w), and centrifuged at 207,000×g for 18 hours at 4° C. After centrifugation, the gradients were fractionated in 1 mL fractions and mannan synthase activity was measured in each fraction using a 40 μL aliquot from each tube in duplicates. Reaction mixtures for GDP-mannosyl transferase consisted of 100 mM HEPES, pH 7.5, 5 mM DTT, 2.5 mM MgCl$_2$, 5 mM MnCl$_2$, 6% w/w glycerol, 5 μM cold GDP-mannose, and 20,000 dpm/10 μL. The enzymatic reaction was incubated at 33° C. for 40 min and quenched with 2 mL of stopping buffer.

Example 2

Fractionation of the Digitonin-Solubilized Mannan Synthase from Guar Seeds on a Glycerol Gradient Digitonin-solubilized membrane preparation was subjected to isopycnic centrifugation, fractions collected, and assayed for mannan synthase and callose synthase activities. FIG. 5 shows the separation of the two activities. Whereas mannan synthase is associated with the Golgi compartment, callose synthase is bound to the plasma membrane.

Figure 6:
FIG. 6 is a photographic illustration of the results of two-dimensional gels from different fractions of the gradient depicted in FIG. 5. The polypeptides that show a correlation with the mannan synthase activity are circled.

Fractions 5, 8, and 10 were separated on 2-D gels. Several polypeptides, as seen from the staining intensity, were identified to correlate with the mannan synthase activity (FIG. 6).

Example 3

Construction of an EST Database for Developing Guar Seed

A database for developing guar seed was set up with approximately 5000 ESTs from each of the three developmental stages (Table 1). Quality of the database is judged from the degree of redundancy as shown by the % distinct column; fifty-five percent of the sequences in each library were distinct. When all three libraries are taken as a group, the number of percent distinct ESTs went down because of the same ESTs being represented in different libraries. Sixty-five percent of the ESTs assembled into contigs, leaving approximately 35% as singlets (Table 2)

TABLE 1

EST Database for Developing Guar Seeds

| Library | Description | Size | Distinct | % Distinct | % Unique | % Singlets |
|---------|-------------|------|----------|------------|----------|------------|
| lds1c | 10 DAF* whole seeds | 4892 | 2590 | 52.9 | 36.5 | 33.2 |
| lds2c | 20–25 DAF endosperm | 4824 | 2696 | 55.9 | 38.3 | 33.6 |
| lds3c | 30–35 DAF whole seeds | 5079 | 2921 | 57.5 | 40.2 | 37.5 |
| GROUP | | 14795 | 6790 | 45.9 | | 34.8 |

*DAF, days after flowering

TABLE 2

EST Counts for ManS, GalT1 and GalT2 from EST Database from Developing Guar Seeds

| | EST count | | | |
|---|---|---|---|---|
| Gene | 15 DAF | 25 DAF | 35 DAF | Total |
| ManS | 0 | 12 | 2 | 14 |
| GalT1 | 0 | 38 | 1 | 39 |
| GalT2 | 1 | 12 | 0 | 13 |

*DAF, days after flowering

Example 4

Identification of Putative Mannan Synthase (CtManS) and Galactosyltransferase (CtGalT) Genes from Guar (*Cyamopsis Tetragonoloba*)

Two types of glycosyltransferases enzymes are present in living cells: soluble and membrane-bound. The soluble enzymes are mostly used in glycosylating small molecules, such as phytohormones and monolignols. The membrane-bound enzymes further consist of two types: the ones that catalyze the formation of a polymer and are called processive enzymes, and the ones that generally transfer a single sugar to an existing polysaccharide. Whereas mannan synthase is a processive enzyme, galactosyltransferases are simple transferases. A gene for galactosyltransferase that transfers galactosyl residues to mannan backbone was isolated from the seeds of fenugreek following the biochemical approach (Edwards et al. (1999) *Plant J.* 19:691-697). We used homology comparison to isolate two different genes from guar seed libraries. The nucleotide and amino acid sequence alignments are shown in FIGS. 7 and 8, respectively. GalT1 is 70% identical over the entire sequence to the fenugreek sequence at the nucleotide sequence level. GalT2 shows only 56% identity to both GalT1 as well as fenugreek galactosyltransferase at the nucleotide sequence level.

Example 5

Identification of Mannan Synthase Gene

Several motifs including DXD (positions 189-191 in ManS), D (position 283), and QXXRW (positions 319-323) that are diagnostic of the processive beta-glycosyltransferases are also conserved in the mannan synthase polypeptide as is shown in FIG. 9.

Example 6

Characteristics of the Derived Amino Acid Sequences

Figure 10:
FIG. 10 depicts the approximate location of transmembrane domains (light grey) in the guar mannan synthase (upper) and guar galactosyltransferase (lower) polypeptides of the invention.

Below are provided biochemical characteristics of the derived amino acid sequences of the components of the galactomannan synthesis machinery (see Table 3). Both the galactosyltransferases were identified by their homology to the previously isolated gene from fenugreek (Edwards et al. (1999) *Plant J.* 19:691-697). Mannan synthase was identified by the presence of conserved amino acid motifs that are found in other, known processive beta-1,4-glycosyltransferases, and the presence of transmembrane domains. GalT1 and GalT2 each have a single transmembrane domain near the N-terminus whereas ManS has three transmembrane domains. Their approximate locations are shown in FIG. 10.

TABLE 3

Characteristics of ManS, GalT1, and GalT2.

| Enzyme | Amino acids | MW* | pI† | Identity to fenugreek GALT (%) | Similarity to fenugreek GALT (%) |
|--------|-------------|-----|-----|-------------------------------|---------------------------------|
| MANS | 526 | 60,673 | 9.28 | — | — |
| GALT1 | 435 | 50,952 | 8.02 | 73 | 83 |
| GALT2 | 445 | 51,642 | 6.26 | 61 | 74 |

*MW, molecular weight;
†pI, isoelectric point.

Example 7

Expression Pattern of the Genes for Galactomannan Synthesis from Guar Seeds

Northern blots containing RNA from different tissues were probed with respective dig-labeled probes using methods known to those of ordinary skill in the art.

Figure 11:
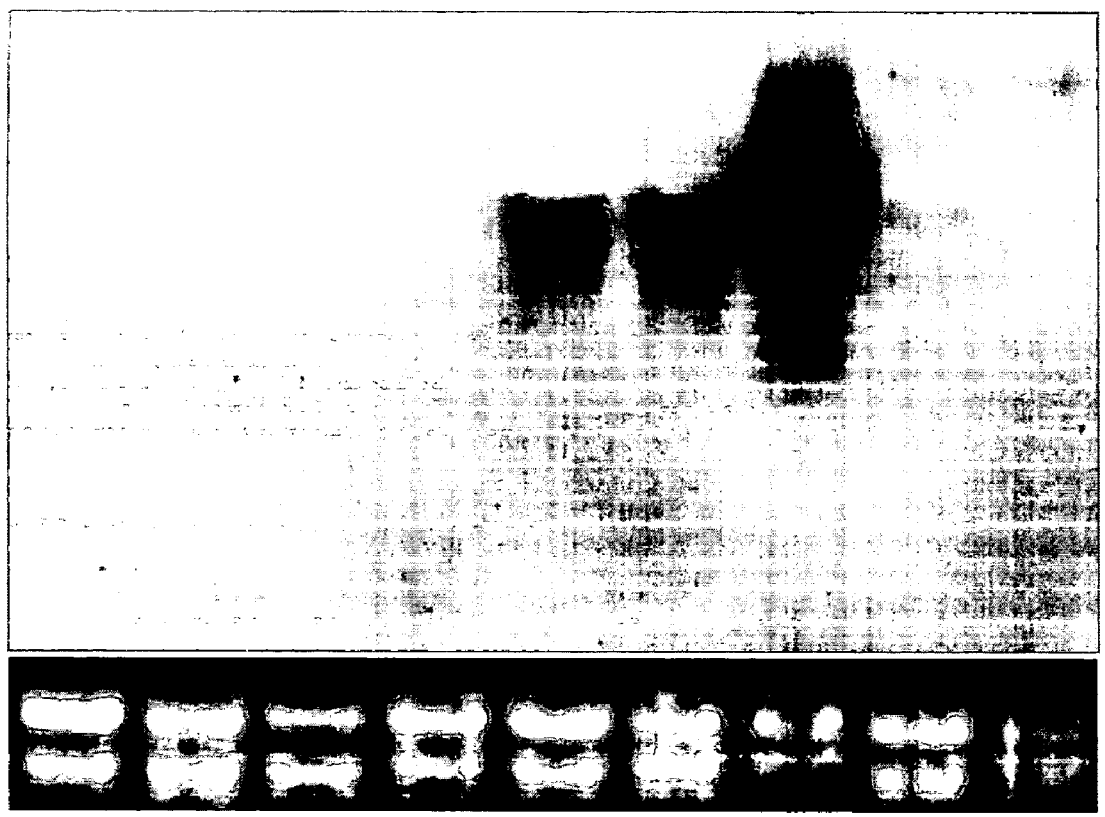
FIG. 11 shows the results of a Northern blot analysis of the expression of mannan synthase gene in different guar tissues (above) and ethidium bromide-stained portion of the gel corresponding to the large and small ribosomal RNA subunits as an RNA control (under each of the Northern blots). Lanes: R, young roots; S, young stem; L, young leaves; 10, 10 days after flowering (DAF) seeds; 25, 25 DAF seeds; 30, 30 DAF seeds; E, endosperm from 25 DAF seeds; SC, seeds coat from 25 DAF seeds; Em, embryo from 25 DAF seeds.

The results of the northern blot analysis indicted that the mannan synthase gene is expressed only in the developing seed endosperm and no other tissue (FIG. 11). This expression pattern is similar to that of mannan synthase enzyme activity. The specificity of expression agrees well with the presence of galactomannan in the endosperm.

Example 8

Expression of Galactosyltransferase Genes in Guar Tissue

Northern blots containing RNA from different tissues were probed with respective dig-labeled probes using methods known to those of ordinary skill in the art.

Figure 12A:
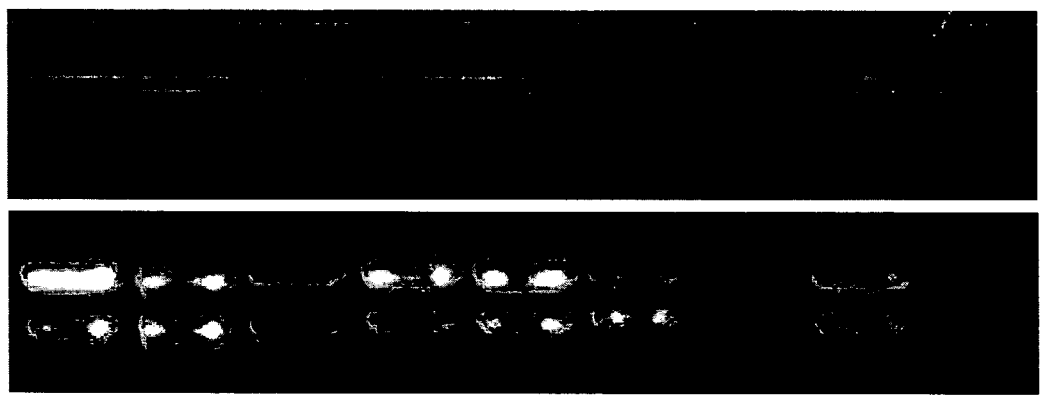
FIG. 12 depicts the results of a Northern blot analysis of the expression of galactosyltransferase genes (GalT1 in 12A and GalT2 in 12B) in different guar tissues (above) and ethidium bromide-stained portion of the gel corresponding to the large and small ribosomal RNA subunits as an RNA control (under each of the Northern blots). Lanes: R, young roots; S, young stem; L, young leaves; 10, 10 DAF seeds; 25, 25 DAF seeds; 30, 30 DAF seeds; E, endosperm from 25 DAF seeds; SC, seeds coat from 25 DAF seeds; Em, embryo from 25 DAF seeds.
Figure 12B:
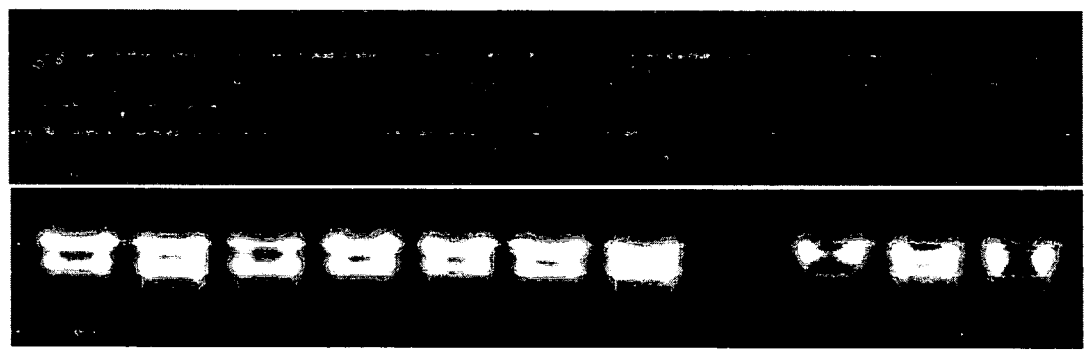
Figure 13:
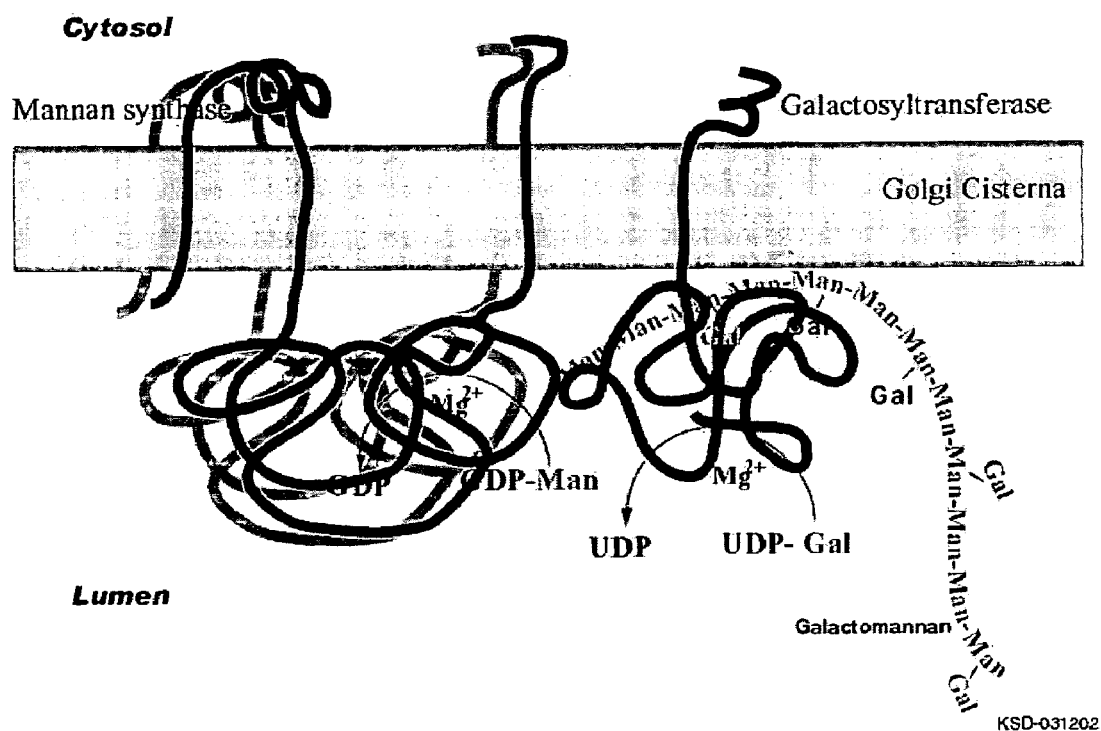
FIG. 13 is a graphical illustration for the model for the subcellular location of mannan synthase (galactomannan synthase) and galactosyltransferase for the synthesis of galactomannan in plant cells.

Like mannan synthase, both the galactosyltransferase sequences are expressed only in the endosperm of the developing seed, indicating that these enzymes are involved in galactomannan formation in guar seeds (FIG. 12).

Example 9

Model for Mannan Synthase

While not to be bound by any particular theory, a model for a functional minimal mannan synthase was constructed on the basis the number of predicted transmembrane domains in mannan synthase and galactosyltransferase (FIG.

13). The catalytic domain containing the QXXRW motif is projected into the Golgi lumen. Since a beta linkage requires an 180 degree rotation of the adjacent glycosyl residues, a model has been proposed where two enzyme polypeptides have their catalytic sites juxtaposed to each other with each transferring alternate sugars to the elongating mannan chain (Dhugga (2001) *Curr. Opin. Plant Biol.* 4:488-493). Given the species-specific mannose/galactose ratio, galactosyltransferase polypeptide is expected to be either directly associated with mannan synthase or is maintained in close proximity.

Example 10

Transformation of Somatic Soybean Embryo Cultures

Soybean embryogenic suspension cultures were maintained in 35 ml liquid media (SB55 or SBP6) on a rotary shaker, 150 rpm, at 28° C. with mixed fluorescent and incandescent lights on a 16.8 h day/night schedule. Cultures were subcultured every four weeks by inoculating approximately 35 mg of tissue into 35 ml of liquid medium. Media recipes and stock solutions for making media are listed in Table 4.

TABLE 4

Stock Solutions and Media Recipes for Transformation of Soybean Somatic Embryo Cultures Stock Solutions (g/L):
MS Sulfate 100 × Stock

| | |
|---|---|
| $MgSO_4$ $7H_2O$ | 37.0 |
| $MnSO_4$ $H_2O$ | 1.69 |
| $ZnSO_4$ $7H_2O$ | 0.86 |
| $CuSO_4$ $5H_2O$ | 0.0025 |

MS Halides 100 × Stock

| | |
|---|---|
| $CaCl_2$ $2H_2O$ | 44.0 |
| KI | 0.083 |
| $CoCl_2$ $6H_2O$ | 0.00125 |
| $KH_2PO_4$ | 17.0 |
| $H_3BO_3$ | 0.62 |
| $Na_2MoO_4$ $2H_2O$ | 0.025 |

MS FeEDTA 100 × Stock

| | |
|---|---|
| $Na_2EDTA$ | 3.724 |
| $FeSO_4$ $7H_2O$ | 2.784 |

B5 Vitamin Stock 10 g m-inositol
100 mg nicotinic acid
100 mg pyridoxine HCl
1 g thiamine SB55 (per Liter, pH 5.7)

10 mL each MS stocks
1 mL B5 Vitamin stock
0.8 g $NH_4NO_3$
3.033 g $KNO_3$
1 mL 2,4-D (10 mg/mL stock)
60 g sucrose
0.667 g asparagine

SBP6 same as SB55 except 0.5 mL 2,4-D

SB103 (per Liter, pH 5.7)

1 × MS Salts
6% maltose
750 mg $MgCl_2$
0.2% Gelrite

TABLE 4-continued

Stock Solutions and Media Recipes for Transformation of Soybean Somatic Embryo Cultures SB71-1 (per Liter, pH 5.7)

1 × B5 salts
1 ml B5 vitamin stock
3% sucrose
750 mg $MgCl_2$
0.2% Gelrite

Soybean embryogenic suspension cultures were transformed with a plasmid comprising the mannan synthase nucleotide sequence (SEQ ID NO:1) operably linked to the β-conglycinin promoter and the phaseolin gene 3' terminator region. The plasmid additionally contained a selectable marker gene comprising a constitutive promoter operably linked for the expression the coding sequence for hygromycin phosphotransferase. The cultures were transformed by particle-gun bombardment (Klein et al. (1987) *Nature* 327: 70). A DuPont Biolistic PDS1000/HE instrument (helium retrofit) was used for these transformations. To 50 ml of a 60 mg/ml 1 µm gold particle suspension is added (in order); 5 µl DNA(1 µg/µl), 20 µl spermidine (0.1 M), and 50 µl $CaCl_2$ (2.5 M). The particle preparation was agitated for 3 min, spun in a microfuge for 10 sec and the supernatant removed. The DNA-coated particles were then washed once in 400 µl 70% ethanol and re-suspended in 40 µl of anhydrous ethanol. The DNA/particle suspension was sonicated three times for 1 sec each. Five µl of the DNA-coated gold particles are then loaded on each macro carrier disk. For selection, a plasmid conferring resistance to hygromycin phosphotransferase (HPT) can be co-bombarded with the silencing construct of interest.

Approximately 300-400 mg of a four-week-old suspension culture was placed in an empty 60×15 mm petri dish and the residual liquid removed from the tissue with a pipette. For each transformation experiment, approximately 5-10 plates of tissue were bombarded. Membrane rupture pressure was set at 1000 psi and the chamber was evacuated to a vacuum of 28 inches of mercury. The tissue was placed approximately 3.5 inches away from the retaining screen and bombarded three times. Following bombardment, the tissue was placed back into liquid and cultured as described above.

Eleven days post bombardment, the liquid media was exchanged with fresh SB55 containing 50 mg/ml hygromycin. The selective media was refreshed weekly. Seven weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Thus each new line was treated as an independent transformation event. These suspensions can then be maintained as suspensions of embryos maintained in an immature developmental stage or regenerated into whole plants by maturation and germination of individual somatic embryos.

Independent lines of transformed embryogenic clusters were removed from liquid culture and placed on a solid agar media (SB103) containing no hormones or antibiotics. Embryos were cultured for four weeks at 26° C. with mixed fluorescent and incandescent lights on a 16:8 h day/night schedule. During this period, individual embryos were removed from the clusters and analyzed.

The plasmids used in these experiments were made using standard cloning methods well known to those skilled in the art (Sambrook et al. (1989) *Molecular Cloning*, CSHL Press, New York). A starting plasmid pKS18HH (U.S. Pat. No. 5,846,784, hereby herein incorporated in its entirety by reference) contains a hygromycin B phosphotransferase (HPT) obtained from *E. coli* strain W677 under the control of a T7 promoter and the 35S cauliflower mosaic virus promoter. Plasmid pKS18HH thus contains the T7 promoter/HPT/T7 terminator cassette for expression of the HPT enzyme in certain strains of *E. coli*, such as NovaBlue(DE3) [from Novagen], that are lysogenic for lambda DE3 (which carries the T7 RNA Polymerase gene under lacV5 control). Plasmid pKS18HH also contains the 35S/HPT/NOS cassette for constitutive expression of the HPT enzyme in plants, such as soybean. These two expression systems allow selection for growth in the presence of hygromycin to be used as a means of identifying cells that contain the plasmid in both bacterial and plant systems. pKS18HH also contains three unique restriction endonuclease sites suitable for the cloning other chimeric genes into this vector. Plasmid ZBL100 (PCT Application No. WO 00/11176 published on Mar. 2, 2000) is a derivative of pKS18HH with a reduced NOS 3' terminator. Plasmid pKS67 is a ZBL100 derivative with the insertion of a beta-conglycinin promoter, in front of a NotI cloning site, followed by a phaseolin 3' terminator (described in WO 94/11516, published on May 26, 1994, hereby herein incorporated in its entirety by reference). The plasmid pKS211 is a derivative of pKS67 with the guar mannan synthase gene inserted into the Not I site.

Example 11

Figure 14:
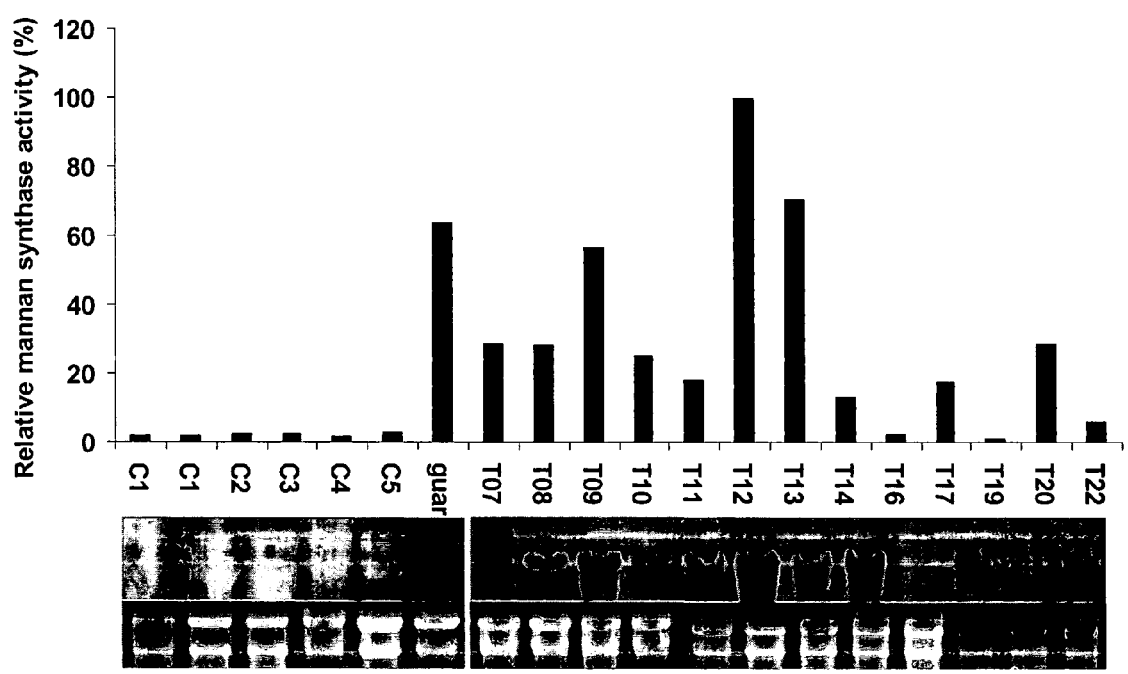
FIG. 14 depicts an activity profile (upper panel) and the results of a Northern blot analysis of the control and transgenic soybean somatic embryos (middle panel). The lower panel depicts ethidium bromide-stained portions of the corresponding rRNA gels showing the relative amount of RNA in each lane.

Determination of Mannan Synthase Activity from Transgenic Soybean Somatic Embryos Mannan synthase activity was assayed as previously described on the membrane fractions isolated from embryos. The control embryos had a background activity of 3-4 pmol per min per mg of the membrane protein(FIG. 14). Guar was included as a positive control. Every transgenic event expressing the mannan synthase gene also had mannan synthase activity. Although the activity in the transgenic embryos is not necessarily correlated with the level of gene expression, the two events that did not express the gene (T16 and T19) also lacked the activity. Also, the event with the highest expression of mannan synthase gene also had the highest mannan synthase activity.

Of the twelve transgenic events, three had as high or higher specific mannan synthase activity as guar seed membrane preparation. This suggests that it might be possible to accumulate high levels of the enzyme product in the soybean seeds.

The significant outcomes of this experiment are that this is the first example of the successful functional expression of a plant beta-polysaccharide synthase in any heterologous system and that the mannan synthase polypeptide is autonomously functional in a heterologous system. This experiment does not, however, exclude the possibility of some endogenous soybean polypeptides or polypeptide complexes interacting with the mannan synthase polypeptide to render it functional. On a specific basis, the mannan synthase activity is expressed at as high or higher a level as in the guar seed in some of the events, demonstrating that the mannan synthase nucleotide sequences of the invention can be used to produce gums successfully in soybean seeds.

Example 12

Transformation and Regeneration of Transgenic Plants

Immature maize embryos from greenhouse donor plants are bombarded with a plasmid containing the mannan synthase or galactosyltransferase nucleotide sequence operably linked to a Glob1, Gama-zein, Oleosin, or F3.7 and the selectable marker gene PAT (Wohlleben et al. (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the mannan synthase or galactosyltransferase nucleotide sequence operably linked to a Glob1, Gama-zein, Oleosin, or F3.7 is made. This plasmid DNA plus plasmid DNA containing a PAT selectable marker is precipitated onto 1.1 μm (average diameter) tungsten pellets using a $CaCl_2$ precipitation procedure as follows:
  100 μl prepared tungsten particles in water
  10 μl (1 μg) DNA in Tris EDTA buffer (1 μg total DNA)
  100 μl 2.5 M $CaCl_2$
  10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for mannan synthase or galactosyltransferase activity, or gum production. Gum can be isolated from plant tissues by methods that are known to those of ordinary skill in the art including, but not limited to, the methods of Maier et al.((1993) "Guar, Locust Bean, Tara, and Fenugreek Gums," In: *Industrial Gums: Polysaccharides and their Derivatives*, Whistler and BeMiller, eds., Academic Press, Inc., London, pp. 181-226, and references cited therein) and Reid ((1985) *Adv. Bot. Res.* 11:125-155, and references cited therein); all of which are hereby herein incorporated by reference Bombardment and Culture Media Bombardment medium (560Y) comprises 4.0 g/l N6 basal salts (SIGMA C-1416),1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 13

*Agrobacterium*-Mediated Transformation and Regeneration of Transgenic Plants

For *Agrobacterium*-mediated transformation of maize with a mannan synthase or galactosyltransferase nucleotide sequence, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring t mannan synthase or galactosyltransferase nucleotide sequence to at least one cell of at least one of the immature embryos (step 1: the infection step). In this step the immature embryos are preferably immersed in an *Agrobacterium* suspension for the initiation of inoculation. The embryos are co-cultured for a time with *the Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Example 14

Transformation Soybean Embryo Transformation and Regeneration of Transgenic Soybean Plants Soybean embryos are bombarded with a plasmid containing the mannan synthase or galactosyltransferase nucleotide sequence operably linked to a β-conglycinin promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature (London)* 327:70-73, U.S. Pat. No. 4,945,050). A DuPont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188), and the 3' region of the nopaline synthase gene from the T-DNA of the Ti plasmid of *Agrobacterium tumefaciens*. The expression cassette comprising the mannan synthase or galactosyltransferase nucleotide sequence operably linked to the β-conglycinin can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1

M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 15

Transformation and Regeneration of Transgenic Sunflower Plants

Sunflower meristem tissues are transformed with an expression cassette containing the mannan synthase or galactosyltransferase nucleotide sequence operably linked to a Phaseolin or SF2 as follows (see also European Patent Number EP 0 486233, herein incorporated by reference, and Malone-Schoneberg et al. (1994) *Plant Science* 103:199-207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al.(1990) *Plant Cell Rep.* 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.*, 15: 473-497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid (GA$_3$), pH 5.6, and 8 g/l Phytagar.

The explants are subjected to microprojectile bombardment prior to Agrobacterium treatment (Bidney et al. (1992) *Plant Mol. Biol.* 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the mannan synthase or galactosyltransferase nucleotide sequence operably linked to the β-conglycinin promoter is introduced into *Agrobacterium* strain EHA105 via freeze-thawing as described by Holsters et al. (1978) *Mol. Gen. Genet.* 163:181-187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an OD$_{600}$ of about 0.4 to 0.8. The *Agrobacterium* cells are pelleted and resuspended at a final OD$_{600}$ of 0.5 in an inoculation medium comprised of 12.5 mM MES pH 5.7, 1 gm/l NH$_4$Cl, and 0.3 gm/l MgSO$_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying mannan synthase or galactosyltransferase activity, or gum production.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of T$_0$ plants (parental generation) maturing in the greenhouse are identified by NPTII ELISA and/or by mannan synthase or galactosyltransferase activity analysis of leaf extracts while transgenic seeds harvested from NPTII-positive T$_0$ plants are identified by mannan synthase or galactosyltransferase activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 μm tungsten particles are resuspended in 150 μl absolute ethanol. After sonication, 8 μl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 μg/l kanamycin is resuspended in an inoculation medium (12.5 mM 2-mM 2-(N-morpholino) ethanesulfonic acid, MES, 1 g/l NH$_4$Cl and 0.3 g/l MgSO$_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 μg/ml cefotaxime). The plantlets are cultured on the medium for about two weeks under 16-hour day and 26° C. incubation conditions.

Explants (around 2 cm long) from two weeks of culture in 374C medium are screened for mannan synthase or galactosyltransferase activity using assays known in the art Edwards et al. (1989) *Planta* 178:41-51. After positive (i.e., for mannan synthase or galactosyltransferase expression) explants are identified, those shoots that fail to exhibit mannan synthase or galactosyltransferase activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for mannan synthase or galactosyltransferase expression are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

Example 16

Figure 15:
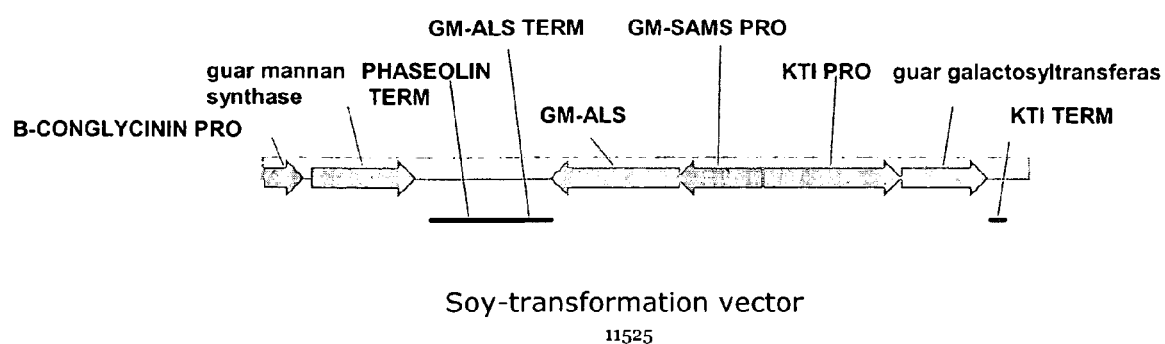
FIG. 15 is a vector construct used to transform soybean cells and to generate plants containing both the mannan synthase (ManS) and galactosyltransferase (GalT1) genes. The vector contains the guar galactosyltransferase gene cloned behind the Kunitz soybean Trypsin Inhibitor (KTi) promoter [Jofuku et al., (1989) *Plant Cell* 1:1079-1093], followed by the KTi 3' termination region. The plasmid also contains a mutated form of the soy acetolactate synthase (ALS) that is resistant to sulfonylurea herbicides.

Stable Transformation of Soybean Cells with Guar Mannan Synthase and Galactosyltransferase Genes and Regeneration of Plants A vector construct was used to transform soybean cells and to generate plants as described in example 10 (as filed with the patent application) but containing both the mannan synthase (ManS) and galactosyltransferase (GalT1) genes (FIG. 15). Plants were derived by the transformation of soybean embryogenic suspension cultures with pKS237. pKS237 contains the guar galactosyltransferase gene cloned behind the Kunitz soybean Trypsin Inhibitor (KTi) promoter [Jofuku et al., (1989) *Plant Cell* 1:1079-1093], followed by the KTi 3' termination region, the isolation of which is described in U.S. Pat. No. 6,372,965.

Figure 16:
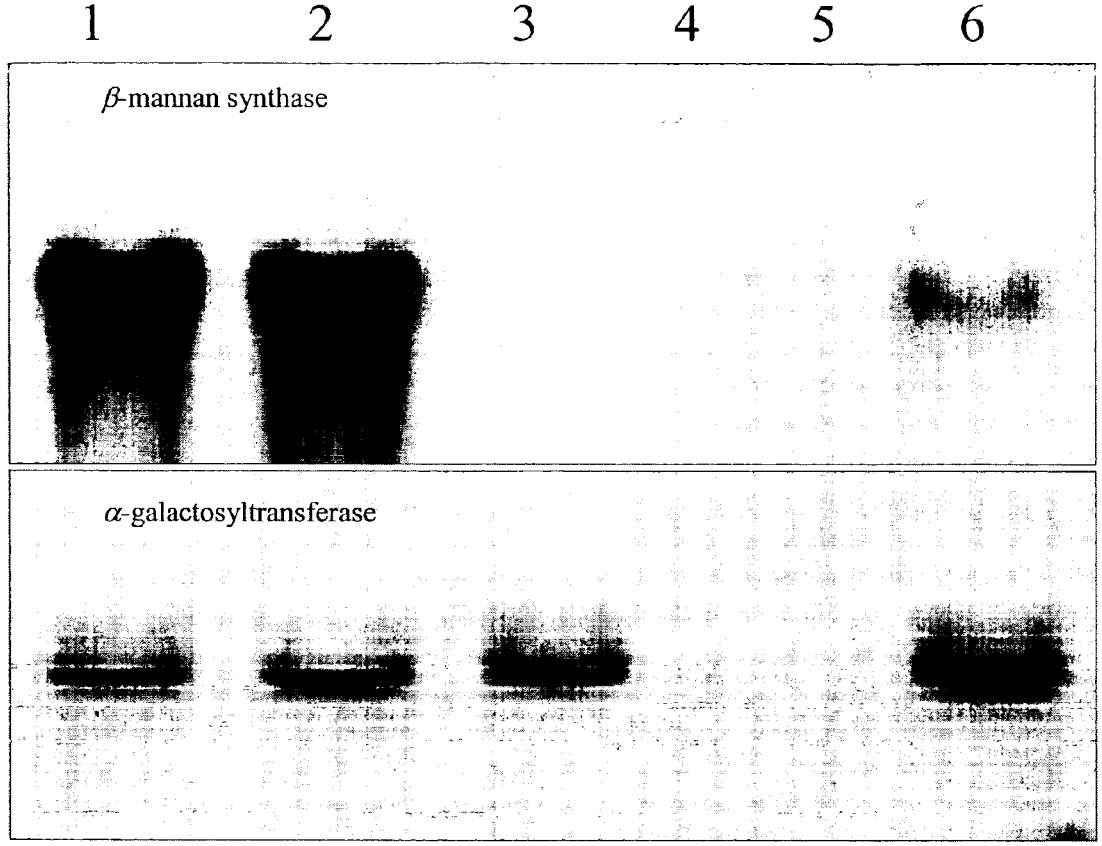
FIG. 16 is a Northern blot of six soybean transgenic somatic embryos transformed with the vector construct containing both the mannan synthase and galactosyltransferase genes. The blots were probed with mannan synthase (top) or galactosyltransferase gene probes (below). Each lane represents an independent event.
Figure 18:
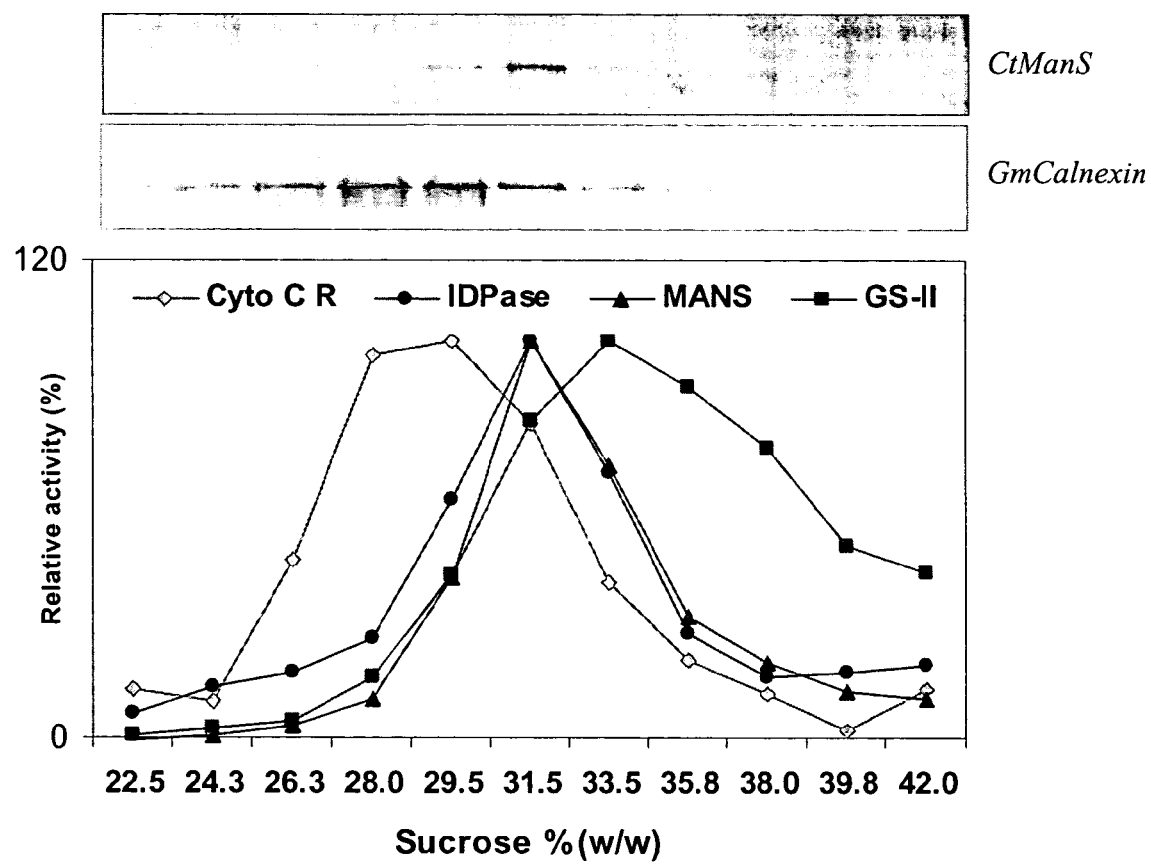
FIG. 18 shows enzyme activities corresponding to different intracellular compartments in different fractions of an isopycnic sucrose density gradient of the particulate fraction of soybean somatic embryos expressing the mannan synthase gene.

Plasmid pKS237 also contains a mutated form of the soy acetolactate synthase (ALS) that is resistant to sulfonylurea herbicides. ALS catalyzes the first common step in the biosynthesis of the branched chain amino acids isoleucine, leucine, and valine (Keeler et al, *Plant Physiol* 1993 102: 1009-18). Inhibition of native plant ALS by several classes of structurally unrelated herbicides including sulfonylureas, imidazolinones, and triazolopyrimidines, is lethal (Chong C K, Choi J D *Biochem Biophys Res Commun* 2000 279:462-7). Overexpression of the mutated sulfonylurea-resistant ALS gene allows for selection of transformed plant cells on sulfonylurea herbicides. The ALS gene is cloned behind the SAMS promoter. The SAMS:ALS expression cassette is the same as in pZSL13LeuB [BB1205 patent application was published as WO 00/37662]. In addition, plasmid pKS237 contains beta-conglycinin promoter, guar mannan synthase gene, followed by a phaseolin 3' terminator from pKS211. Seven days post bombardment, the liquid media is exchanged with fresh SB55 containing chlorsulfuron at a final concentration of 100 ng/ml. Stable plants were generated from six events, three (events 1, 2, and 6) of which express both the genes as determined by Northern analysis (FIG. 16). The Northern blots were probed with the β-mannan synthase (above) or β-galactosyltransferase genes as described in examples 7 and 8.

Example 17

Antibody Production against the Catalytic Domain of Mannan Synthase

The 269-aa region corresponding to aa 92-360 in the MANS sequence between the first and the second predicted transmembrane domains (Example 6, FIG. 10) was expressed as a fusion protein in pET32b containing thioredoxin protein (TRX) or pET42b containing glutathione-S-transferase (GST) fusion tags (Novagen, Madison, Wis.). The amino acid sequence of the truncated mannan synthase gene used to make fusion proteins is shown below (SEQ ID NO 7):

MVLIQIPMYNEKEVYKLSIGAVCGLSWPADRFIVQVLDDSTNPVLRELVE

MECQKWIQKGVNVKYENRRNRNGYKAGALKEGLEKQYVEDCEFVAIFDAD

FQPDADFLWNTIPYLLENPKLGLVQARWKFVNSEECMMTRLQEMSLDYHF

SVEQEVGSSTYSFFGFNGTAGVWRIQAIKDAGGWKDRTTVEDMDLAVRAS

LHGWEFVFVGDVKVKNELPSTFKAYRFQQHRWSCGPANLFKKMTKEIICC

KRVPLLKRLHLIYAFFFVR

M13 reverse primer and one gene-specific primer containing an introduced stop codon
and an XhoI site (TTGTCTCGAGTTATCTCACAAA-GAAGAAAGCAT) (SEQ ID NO: 8), were used to amplify the predicted mannan synthase soluble domain from the mannan synthase gene by PCR using Pwo polymerase (Roche). The NcoI-XhoI digested PCR fragment (sequence below) and pET vectors (pET-32b or pET-42b) were ligated using Rapid DNA liagtion kit (Roche) and transformed into *E. coli* DH5αcells (Novagen). The plasmid DNA was transformed into the strain BL21 (DE3) (Novagen) for protein production.

The fusion protein from both the vectors was insoluble and was not susceptible to the protease action after solubilization. FIG. 17 shows the expression of the fusion proteins, and the purified proteins used for antibody production. After purification on a preparative scale in SDS gels followed by electroelution in Electroelute (S&S), the fusion proteins were sent to Strategic BioSolutions (52 Anderson Road, Windham, Me. 04062) for antibody production in rabbits. The antibody raised against either of the fusion proteins recognized a polypeptide band of about 55 kDa on Western blots derived from the guar endosperm membrane fraction. A polypeptide band of a slightly lower molecular mass was detected by the antibody in transgenic soybean somatic embryos. Antibody specific to the mannan synthase domain was purified by binding and eluting the antiserum to the fusion protein immobilized on nitrocellulose filters. GST-fusion was used to purify antibody raised against the TRX-fusion and vice versa. Similar results were obtained on Western blots as with the non-purified antibody.

Example 18

Intracellular Localization of Mannan Synthase in Transgenic Soybean Cells by Cell Fractionation Particles prepared from transgenic somatic soybean embryos expressing the mannan synthase gene (Examples 1 and 11) were subjected to isopycnic centrifugation exactly as described for digitonin-solubilized guar seed particles (Example 2) as described in Example 1 except that a sucrose gradient (20-45%, w/w) was used. The fractions were assayed, as previously described (Dhugga, K. S., Ulvskov, P., Gallagher, S. R., and Ray, P. M. (1991). Plant polypeptides reversibly glycosylated by UDP-glucose. Possible components of Golgi β-glucan synthase in pea cells. *J. Biol. Chem.* 266, 21977-21984) for the following enzymes: Cyto C R or cytochrome c reductase (an endoplasmic reticulum marker), MANS or mannan synthase, IDPase (a Golgi marker), and GS-II or glucan synthase-II or callose synthase (a plasma membrane marker).

As shown in FIG. 17, mannan synthase comigrates with the Golgi marker, IDPase, and is clearly separated from the endoplasmic reticulum and the plasma membrane fractions. In correspondence, the antibody raised against the globular domain of the mannan synthase polypeptide recognizes a polypeptide band of ~55 kDa the distribution of which is parallel to that of the mannan synthase activity in the gradient fractions.

These results show that the mannan synthase activity is localized to the Golgi compartment. Other than cellulose and callose, all the cell wall matrix polysaccharides, of which galactomannan is a member, are known to be synthesized in the Golgi and then exported to the cell wall by exocytosis (Ray, P. M., Eisinger, W. R., and Robinson, D. G. (1976). Organelles involved in cell wall polysaccharide formation and transport in pea cells. *Ber. Deutsch. Bot. Ges. Bd*. 89, 121-146.). Not only is mannan synthase targeted to the right compartment, it is also enzymatically functional. These results indicate that it should be possible to produce galactomannan polysaccharide in the non-galactomannan producing crop seeds, such as soybean.

Example 19

Analysis of the Enzyme Product from Transgenic Somatic Embryos and the Transgenic Soybean Seeds Expressing the Guar Mans and GalT1 Genes Product Digestion and HPLC Protocol:

Sugar composition was determined by high-performance anion exchange chromatography using a Dionex DX500 chromatography system consisting of a AS3500 autosampler, and ED40 electrochemical detector as described elsewhere (Prodolliet, J., Bugner, E., and Feinberg, M., 1995, Determination of carbohydrates in soluble coffee by anion-exchange chromatography with pulsed amperometric detection: Interlaboratory study. *J AOAC Intl* 78, 768-782). Powdered guar seeds or seed parts (50 mg) were digested in 1 mL 72% (w/w) $H_2SO_4$ for 12 hours with mixing on a Nutator (Clay-Adams) followed by centrifugation for 10 min at 14,000×g in a microfuge (Eppendorf 5417C).

The digested material was neutralized with a 0.18 M $Ba(OH)_2$ solution followed by the addition of powdered $BaCO_3$ until the pH approached 7. After centrifugation, 25 μl of the supernatant was applied to a 250×4 mm Dionex CarboPac PA-1 column coupled downstream to an IonPac ATC-1 column and a CarboPac PA-1 guard column. Sugars were eluted in steps as follows: 1 mL $min^{-1}$ with water for 25 min, 200 mM NaOH containing 120 mM NaOAc for 20 min, and 300 mM NaOH for 10 min. Post-column, 300 mM NaOH at a rate of 0.5 mL $min^{-1}$ was introduced using a Waters model 510 pump. Settings for the pulsed amperometric detector were according to the manufacture's recommendations. Sugar concentrations were measured using a 5-point calibration curve obtained using standard sugars.

Product Analysis:

Product made with radiolabeled substrate (Example 1), after precipitation with ethanol, was speed-vac dried. The pellet was subjected to different carbohydrate hybrolases (Megazyme)

The reaction was carried out as described in Example 1 using guar seed, transgenic soybean somatic embryos or developing seeds. After completion of the reaction, 100 ul of 1 M sodium acetate, pH 4.0, was added followed by five units each of endo-β-1,4-mannanase, cellulase (endo-β-1,4-glucanase), or lichenase (endo-β-1,3-1,4-glucanase or mixed-linked glucanase) (Megazyme International Ireland Ltd. Bray Business Park, Bray, Co.Wicklow, Ireland), and incubated at 40° C. for 16 h. The reaction contents were assayed as described in Example 1.

Figure 19:
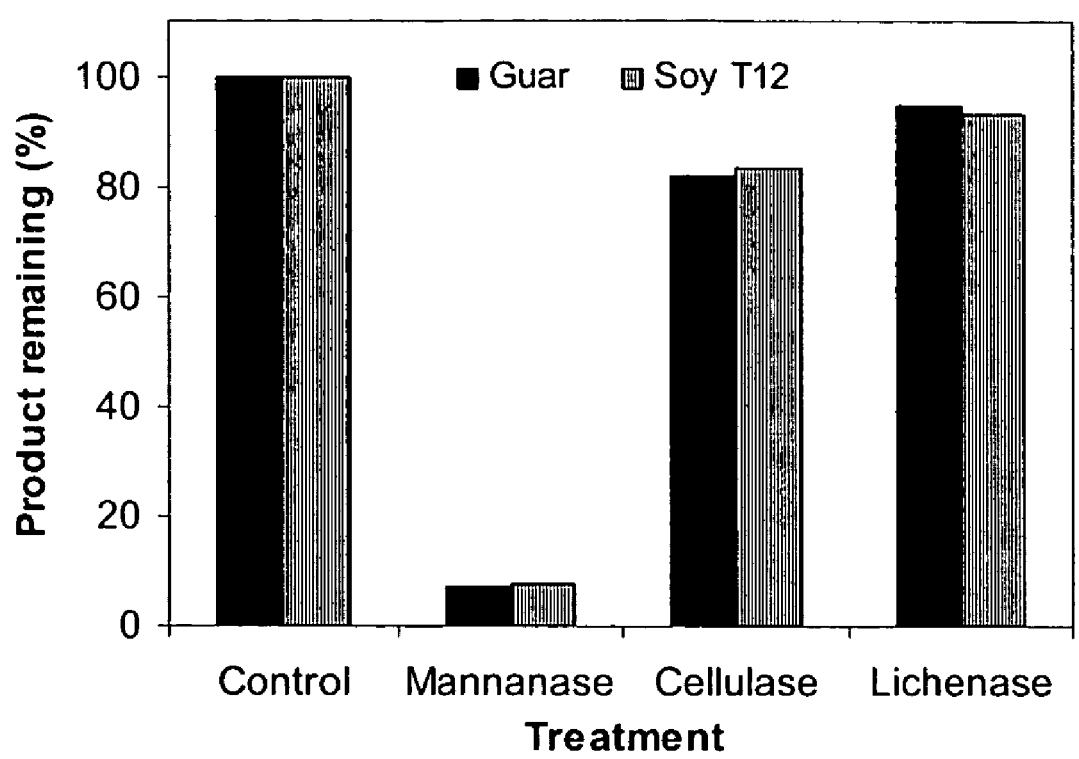
FIG. 19 details analysis of the product made from transgenic soybean somatic embryo (event T12) and guar seed particulate fractions by the mannan synthase activity.

The results are shown in FIG. 19. Neither lichenase nor cellulase appreciably degraded the product made from either guar or soybean somatic embryos containing the ManS transgene. Endo β-mannanse, however, hydrolyzed the product to near completion in each case, showing that the product made in vitro is indeed β-1,4-mannan as is found in natural galactomannan gums.

To further verify whether mannose was enzymatically converted to other sugars during the mannan synthase reaction, the radiolabeled reaction product was digested in 72% $H_2SO_4$ overnight, neutralized as described above and subjected to HPLC separation.

Standards were prepared by incubating the NDP-[$^{14}$C]-sugars (UDP-galactose, UDP-glucose, UDP-xylose, and GDP-mannose) in 72% $H_2SO_4$ overnight. The mixture was neutralized as described above, passed through a strong anion exchange column and subjected to HPLC analysis.

The elution profile of the radiolabeled sugars was identical to that of the unlabeled sugars (data not shown). When the acid-digested product made from the guar seed, soybean transgenic somatic embryos or developing seeds was subjected to HPLC analysis, only mannose was detected (more information on product formation in FIG. 14, Example 11), indicating no detectable conversion of mannose into other sugars during the reaction (FIG. 20). The supernatant from the reaction product also contained only mannose, indicating that no detectable conversion to other sugars took place during the reaction. These data confirm the identity of the ManS gene as catalyzing the polymerization of mannosyl residues into a mannan chain. Combined with the data obtained using linkage-specific endo-β-hydrolases, these data confirm that the functionally expressed guar ManS enzyme in soybean somatic embryos and seeds makes β-1,4-mannan.

Mature Seed Total Sugar Composition:

Mature seeds were obtained from three events (Example 16, FIG. 16, lanes 1, 2, and 6) and the control, nontransgenic plant. Twenty seeds from each of the transgenic event and ten seeds from the control plant were ground into a fine powder and analyzed for sugar composition as described above. In the transgenic events 1 and 3 the mannose concentration is increased by two percentage points whereas in the event 2 it is increased by three percentage points in comparison to the control. No correlation of mannose concentration with the seed mass is observed as the three event produced seeds or smaller than the control yet had elevated level of mannose. This suggests that mannose synthase is active in the developing seed.

Soybean seeds, unlike mannose, have a higher concentration of galactose to start with, so it is difficult to determine with certainty whether any alteration in galactose concentration is related to the galactomannan polysaccharide. Galactose concentration is reduced by three percentage points in events 2 and 3 but is increased by one percentage point in event 1. A reduction in galactose content in the seeds expressing both the mannan synthase and the galactosyltransferase genes could actually result from a greater reduction in galactan content than is compensated by the galactosylation of the mannosyl residues on the mannan chain. Galactose concentration in the galactomannan produced by the transgenes is expected to be much lower than the mannose concentration because only one in every few mannosyl residues is expected to be galactosylated. Definitive answer will be obtained from the subsequent generations when larger quantities of the homogenous transgenic seeds become available. The galactomannan polysaccharides will be isolated from the milled flour and analyzed for sugar composition.

Example 20

GDP-Mannose Transporter Gene Isolation from Guar

Sugar nucleotide transporters are present in the Golgi cisternal membranes to transport substrates for use in polysaccharide formation and protein glycosylation [1-5]. The genes involved in the formation of galactomannan which included mannan synthase, galactosyltransferase, phosphomannoisomerase (PMI), and GDP-mannose pyrophosphorylase were identified. A transporter that facilitates the movement of GDP-mannose, substrate for beta-mannan formation, across the cisternal membrane was isolated. (FIGS. 21 and 22, SEQ ID NOS 9 and 10)

Figure 25:
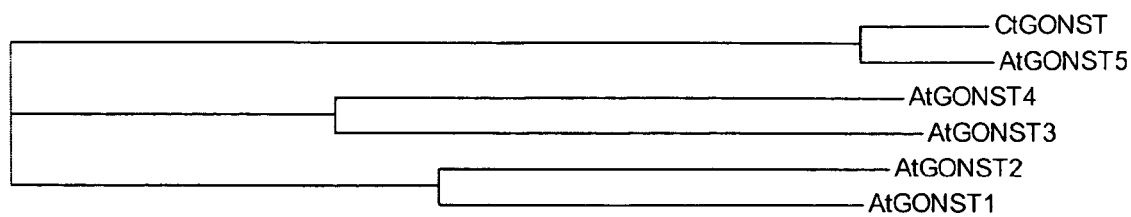
FIG. 25 is a cladogram showing the relationship of the guar GDP-mannose transporter to the *Arabidopsis* transporters. CtGONST is most closely related to GONST5.

The ~1.4 kb cDNA contains an open reading frame encoding a polypeptide of 342 amino acids with a molecular mass of 38.8 kDa and an isoelectric point of 9.26. Of the five *Arabidopsis* GDP-mannose transporters available in the database, the guar transporter appears to be an ortholog of GONST5. (FIGS. 23, 24 and 25)

Figure 26:
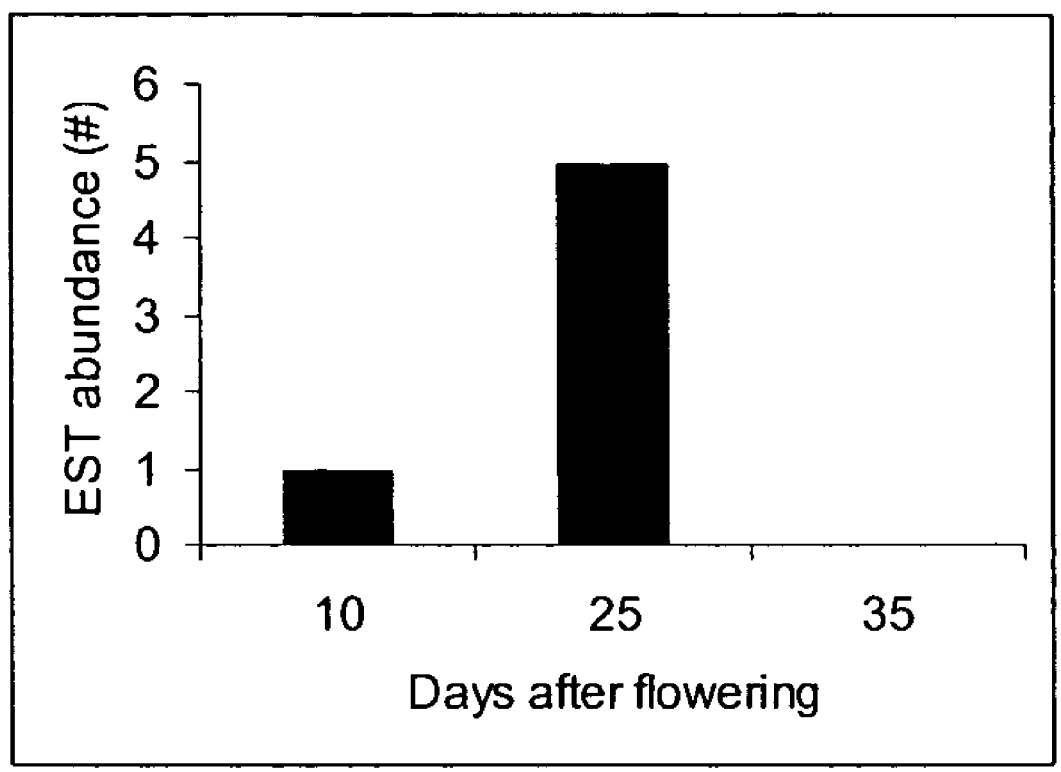
FIG. 26 is a graph showing the expression of the guar GDP-mannose transporter corresponding to the mannan synthase activity.
Figure 27:
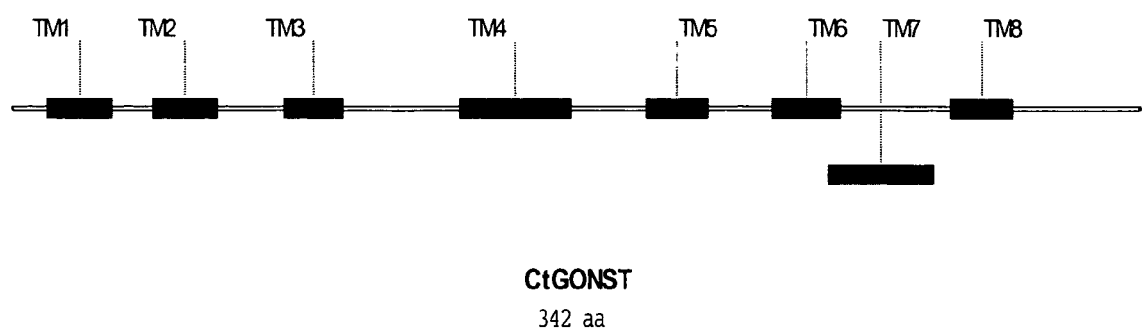
FIG. 27 details the transmembrane topology for the guar GDP-mannose transporter orthologs of the *Arabidopsis* GONST5 (GDP-mannose pyrophosphorylase) as determined by the TMPRED program, showing the 6-7 transmembrane domains. The membrane spanning regions are marked by grey rectangular boxes on the protein molecule, which is depicted by the narrow gray rod. These transmembrane domains are required to create a pore through the Golgi membrane for the transport of GDP-mannose, the substrate for the mannan chain formation in galactomannan.

The expression pattern of the guar transporter gene corresponds to that of mannan synthase activity in developing guar seeds (see FIG. 26). As expected for it to be a transporter, the guar transporter reported here has 6-7 transmembrane domains (FIG. 27). The topology of the guar ortholog of the *Arabidopsis* GONST5 (GDP-mannose pyrophosphorylase) was determined by the TMPRED program (available from the Swiss Institute for Experimental Cancer Research (ISREC), a founding member of the Swiss Institute for Bioinformatics (SIB) (Swiss Institute of Bioinformatics, Bâtiment Ecole de Pharmacie-room 3041, Université de Lausanne,1015 Lausanne-Dorigny, Switzerland)). This program predicted eight transmembrane domains that are listed in the FIG. 27. The membrane spanning regions are marked by blue boxes on the protein molecule, which is depicted by the gray rod. These transmembrane domains are required to create a pore through the Golgi membrane for the transport of GDP-mannose, the substrate for the mannan chain formation in galactomannan. The number of transmembrane domains is the same as in *Arabidopsis* protein, GONST5 (Baldwin, T. C., Handford, M. G., Yuseff, M. I., Orellana, A., and Dupree, P. (2001). Identification and characterization of GONST1, a Golgi-localized GDP-mannose transporter in *Arabidopsis*. Plant Cell 13, 2283-2295).

Since in the plant species where galactomannan is not a major wall polysaccharide, the requirement for the substrate GDP-mannose is much lower (as it is mainly used for the decoration of proteins and minor wall polysaccharides). To produce large quantities of galactomannan in these types of plants, such as soybean, expression of the guar GONST5 gene would be very desirable. The other two enzymes that could help in improving the levels of galactomannan in guar seeds are phosphomannoisomerase and GDP-mannose pyrophosphorylase. Very high identity to the known GONST protein (90% to AtGONT5, Example 24) and the expression pattern of this gene in guar seeds that mirrors galactomannan formation (Example 26) both indicate that the guar GONST is a GDP-mannose transporter.

When expressing the galactomannan forming genes in soybean, GDP-mannose transport from the cytosol into the lumen may limit the amount of substrate for optimal synthesis of galactomannan. One can overexpress the guar GDP-mannose transporter along with the other genes mentioned above to obtain high levels of galactomannan in transgenic soybean seeds.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

This invention may be embodied in many different forms and should not be construed as limited to the embodiments set forth herein; rather, these embodiments are provided so that this disclosure will be thorough and complete, and will fully convey the scope of the invention to those skilled in the art.

Many modifications and other embodiments of the invention will come to mind to one skilled in the art to which this invention pertains having the benefit of the teachings presented in the forgoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation. Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule comprising one nucleotide sequence selected from the group consisting of:
   (a) the nucleotide sequence set forth in SEQ ID NO:1;
   (b) a nucleotide sequence encoding the amino acid sequence set forth in SEQ ID NO:2;
   (c) a nucleotide sequence having at least 90% identity to the nucleotide sequence set forth in SEQ ID NO:1, wherein said nucleotide sequence encodes a polypeptide having mannan synthase activity;
   (d) a fragment of the nucleotide sequence set forth in SEQ ID NO:1, wherein said fragment encodes a polypeptide having mannan synthas activity; and
   (e) a nucleotide sequence that is complementary to the nucleotide sequence of (a), (b), (c), or (d).

2. An expression cassette comprising a nucleic acid molecule of claim 1 operably linked to a promoter that drives expression in a non-human host cell.

3. A vector comprising the expression cassette of claim 2.

4. A non-human host cell having stably incorporated in its genome the expression cassette of claim 2.

5. A plant cell having stably incorporated in its genome the expression cassette of claim 2.

6. A transformed plant comprising in its genome at least one stably incorporated nucleotide construct comprising a nucleotide sequence operably linked to a promoter that is capable of driving expression in a plant cell, wherein said nucleotide sequence is selected from the group consisting of:
   (a) the nucleotide sequence set forth in SEQ ID NO:1;
   (b) a nucleotide sequence encoding the amino acid sequence set forth in SEQ ID NO:2;
   (c) a nucleotide sequence having at least 90% identity to the nucleotide sequence set forth in SEQ ID NO:1, wherein said nucleotide sequence encodes a polypeptide having mannan synthase activity;
   (d) a fragment of the nucleotide sequence set forth in SEQ ID NO:1, wherein said fragment encodes a polypeptide having mannan synthas activity; and
   (e) a nucleotide sequence that is complementary to the nucleotide sequence of (a), (b), (c), or (d).

7. The plant of claim 6, wherein said plant is a monocot.

8. The plant of claim 7, wherein said monocot is selected from the group consisting of maize, wheat, rice, sorghum, rye, millet, and barley.

9. The plant of claim 6, wherein said plant is a dicot.

10. The plant of claim 9, wherein said dicot is selected from the group consisting of soybean, sunflower, safflower, alfalfa, potato, *Brassica* spp., cotton, tomato, tobacco, peanut, guar, locust bean, and fenugreek.

11. The plant of claim 6, wherein said promoter is selected from the group consisting of constitutive, pathogen-inducible, chemical-regulated, wound-inducible, and insect-inducible promoters.

12. A seed of the plant of any one of claims 6-11, wherein said seed comprises in its genome at least one of said nucleotide constructs.

13. A method for altering the level of galactomannan in a plant, said method comprising transforming a plant with a nucleotide construct comprising a nucleotide sequence operably linked to a promoter that is capable of driving expression in a plant cell, wherein said nucleotide sequence is selected from the group consisting of:
   (a) the nucleotide sequence set forth in SEQ ID NO:1;
   (b) a nucleotide sequence encoding the amino acid sequence set forth in SEQ ID NO:2;
   (c) a nucleotide sequence having at least 90% identity to the nucleotide sequence set forth in SEQ ID NO:1, wherein said nucleotide sequence encodes a polypeptide having mannan synthase activity;
   (d) a fragment of the nucleotide sequence set forth in SEQ ID NO:1, wherein said fragment encodes a polypeptide having mannan synthas activity; and
   (e) a nucleotide sequence that is complementary to the nucleotide sequence of (a), (b), (c), or (d).

14. The method of claim 13, wherein said method further comprises regenerating a stably transformed plant from said cell.

15. The method of claim 13, wherein said plant is a monocot.

16. The method of claim 15, wherein said monocot is selected from the group consisting of maize, wheat, rice, sorghum, rye, millet, and barley.

17. The method of claim 13, wherein said plant is a dicot.

18. The method of claim 16, wherein said dicot is selected from the group consisting of soybean, sunflower, safflower, alfalfa, potato, *Brassica* spp., cotton, tomato, tobacco, peanut, guar, locust bean, and fenugreek.

19. The method of claim 13, wherein said promoter is selected from the group consisting of constitutive, pathogen-inducible, chemical-regulated, wound-inducible, and insect-inducible promoters.

20. A method for producing gum comprising:
   (a) obtaining a transformed plant, said transformed plant comprising in its genome a nucleotide construct comprising a nucleotide sequence encoding a mannan synthase, said nucleotide sequence operably linked to a promoter that is capable of driving expression in a plant cell;
   (b) maintaining said transformed plant under conditions favorable for the production of gum in said transformed plant or in at least one part thereof;
   (c) harvesting said transformed plant or said part; and
   (d) extracting said gum from said plant or said part.

21. The method of claim 20, wherein said nucleotide sequence encoding a mannan synthase is selected from the group consisting of:
   (a) the nucleotide sequence set forth in SEQ ID NO:1;
   (b) a nucleotide sequence encoding the amino acid sequence set forth in SEQ ID NO:2;
   (c) a nucleotide sequence having at least 90% identity to the nucleotide sequence set forth in SEQ ID NO:1, wherein said nucleotide sequence encodes a polypeptide having mannan synthase activity; and
   (d) a fragment of the nucleotide sequence set forth in SEQ ID NO:1, wherein said fragment encodes a polypeptide having mannan synthas activity.

22. The method of claim 13, wherein said nucleotide construct additionally comprises a GDP-mannose transporter polynucleotide in soybean selected from the group consisting of:
   (a) the nucleotide sequence set forth in SEQ ID NO: 9; and
   (b) a nucleotide sequence encoding the amino acid sequence set forth in SEQ ID NO: 10.

* * * * *

UNITED STATES PATENT AND TRADEMARK OFFICE
CERTIFICATE OF CORRECTION

| | | |
|---|---|---|
| PATENT NO. | : 7,265,265 B2 | Page 1 of 1 |
| APPLICATION NO. | : 10/713836 | |
| DATED | : September 4, 2007 | |
| INVENTOR(S) | : Dhugga et al. | |

It is certified that error appears in the above-identified patent and that said Letters Patent is hereby corrected as shown below:

<u>Title Page</u>
Item (75) Inventors, should read as follows:
-- (75) Inventors: Kanwarpal S. Dhugga, Johnston, IA (US)
              Roberto Barreiro, Johnston, IA (US) --

<u>Column 66</u>
Line 45-57 should read as follows:
-- 21.   The method of claim 20, wherein said nucleotide sequence encoding a mannan synthase is selected from the group consisting of:
    (a)   the nucleotide sequence set forth in SEQ ID NO:1;
    (b)   a nucleotide sequence encoding the amino acid sequence set forth in SEQ ID NO:2;
    (c)   a nucleotide sequence having at least 90% identity to the nucleotide sequence set forth in SEQ ID NO:1, wherein said nucleotide sequence encodes a polypeptide having mannan synthase activity; and
    (d)   a fragment of the nucleotide sequence set forth in SEQ ID NO:1, wherein said fragment encodes a polypeptide having mannan synthase activity. --

Signed and Sealed this

Eighth Day of September, 2009

David J. Kappos
*Director of the United States Patent and Trademark Office*